US009483615B2

(12) United States Patent
Roberts

(10) Patent No.: US 9,483,615 B2
(45) Date of Patent: Nov. 1, 2016

(54) COMMUNICATION OF ORIGINAL AND UPDATED PUMP PARAMETERS FOR A MEDICAL INFUSION PUMP

(75) Inventor: Nick Roberts, Cumming, GA (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 2099 days.

(21) Appl. No.: 12/189,624

(22) Filed: Aug. 11, 2008

(65) Prior Publication Data
US 2009/0156991 A1 Jun. 18, 2009

Related U.S. Application Data

(60) Provisional application No. 60/964,444, filed on Aug. 10, 2007.

(51) Int. Cl.
*G06Q 10/00* (2012.01)
*G06Q 50/00* (2012.01)
*G06F 19/00* (2011.01)
*G06Q 50/22* (2012.01)

(52) U.S. Cl.
CPC ............. *G06F 19/327* (2013.01); *G06Q 50/22* (2013.01); *G06F 19/3456* (2013.01)

(58) Field of Classification Search
CPC ........... G06F 19/3468; G06F 19/3412; G06F 19/322; G06F 19/3406; G06F 19/3443; G06F 19/345; G06F 19/3487; A61M 2205/6018; A61M 5/142; G06Q 50/22; G06Q 50/24
USPC ....................................................... 705/2–3
See application file for complete search history.

(56) References Cited

U.S. PATENT DOCUMENTS

| | | | |
|---|---|---|---|
| 5,262,943 A | 11/1993 | Thibado et al. | |
| 5,317,506 A | 5/1994 | Coutre et al. | |
| 5,368,562 A | 11/1994 | Blomquist et al. | |
| 5,401,059 A | 3/1995 | Ferrario | |
| 5,447,164 A | 9/1995 | Shaya et al. | |

(Continued)

FOREIGN PATENT DOCUMENTS

WO 2006/108858 A1 10/2006

OTHER PUBLICATIONS

Official Action dated Jun. 23, 2010 issued in related U.S. Appl. No. 12/189,541 (19 pages).

*Primary Examiner* — Reginald R Reyes
(74) *Attorney, Agent, or Firm* — Seager, Tufte & Wickhem, LLP

(57) ABSTRACT

Methods and systems of patient treatment are disclosed. The methods and systems include use of medical device informatics to modify and validate therapies and drugs used in those therapies. In certain embodiments, a medical device, such as a medical infusion pump, interfaces with a server to administer the patient treatments. In one aspect, a method of tracking changed parameters in a medical infusion pump is disclosed. The method includes establishing a communication session between a medical infusion pump and a medical device server, and communicating an original parameter value, an updated parameter value, and a final parameter value from the medical infusion pump to the medical device server. The method further includes storing the original parameter value, the updated parameter value, and the final parameter value on the medical device server. Metadata associated with one or more of the parameter values identifies that parameter value to the medical device server and the medical infusion pump.

24 Claims, 52 Drawing Sheets

(56) References Cited

U.S. PATENT DOCUMENTS

| | | |
|---|---|---|
| 5,542,420 A | 8/1996 | Goldman et al. |
| 5,549,117 A | 8/1996 | Tacklind et al. |
| 5,594,786 A | 1/1997 | Chaco et al. |
| 5,626,144 A | 5/1997 | Tacklind et al. |
| 5,651,775 A | 7/1997 | Walker et al. |
| 5,681,285 A | 10/1997 | Ford et al. |
| 5,689,229 A | 11/1997 | Chaco et al. |
| 5,700,998 A | 12/1997 | Palti |
| 5,704,366 A | 1/1998 | Tacklind et al. |
| 5,732,401 A | 3/1998 | Conway |
| 5,732,709 A | 3/1998 | Tacklind et al. |
| 5,758,643 A * | 6/1998 | Wong et al. ............... 600/309 |
| 5,764,159 A | 6/1998 | Neftel |
| 5,781,442 A | 7/1998 | Engleson et al. |
| 5,790,409 A | 8/1998 | Fedor et al. |
| 5,814,015 A | 9/1998 | Gargano et al. |
| 5,822,715 A * | 10/1998 | Worthington et al. ......... 702/19 |
| 5,845,255 A | 12/1998 | Mayaud |
| 5,848,593 A | 12/1998 | McGrady et al. |
| 5,895,371 A | 4/1999 | Levitas et al. |
| 5,910,776 A | 6/1999 | Black |
| 5,912,818 A | 6/1999 | McGrady et al. |
| 5,935,099 A * | 8/1999 | Peterson ............... A61M 5/172 604/65 |
| 5,950,630 A | 9/1999 | Portwood et al. |
| 5,971,593 A | 10/1999 | McGrady |
| 5,993,046 A | 11/1999 | McGrady et al. |
| 6,053,887 A | 4/2000 | Levitas et al. |
| 6,074,345 A | 6/2000 | van Oostrom et al. |
| 6,101,478 A | 8/2000 | Brown |
| 6,108,588 A | 8/2000 | McGrady |
| 6,168,563 B1 | 1/2001 | Brown |
| 6,259,654 B1 | 7/2001 | de la Huerga |
| 6,327,501 B1 | 12/2001 | Levine et al. |
| 6,334,778 B1 | 1/2002 | Brown |
| 6,352,200 B1 | 3/2002 | Schoonen et al. |
| 6,368,273 B1 | 4/2002 | Brown |
| 6,381,577 B1 | 4/2002 | Brown |
| 6,409,674 B1 | 6/2002 | Brockway et al. |
| 6,434,569 B1 | 8/2002 | Toshimitsu et al. |
| 6,440,068 B1 | 8/2002 | Brown et al. |
| 6,464,136 B2 | 10/2002 | Walsh |
| 6,470,234 B1 | 10/2002 | McGrady |
| 6,497,358 B1 | 12/2002 | Walsh |
| 6,497,655 B1 | 12/2002 | Linberg et al. |
| 6,551,243 B2 | 4/2003 | Bocionek et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,577,899 B2 | 6/2003 | Lebel et al. |
| 6,585,644 B2 | 7/2003 | Lebel et al. |
| 6,588,670 B2 | 7/2003 | Bukowski |
| 6,605,038 B1 | 8/2003 | Teller et al. |
| 6,618,745 B2 | 9/2003 | Christensen et al. |
| 6,635,014 B2 | 10/2003 | Starkweather et al. |
| 6,635,016 B2 | 10/2003 | Finkelshteins |
| 6,637,649 B2 | 10/2003 | Walsh |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,671,563 B1 | 12/2003 | Engelson et al. |
| 6,687,546 B2 | 2/2004 | Lebel et al. |
| 6,694,191 B2 | 2/2004 | Starkweather et al. |
| 6,702,757 B2 | 3/2004 | Fukushima et al. |
| 6,731,989 B2 | 5/2004 | Engleson et al. |
| 6,733,446 B2 | 5/2004 | Lebel et al. |
| 6,754,538 B2 | 6/2004 | Linberg |
| 6,758,810 B2 | 7/2004 | Lebel et al. |
| 6,811,533 B2 | 11/2004 | Lebel et al. |
| 6,813,519 B2 | 11/2004 | Lebel et al. |
| 6,824,052 B2 | 11/2004 | Walsh |
| 6,830,180 B2 | 12/2004 | Walsh |
| 6,873,268 B2 | 3/2005 | Lebel et al. |
| 6,910,626 B2 | 6/2005 | Walsh |
| 6,915,170 B2 | 7/2005 | Engleson et al. |
| 6,922,729 B1 | 7/2005 | Cheung |
| 6,942,616 B2 | 9/2005 | Kerr, II |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 7,002,468 B2 | 2/2006 | Eveland et al. |
| 7,024,245 B2 | 4/2006 | Lebel et al. |
| 7,051,120 B2 | 5/2006 | Greene et al. |
| 7,061,831 B2 | 6/2006 | De La Huerga |
| 7,066,883 B2 | 6/2006 | Schmidt et al. |
| 7,096,072 B2 | 8/2006 | Engleson et al. |
| 7,103,419 B2 | 9/2006 | Engleson et al. |
| 7,103,578 B2 | 9/2006 | Beck et al. |
| 7,107,106 B2 | 9/2006 | Engleson et al. |
| 7,117,041 B2 | 10/2006 | Engleson et al. |
| 7,130,396 B2 | 10/2006 | Rogers et al. |
| 7,136,916 B2 | 11/2006 | Schade |
| 7,139,844 B2 | 11/2006 | Smith et al. |
| 7,153,289 B2 | 12/2006 | Vasko |
| 7,155,202 B2 | 12/2006 | Helal |
| 7,167,755 B2 | 1/2007 | Seeberger et al. |
| 7,171,274 B2 | 1/2007 | Starkweather et al. |
| 7,216,802 B1 | 5/2007 | De La Huerga |
| 7,246,163 B2 | 7/2007 | Tindal |
| 7,255,683 B2 * | 8/2007 | Vanderveen et al. ......... 604/118 |
| 7,294,105 B1 | 11/2007 | Islam |
| 7,347,819 B2 | 3/2008 | Lebel et al. |
| 7,349,858 B1 | 3/2008 | McGrady et al. |
| 7,357,308 B2 | 4/2008 | Matz |
| 7,369,635 B2 | 5/2008 | Spital et al. |
| 7,398,183 B2 | 7/2008 | Holland et al. |
| 7,413,544 B2 | 8/2008 | Kerr, II |
| 7,423,526 B2 | 9/2008 | Despotis |
| 7,430,608 B2 | 9/2008 | Noonan et al. |
| 7,449,008 B2 | 11/2008 | Hochman |
| 7,454,314 B2 | 11/2008 | Holland et al. |
| 7,461,171 B2 | 12/2008 | Thurner |
| 7,465,301 B2 | 12/2008 | Bek et al. |
| 7,467,093 B1 | 12/2008 | Newton et al. |
| 7,471,994 B2 | 12/2008 | Ford et al. |
| 7,483,756 B2 | 1/2009 | Engleson et al. |
| 7,483,839 B2 | 1/2009 | Mayaud |
| 7,487,101 B1 | 2/2009 | Vasko et al. |
| 7,509,280 B1 | 3/2009 | Haudenschild |
| 7,516,192 B2 | 4/2009 | Brown |
| 7,519,540 B2 | 4/2009 | Mayaud |
| 7,533,171 B2 | 5/2009 | Brown |
| 7,536,309 B1 | 5/2009 | Vasko et al. |
| 7,571,208 B2 | 8/2009 | Syed et al. |
| 7,574,370 B2 | 8/2009 | Mayaud |
| 7,606,620 B2 | 10/2009 | Gilkerson et al. |
| 7,608,042 B2 * | 10/2009 | Goldberger et al. ......... 600/366 |
| 7,624,028 B1 | 11/2009 | Brown |
| 7,630,773 B2 | 12/2009 | Seeberger et al. |
| 7,647,237 B2 | 1/2010 | Malave et al. |
| 7,678,071 B2 | 3/2010 | Lebel et al. |
| 7,694,273 B2 | 4/2010 | Kodosky et al. |
| 7,698,156 B2 | 4/2010 | Martucci et al. |
| 8,874,383 B2 * | 10/2014 | Gambier ............... F04B 49/065 340/572.1 |
| 2002/0038392 A1 | 3/2002 | De La Huerga |
| 2002/0081559 A1 | 6/2002 | Brown et al. |
| 2002/0092006 A1 | 7/2002 | Takeo |
| 2002/0169864 A1 | 11/2002 | Sesek |
| 2002/0173991 A1 | 11/2002 | Avitall |
| 2003/0004751 A1 | 1/2003 | Ng et al. |
| 2003/0040938 A1 | 2/2003 | Ng et al. |
| 2003/0069480 A1 | 4/2003 | Ng et al. |
| 2003/0069753 A1 | 4/2003 | Brown |
| 2003/0078805 A1 | 4/2003 | Ng et al. |
| 2003/0078808 A1 | 4/2003 | Ng et al. |
| 2003/0078812 A1 | 4/2003 | Uchikubo |
| 2003/0140929 A1 | 7/2003 | Wilkes et al. |
| 2003/0200114 A1 | 10/2003 | Ogino et al. |
| 2003/0212579 A1 | 11/2003 | Brown et al. |
| 2003/0216624 A1 | 11/2003 | Lin et al. |
| 2004/0019259 A1 | 1/2004 | Brown et al. |
| 2004/0024662 A1 * | 2/2004 | Gray et al. ............... 705/29 |
| 2004/0055611 A1 | 3/2004 | Penny et al. |

(56) References Cited

U.S. PATENT DOCUMENTS

| | | |
|---|---|---|
| 2004/0059202 A1 | 3/2004 | Mori |
| 2004/0073276 A1* | 4/2004 | Samuelsson ............... 607/60 |
| 2004/0088403 A1 | 5/2004 | Aggarwal |
| 2004/0122353 A1 | 6/2004 | Shahmirian et al. |
| 2004/0172284 A1 | 9/2004 | Sullivan et al. |
| 2004/0193453 A1 | 9/2004 | Butterfield et al. |
| 2004/0236606 A1 | 11/2004 | Oishi et al. |
| 2005/0010269 A1 | 1/2005 | Lebel et al. |
| 2005/0038326 A1 | 2/2005 | Mathur |
| 2005/0055242 A1 | 3/2005 | Bello et al. |
| 2005/0102167 A1 | 5/2005 | Kapoor |
| 2005/0108057 A1 | 5/2005 | Cohen et al. |
| 2005/0114170 A1 | 5/2005 | Park et al. |
| 2005/0137653 A1 | 6/2005 | Friedman et al. |
| 2005/0144204 A1* | 6/2005 | Lee et al. ............... 708/200 |
| 2005/0154612 A1 | 7/2005 | Smith et al. |
| 2005/0159982 A1 | 7/2005 | Showalter et al. |
| 2005/0187789 A1 | 8/2005 | Hatlestad et al. |
| 2005/0188083 A1 | 8/2005 | Biondi et al. |
| 2005/0207658 A1 | 9/2005 | Schofield |
| 2005/0228695 A1 | 10/2005 | Ito |
| 2006/0004611 A1 | 1/2006 | Brown |
| 2006/0010014 A1 | 1/2006 | Brown |
| 2006/0026205 A1* | 2/2006 | Butterfield ............... 707/104.1 |
| 2006/0036555 A1 | 2/2006 | Beck et al. |
| 2006/0059168 A1 | 3/2006 | Hamada |
| 2006/0064318 A1 | 3/2006 | Alsafadi et al. |
| 2006/0064465 A1* | 3/2006 | Fuerst ............... 709/214 |
| 2006/0089542 A1 | 4/2006 | Sands |
| 2006/0100746 A1* | 5/2006 | Leibner-Druska ............ 700/282 |
| 2006/0116639 A1 | 6/2006 | Russell |
| 2006/0229551 A1 | 10/2006 | Martinez et al. |
| 2006/0247979 A1 | 11/2006 | Brown |
| 2006/0248465 A1* | 11/2006 | Ryu et al. ............... 715/739 |
| 2006/0253300 A1 | 11/2006 | Somberg et al. |
| 2006/0259201 A1 | 11/2006 | Brown |
| 2006/0271404 A1 | 11/2006 | Brown |
| 2006/0285660 A1 | 12/2006 | Brown |
| 2006/0294212 A1 | 12/2006 | Kikkawa et al. |
| 2007/0061167 A1 | 3/2007 | Brown |
| 2007/0141711 A1 | 6/2007 | Stephens et al. |
| 2007/0156457 A1 | 7/2007 | Brown |
| 2007/0156892 A1 | 7/2007 | Brown |
| 2007/0168242 A1 | 7/2007 | Brown |
| 2007/0196909 A1 | 8/2007 | Showalter et al. |
| 2007/0208598 A1 | 9/2007 | McGrady et al. |
| 2007/0213598 A1 | 9/2007 | Howard et al. |
| 2007/0213603 A1 | 9/2007 | Brown |
| 2007/0213604 A1 | 9/2007 | Brown |
| 2007/0213605 A1 | 9/2007 | Brown |
| 2007/0213658 A1 | 9/2007 | Hickle |
| 2007/0233521 A1* | 10/2007 | Wehba ............... A61M 5/142 705/3 |
| 2007/0244997 A1 | 10/2007 | Tindal |
| 2008/0021379 A1 | 1/2008 | Hickle |
| 2008/0033767 A1 | 2/2008 | Brown |
| 2008/0097180 A1 | 4/2008 | Brown |
| 2008/0097181 A1 | 4/2008 | Brown |
| 2008/0103377 A1 | 5/2008 | Brown |
| 2008/0103379 A1 | 5/2008 | Brown |
| 2008/0103380 A1 | 5/2008 | Brown |
| 2008/0109172 A1 | 5/2008 | Brown |
| 2008/0109197 A1 | 5/2008 | Brown |
| 2008/0167900 A1 | 7/2008 | Ranchod |
| 2008/0200771 A1 | 8/2008 | Brown |
| 2008/0201168 A1 | 8/2008 | Brown |
| 2008/0287749 A1 | 11/2008 | Reuter |
| 2008/0306437 A1 | 12/2008 | Jacobson et al. |
| 2008/0312512 A1 | 12/2008 | Brukalo et al. |
| 2008/0312584 A1 | 12/2008 | Montgomery et al. |
| 2008/0314973 A1 | 12/2008 | Zuhars et al. |
| 2008/0320560 A1 | 12/2008 | Casey et al. |
| 2009/0150484 A1 | 6/2009 | Roberts |
| 2009/0156991 A1 | 6/2009 | Roberts |
| 2009/0210033 A1 | 8/2009 | Crivelli et al. |
| 2009/0222283 A1 | 9/2009 | Lassetter et al. |
| 2009/0243833 A1 | 10/2009 | Huang et al. |
| 2009/0265316 A1 | 10/2009 | Poulin et al. |
| 2009/0276237 A1 | 11/2009 | Jokinen et al. |
| 2009/0300507 A1 | 12/2009 | Raghavan et al. |
| 2010/0292645 A1* | 11/2010 | Hungerford ............ A61M 5/142 604/151 |

\* cited by examiner

```
┌─────────────────────────────┐
│ ◇   Control      Control    │
│  E  Id           string     │
│  E  Timestamp    dateTime   │
│  E  Response     boolean    │
│ ◇A                          │
├─────────────────────────────┤
│                             │
└─────────────────────────────┘
```
1200    Fig. 12

```
┌─────────────────────────────┐
│ ◇   Patient      Patient    │
│  E  Id           string     │
│  E  Name         string     │
│ ◇A                          │
├─────────────────────────────┤
│                             │
└─────────────────────────────┘
```
1300    Fig. 13

```
┌─────────────────────────────┐
│ ◇   Location     Location   │
│  E  Alias        string     │
│  E  Description  string     │
│ ◇A                          │
├─────────────────────────────┤
│                             │
└─────────────────────────────┘
```
1400    Fig. 14

```
┌─────────────────────────────┐
│ ◇   Drug         Drug       │
│  E  Id           string     │
│  E  Name         string     │
│  E  Concentration string    │
│ ◇A                          │
├─────────────────────────────┤
│                             │
└─────────────────────────────┘
```
1500    Fig. 15

```
┌─────────────────────────────┐
│ ◆   User         User       │
│  E  Id           string     │
│  E  Name         string     │
│ ◇A                          │
├─────────────────────────────┤
│                             │
└─────────────────────────────┘
```
1600    Fig. 16

Administration Tracking Event Report

Time Zone: Local
Time Periods [GMT]: All
Codes: All
Applications: All          3802

| Date | Time | Code | Application | Message |
|---|---|---|---|---|
| 12/14/2006 | 06:44:13 PM | AT001 | MDS:Mds01 | Connection accepted from 192.168.1.1 |
| 12/14/2006 | 06:46:22 PM | AT001 | MDS:Mds02 | Connection accepted from 192.168.1.2 |
| 12/14/2006 | 06:46:31 PM | AT002 | MDS:Mds01 | Connection with 192.168.1.1 closed |
| 12/14/2006 | 06:46:44 PM | AT041 | MDS:Mds02 | Response transmission failed, socket closed |
| 12/14/2006 | 06:46:58 PM | AT002 | MDS:Mds02 | Connection with 192.168.1.2 closed |

3804    3806

Administration Tracking Event Report
Page 1 of 10

Time Zone: Local
12/20/2006 01:26 PM

Security Event Report

Time Zone: Local
Time Periods [GMT]: All
Codes: All
Applications: All    3902

| Date | Time | Code | Application | Message |
|---|---|---|---|---|
| 12/14/2006 | 06:44:13 PM | AT032 | Mds01 | Connection from unknown medical device type |
| 12/14/2006 | 06:46:22 PM | AT043 | AdminWs | 'absmart' failed to login |
| 12/14/2006 | 06:46:31 PM | AT043 | AdminWs | 'absmart' failed to login |
| 12/14/2006 | 06:46:44 PM | AT044 | AdminWs | Lock user 'absmart' login attempted |
| 12/14/2006 | 06:46:58 PM | AT047 | AdminWs | 'absmart' access an unauthorized resource |

Security Event Report
Page 1 of 10

Time Zone: Local
12/20/2006 01:26 PM

User History Report

Time Zone: Local
Time Periods [GMT]: All
Codes: All
Users: All

| Date | Time | Code | User | Message | Details |
|---|---|---|---|---|---|
| 12/14/2006 | 06:44:13 PM | HC001 | medusr01 | User logged in from 'ws 001' | Session Key: 0kdoewkpi2309<br>Location: ws001 |
| 12/14/2006 | 06:46:22 PM | HC001 | medusr02 | User logged in from 'ws 002' | Session Key: Fsjie7834jkdui<br>Location: ws002 |
| 12/14/2006 | 06:46:31 PM | HC101 | medusr01 | Security role 'biomed' created | Name: biomed<br>State: 'EN' |
| 12/14/2006 | 06:48:12 PM | HC101 | medusr01 | Security role 'biomed' modified | New Members: medusr03, medusr04, medusr05 |
| 12/14/2006 | 06:48:40 PM | HC002 | medusr01 | User logged out | |
| 12/14/2006 | 08:12:22 PM | HC002 | medusr02 | User logged out | |

User History Report
Page 1 of 3

Time Zone: Local
12/20/2006 01:26 PM

Fig. 41

| | Search |
|---|---|

Package Information
PackageDeploymentId    c8416b0d-0164-444f-9c00-39a7b36ae54e
StartTime              1/11/2007 10:30:00 AM
EndTime                1/11/2007 11:15:00 AM
TargetTypeId           82bc6390-a340-45c6-93e6-03b04fde1f83

Vendor Properties
Id       c8416b0d-0164-444f-9c00-39a7b36ae54e
Name     Simple Infusion Pump
Version  0x00010000

Quarantine Report

Time Zone: Local
Date Range: 12/01/2006 – 12/11/2006
State: All

4702 4704 4706

| Date ○ | Time | State | Message |
|---|---|---|---|
| 12/01/2006 | 01:11:11 AM | New | Soap Message error Input string was not in a correct format . Couldn't store <40.0%> in Capacity Column.. Expected type is Single. |
| 12/01/2006 | 02:01:31 AM | New | Unknown medical device metadata . |
| 12/11/2006 | 07:09:11 PM | Released | Message validation method error |
| 12/11/2006 | 07:09:11 PM | Reinserted | Soap Message error System.Web.Services.Protocols.SoapException: E10070 at WebServices.Administration.Metadata.GetMetadata (Guid MetadataId, String identity) in D:\Projects\InformaticsSystem\WebServices\WebServices.Administration\Metadata.cs:line 226 at Administration.GetMetadata (Guid metadataId , String identity) |

Quarantine Report
Page 1 of 1

Time Zone: Local
12/31/2006 01:26 PM

Quarantine Detail Report

Timestamp : 1/1/1900 12:00:16 AM

Message Id : 3ab33e37-2e82-4fb4-b09b-094f2c31b576    4802

State : New

Message : Soap Message error Input string was not in a correct format . Couldn't store <40.0%> in Capacity Column. Expected type is Single.

SourceXml :
```
<?xml version="1.0"?>
<env:Envelope xmlns:env="http://schemas.xmlsoap.org/soap/envelope/" xmlns:xsi="http://www.w3.org/1999/XMLSchema-instance" xmlns:xsd="http://www.w3.org/1999/XMLSchema">
  <env:Header>
    <mds-hdr:Control xmlns:mds-hdr="mds:xml-schema:soap11-hdr">
      <Id>0</Id>
      <Timestamp>1900-01-01T00:00:05</Timestamp>
      <Response>false</Response>
    </mds-hdr:Control>
    <mds-hdr:Identity xmlns:mds-hdr="mds:xml-schema:soap11-hdr">        4804
      <TypeId>82E9495E-EEC3-424e-81B9-C02204B2CAB5</TypeId>
      <DeviceId>00:11:22:33:44:55</DeviceId>
      <SessionId>
      <NetworkId>
        <HostName>
        <HostName>
        <Domain>medical.smgpplc.com.</Domain>
        <Ip>10.3.113.10</Ip>
        <Port>1594</Port>
      </NetworkId>
      <Packages>
      </Packages>
    </mds-hdr:Identity>
  </env:Header>
  <env:Body>
  </env:Body>
</env:Envelope>
```

Quarantine Report
Page 1 of 1

Time Zone: Local
12/31/2006 01:26 PM

Package Deployment Report

Time Zone : Local
Packages: All
Medical Device Types: All

Medfusion 4000 — V1.1.0 Firmware Deployment [FD9273A8-17DC-437f-B596-21C75B0AB005] ←—4902
Name: 4906 Head Firmware 4908
Version: V1.1.0

| Host Name ○ | Physical Id | Notification | Transfer | Complete |
|---|---|---|---|---|
| MD001 | 01-02-03-0A-0B-0C | 12/14/2006 01:22:13 PM | 12/14/2006 01:22:44 PM | 12/14/2006 01:33:18 PM —4904 |
| MD002 | 01-02-03-0D-0E-0F | 12/14/2006 06:44:13 PM | 12/14/2006 06:45:26 PM | 12/14/2006 08:18:06 PM —4904 |
| MD003 | 01-02-03-1A-C3-11 | - | - | ——4904 |

4914 (bracket for Complete column)

Titan – C01 Configuration Deployment [2995D35A-1BF3-438a-A0E4-35E1F99EDAF3]
Name: 4906 Main Firmware 4908
Version: V2.0.0

| Host Name ○ | Physical Id | Notification | Transfer | Complete |
|---|---|---|---|---|
| T0132 | 0C-08-01-01-0F-03 | 12/14/2006 01:22:13 PM | 12/14/2006 01:22:44 PM | 12/14/2006 01:33:18 PM —4904 |
| T0023 | 0C-08-01-06-07-21 | 12/14/2006 06:44:13 PM | - | ——4904 |

ERROR: Package transfer failed , medical device closed connection . ←—4916

| T1765 | 0C-08-01-81-16-02 |  | 12/14/2006 06:45:26 PM | 12/14/2006 08:18:06 PM —4904 |

4914 (bracket for Complete column)

Package Deployment Report
Page 1 of 10

Time Zone : Local
12/20/2006 01:26 PM

Package Deployment Error Report

Time Zone: Local
Packages: All
Medical Device Types: All

Titan – C01 Configuration Deployment [2995D35A-1BF3-438a-A0E4-35E1F99EDAF3] ← 5002
Name: 5004 Main Firmware
Version: V2.0.0

| Date | Time | Host Name 5006 | Physical Id 5008 | Message 5010 |
|---|---|---|---|---|
| 12/14/2006 | 06:44:13 PM | T0023 | 0C-08-01-06-07-21 | Package transfer failed, medical device closed connection. |

Package Deployment Error Report
Page 1 of 10

Time Zone: Local
12/20/2006 01:26 PM

Medical Device Maintenance Report

Time Zone: Local
Medical Devices: All
PM Periods: All

Medfusion 4000

| Host Name | Physical Id | Version(s) | Package(s) | PM Date |
|---|---|---|---|---|
| MD001 | 01-02-03-0A-0B-0C | 1.0.1<br>1.0.0 | FD9273A8-17DC-437f-B596-21C75B0AB005<br>2995D35A-1BF3-438a-A0E4-35E1F99EDAF3<br>904CC230-E26E-4846-A4E3-89F622CD8DA2 | 12/14/2007 |
| MD002 | 01-02-03-0D-0E-0F | 1.0.1<br>1.0.0 | FD9273A8-17DC-437f-B596-21C75B0AB005<br>2995D35A-1BF3-438a-A0E4-35E1F99EDAF3<br>904CC230-E26E-4846-A4E3-89F622CD8DA2 | 12/14/2007 |

Titan

| Host Name | Physical Id | Version(s) | Package(s) | PM Date |
|---|---|---|---|---|
| T0132 | 0C-08-01-01-0F-03 | 1.1.0 | FD9273A8-17DC-437f-B596-21C75B0AB005<br>2995D35A-1BF3-438a-A0E4-35E1F99EDAF3 | 12/14/2007 |
| T0023 | 0C-08-01-06-07-21 | 1.1.0 | FD9273A8-17DC-437f-B596-21C75B0AB005<br>2995D35A-1BF3-438a-A0E4-35E1F99EDAF3 | 12/18/2007 |
| T1765 | 0C-08-01-81-16-02 | 1.1.0 | FD9273A8-17DC-437f-B596-21C75B0AB005<br>2995D35A-1BF3-438a-A0E4-35E1F99EDAF3 | 1/22/2007 |

Medical Device Maintenance Report
Page 1 of 10

Time Zone: Local
12/20/2006 01:26 PM

Fig. 51

Medical Device Fault Report

Time Zone: Local
Time Periods [GMT]: All
Medical Device Types: All

Medfusion 4000 — 5202

| Date | Time | Host Name | Physical Id | Message |
|---|---|---|---|---|
| 12/14/2006 | 06:44:13 PM | MD001 | 0C-08-01-06-07-21 | Motor rate error. |
| 12/14/2006 | 06:44:13 PM | MD002 | 0C-08-01-06-07-21 | Battery not working |

Medical Device Fault Report
Page 1 of 1

Time Zone: Local
12/20/2006 01:26 PM

Fig. 52

Medical Device History Report

Time Zone: Local
Time Periods [GMT]: All
Medical Devices: All

Medfusion 4000 — 5802

| Date | Time | Class | Trigger | Message | Location | Drugs |
|---|---|---|---|---|---|---|
| 5804 | | 5806 | 5808 | 5810 | 5812 | 5814 |

⊟ Physical Id: 0C-08-01-06-07-21
   Hostname: MD101

| Date | Time | Class | Trigger | Message | Location | Drugs |
|---|---|---|---|---|---|---|
| 12/01/2006 | 06:13:01 PM | Alarm<br>Level of Concern: Major | Warning | Battery Low<br>PVD 3.123<br>TVD 4.523<br>PlungerPosition 3.2<br>Force 5.3<br>SyringeDiameter 1.23<br>AnalogSupply 5.01<br>FailedValue 3.5 | ICU – Intensive Care Unit<br>Patient: P101<br>MD User: medusr01 | Lycopene<br>Code: LYC<br>Strength: 10 mg. |
| 12/11/2006 | 07:09:11 PM | Therapy Change<br>Parameter: Dose<br>Original Value: 5 mg.<br>Value Entered: 10 mg.<br>Final Value: 10 mg. | Override | Infusing<br>UpperHardLimit 100.00<br>UpperSoftLimit 102.00<br>LowerSoftLimit 50.00<br>LowerHardLimit 48.00 | ICU – Intensive Care Unit<br>Patient: P101<br>MD User: medusr01 | |
| 12/01/2006 | 06:13:01 PM | Fault<br>Level of Concern: Major | On | Battery not working<br>PVD 3.123<br>TVD 6<br>PlungerPosition 3.2<br>Force 5.3<br>SyringeDiameter 1.23<br>AnalogSupply 5.01<br>FailedValue 3.5 | ICU – Intensive Care Unit<br>Patient: P101<br>MD User: medusr01 | |

– Physical Id: AC-11-01-45-76-00
   Hostname: MD1034

Therapy Change History Report

Time Zone: Local
Time Periods [GMT]: All
Medical Devices: All  ← 6102

Medfusion 4000
6104 → Physical Id: 0C-08-01-06-07-21

| Date | Time | Event Class | Event Trigger | Message | Location | Drugs |
|---|---|---|---|---|---|---|
| 12/01/2006 | 01:11:11 AM | Therapy | Begin | Therapy begin. | ICU – Intensive Care Unit<br>Patient: P101<br>MD User: medusr01 | Dyrexetrene<br>Code: DYR<br>Strength: 100 mg. |
| 12/01/2006 | 02:01:31 AM | Therapy | End | Therapy end. | ICU – Intensive Care Unit<br>Patient: P101<br>MD User: medusr01 | Dyrexetrene<br>Code: DYR<br>Strength: 100 mg. |
| 12/11/2006 | 07:09:11 PM | Therapy | Begin | Therapy begin. | ICU – Intensive Care Unit<br>Patient: P101<br>MD User: medusr01 | Lycopene<br>Code: LYC<br>Strength: 10 mg. |
| 12/11/2006 | 07:09:11 PM | Therapy Change<br>Parameter: Dose<br>Original Value: 5 mg.<br>Value Entered: 10 mg.<br>Final Value: 10 mg. | Override | Infusing | ICU – Intensive Care Unit<br>Patient: P101<br>MD User: medusr01 | Lycopene<br>Code: LYC<br>Strength: 10 mg. |

Columns labeled: 6106, 6108, 6110, 6112, 6114

| Medical Devices | | | | | |
|---|---|---|---|---|---|
| 6702 | 6704 | 6706 | 6708 | 6710 | 6712  Search |
| Hostname | Physical Id | Domain | IP Address | Port | Last Activity |
| MD0333 | AX-06-29-00-12-03 | MEDICAL | 192.168.1.1 | 1587 | 12/11/2006 12:02:03 PM |
| MD0444 | QX-06-29-13-12-BV | MEDICAL | 192.168.1.2 | 1587 | 12/11/2006 3:11:03 PM |
| MD0524 | SA-11-29-13-12-22 | MEDICAL | 192.168.1.3 | 1587 | 12/11/2006 4:23:11 PM |
| MD0324 | SA-21-29-22-12-80 | MEDICAL | 192.168.1.11 | 1587 | 12/10/2006 6:01:39 PM |
| MD0988 | AA-13-29-22-41-99 | MEDICAL | 192.168.2.2 | 1587 | 12/11/2006 10:11:28 AM |

Legend
- [ ] Alarm Status
- [ ] Fault Status
- [ ] Powered Status
- [ ] Therapy Status Last Update : 03:44:18 pm
- 6714 — [ ] Pause Updates
- 6716 — [✓] Show Offline Medical Devices

COMMUNICATION OF ORIGINAL AND UPDATED PUMP PARAMETERS FOR A MEDICAL INFUSION PUMP

CROSS-REFERENCE TO RELATED APPLICATIONS

The present application claims priority to U.S. Provisional Patent Application No. 60/964,444, entitled "Patient Treatment Systems Employing Medical Device Informatics", and filed Aug. 10, 2007. That application is hereby incorporated by reference in its entirety.

TECHNICAL FIELD

In general, the present disclosure relates to treatment of patients via systems for use and control of medical devices. More specifically, the present disclosure relates to software for treatment of patients using medical devices.

BACKGROUND

Patients at hospitals and other care centers require controlled therapy administration and monitoring. Hospitals and care centers use a variety of types and brands of medical devices to assist in monitoring and therapy administration. For example, medical devices used to assist in therapy administration may include medical infusion pumps, pulse oximeters, cardiopulmonary monitors, and other therapy delivery and patient monitoring equipment. The various types and brands of medical devices each generally use differing, proprietary communication standards.

The proprietary standards employed by the different devices limit interoperability among the devices, making therapy administration difficult. During use of one or more of the medical devices, a caregiver may want to perform a number of actions related to the medical device. For example, a caregiver may wish to set parameters in a medical device based on the observed characteristics of the patient. Or, the caregiver may wish to view data gathered by a monitor. Due to the proprietary standards used by various medical devices, the caregiver may use a number of types of software and hardware to access the information gathered by the medical device needed to treat the patient.

Coordinating usage of medical devices also can be difficult. A single medical device can be programmed for administering different therapies and in different locations within a hospital. Usage records of multiple medical devices of varying types and in different hospitals may need to be compared. Similarly, the status of a medical device can be difficult to monitor because the devices are often in locations other than where the caregiver is located.

SUMMARY

Methods and systems of patient treatment are disclosed. The methods and systems include use of medical device informatics to modify and validate therapies and drugs used in those therapies. In the various aspects of the present disclosure, a medical device, such as a medical infusion pump, interfaces with a server to administer treatments to patients.

In certain aspects, medical device metadata is used to define a medical device within a medical device network. In further aspects, messages are communicated between a medical device and server to define treatments and other operations to the medical device. In still other aspects, operational and historical data is communicated from medical devices to a medical device server to allow remote monitoring of the administration of a therapy to a patient. In further aspects, timing parameters dictate communication and tracking of events between a medical device and a medical device server.

In a particular aspect, a method of tracking changed parameters in a medical infusion pump is disclosed. The method includes establishing a communication session between a medical infusion pump and a medical device server, and communicating an original parameter value, an updated parameter value, and a final parameter value from the medical infusion pump to the medical device server. The method further includes storing the original parameter value, the updated parameter value, and the final parameter value on the medical device server. Metadata associated with one or more of the parameter values identifies that parameter value to the medical device server and the medical infusion pump.

In a second aspect, a system for tracking changed parameters in a medical infusion pump is disclosed. The system includes a medical infusion pump having one or more programmable parameters and a medical device server communicatively connected to the medical infusion pump. The medical device server includes a memory configured to store parameter values and a programmable circuit operatively connected to the memory. The programmable circuit is configured to execute program instructions to establish a communication session between the medical infusion pump and the medical device server, and receive an original parameter value, an updated parameter value, and a final parameter value from the medical infusion pump. The programmable circuit is also configured to execute program instructions to store the original parameter value, the updated parameter value, and the final parameter value in the memory. Metadata associated with one or more of the parameter values identifies that parameter value to the medical device server and the medical infusion pump.

In a third aspect, a system for tracking changed parameters in a medical infusion pump is disclosed. The system includes a plurality of medical infusion pumps, each of the pumps having one or more programmable parameters. The system also includes a medical device server communicatively connected to the plurality of medical infusion pumps. The medical device server includes a memory configured to store parameter values and a programmable circuit operatively connected to the memory. The programmable circuit is configured to execute program instructions to establish a communication session between one of the medical infusion pumps and the medical device server and receive an original parameter value, an updated parameter value, and a final parameter value from the medical infusion pump. The programmable circuit is also configured to execute program instructions to store the original parameter value, the updated parameter value, and the final parameter value in the memory. Metadata associated with one or more of the parameter values identifies that parameter value to the medical device server and the medical infusion pump.

BRIEF DESCRIPTION OF THE DRAWINGS

FIG. 11-16 are data models including metadata useable to facilitate extensible communication systems for medical devices and medical device servers;

FIG. 38 is a sample medical device administration event tracking report accessible from a medical device server;

FIG. 39 is a sample security event tracking report accessible from a medical device server;

FIG. 41 is a sample user history report accessible from a medical device server;

FIG. 46 is a user interface confirming deployment of a data packet to a medical device;

FIG. 47 is a sample quarantine report indicating erroneous data transmission from a medical device server to a medical device;

FIG. 48 is a sample detailed quarantine report, corresponding to the quarantine report of FIG. 47;

FIG. 49 is a sample package deployment report displaying deployments of data packets from a medical device server to medical devices;

FIG. 50 is a sample package deployment error report displaying erroneous deployments of data packets from a medical device server to medical devices;

FIG. 51 is a sample maintenance report displaying medical device maintenance events;

FIG. 52 is a sample medical device fault report displaying medical device faults communicated to a medical device server;

FIG. 58 is a sample medical device history report displaying event log data communicated from a medical device to a medical device server;

FIG. 61 is a sample therapy change history report displaying changes to therapies in therapy event log data communicated from a medical device to a medical device server;

FIG. 67 is an example dashboard useable to display telemetry data related to one or more medical devices.

DETAILED DESCRIPTION

Figure 1:
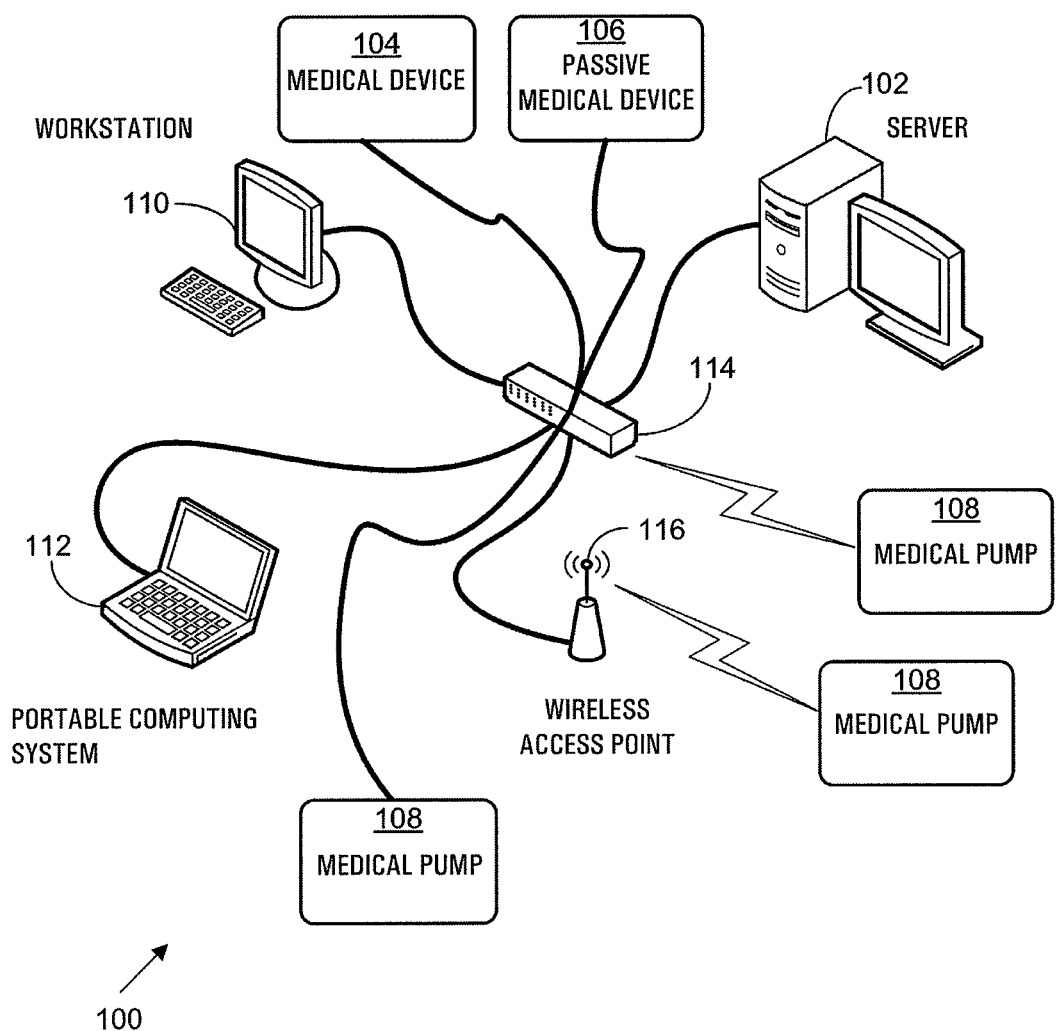
FIG. 1 shows an exemplary medical device network in which aspects of the present disclosure may be implemented.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto.

Additionally, any examples set forth in this specification are not intended to be limiting and merely set forth some of the many possible embodiments for the claimed invention.

The logical operations of the various embodiments of the invention described herein are implemented as: (1) a sequence of computer implemented steps, operations, or procedures running on a programmable circuit within a computer, (2) a sequence of computer implemented steps, operations, or procedures running on a programmable circuit within a medical device; and/or (3) interconnected machine modules or program engines within the programmable circuits.

The description set forth herein discusses use and programming of a variety of medical devices and a medical device server in a medical device network. One skilled in the art will realize that a wide variety of medical devices are used in administering a therapy to a user, such as medical infusion pumps, pulse oximeters, cardiopulmonary monitors, and other therapy delivery and patient monitoring equipment. These and additional medical devices may be used in the medical device network of the present disclosure. In various aspects of the present disclosure, the term medical device server refers to a computing system and a message handling and storage service used for coordination of various other components of the system. Additionally, the term "user" in the context of the medical device generally applies to the person who is receiving a therapy. In many other contexts, such as the context of usage of the medical device server, the user could also refer to any other person such as a caregiver that is operating the medical device or a computer with access to information about the medical device.

Additionally, the medical devices and interconnected computing systems considered in the present disclosure generate and present information and fields in user interfaces and reports, which are also referred to as displays. The user interfaces and reports can include fields, alpha/numeric character strings, times, and dates. The fields, also referred to as cells, prompt users to enter and/or select information. Various types of input and display devices are available on various computing systems and medical devices.

The various types of medical devices encompassed by the present disclosure execute or utilize operating parameters, which customize or personalize operation of computer implemented steps, machine modules, and programs to meet the requirements of individual medical device users. The operating parameters can be numerical values, text strings, flags, argument names, or any other aspect of medical device programming that the user or a caregiver can set to control operation of the medical device. In certain aspects of the present disclosure, metadata indicates a textual definition of the capabilities of the various operating parameters within the medical device, and to servers and other computing systems interfaced with the medical device.

I. Hardware Environment

Figure 2:
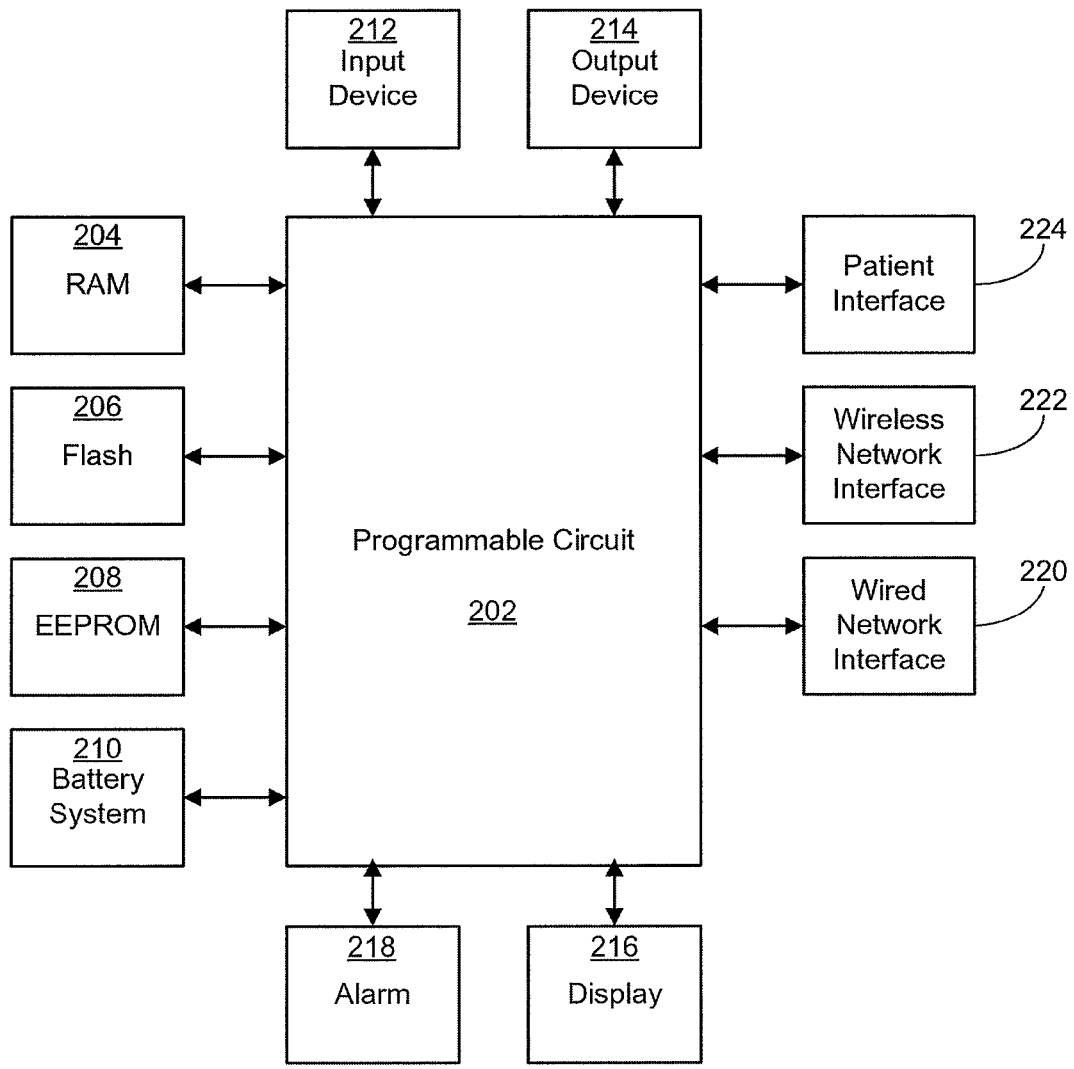
FIG. 2 is a block diagram of a medical device useable in aspects of the present disclosure.

Referring generally to FIGS. 1 and 2, a generalized hardware environment is described. FIG. 1 shows an exemplary medical device network 100 in which aspects of the present disclosure may be implemented. The medical device network 100 provides a method by which a variety of medical devices and communication systems intercommunicate. The medical device network 100 includes a medical device server 102 interconnected with a variety of types of medical devices. The medical devices can include an active medical device 104, a passive medical device 106, and a plurality of exemplary medical devices shown to be medical infusion pumps 108.

The active medical device 104 refers to any of a number of medical devices configured to assist in administering a therapy to a patient. Active medical devices include medical infusion pumps for delivery of fluidic therapies, or other therapy-providing equipment. In one embodiment, the active medical device 104 is a medical infusion device, such as the medical infusion pumps 108 shown.

The passive medical device 106 refers to any of a number of observation devices configured to monitor the status of a patient, rather than to actively assist in administering a therapy to that patient. Examples of passive medical devices include pulse oximeters, cardiopulmonary monitors, or other patient observation systems for measuring vital signs of the patient, such as breathing, heart rate and rhythm, blood oxygen levels, and other health indicators.

The medical device server 102 communicates with the medical devices, and is one or more generalized or application-specific computing systems. The medical device server 102 is configured to store and retrieve data received from the various medical devices 104, 106, 108. The data received by the medical device server 102 can include event log data, programming data, and various other data transmitted to the server 102 from the medical devices 104, 106, 108.

Optionally, the medical device network 100 includes additional computing devices, such as workstations 110 and portable computing systems 112, configured to allow communicative connection to the medical device server 102. The workstations 110 and portable computing systems 112 are generalized computing systems or thin client computing systems having a communication interface allowing access to the medical device server. The workstations 110 and portable computing systems 112 generally include input devices and displays, so as to allow a user (i.e. a caregiver) access to data about a patient when that user is not in the same location as the patient. The users may access the medical device server 102 via the workstation 110 or portable computing system 112 to retrieve data gathered from a medical device, and may instruct the medical device server 102 to communicate various messages or software packages to one or more of the medical devices.

The medical device network 100 optionally includes network infrastructure components, such as a switch 114 and a wireless access point 116. The network infrastructure components are configured to provide the communication infrastructure between the various medical devices 104, 106, 108, the medical device server 102, and any additional computing systems 110, 112. Although the medical device network 100 requires a communicative conduit between the various components included in the network, the specific components included in a given medical device network will vary based upon the particular infrastructure and needs of users of the medical device network. Therefore, the switch 114 and wireless access point 116 are intended as exemplary components for implementation of a communicative interconnection between the various components of the network. Additional types of medical devices, computing systems, or networking components may be used in the network 100 as well.

The medical device server 102, as well as the additional computing system 110, 112, can correspond generally to a general purpose computing system configured to execute program instructions for performing a variety of operations in the medical device network. Example computing systems can include those constructed by a variety of computer manufacturers, such as Apple, Dell, International Business Machines, and the like. Such computing systems can include, for example, a general purpose or specifically-designed programmable circuit and operably connected memory device, and are configured to execute program instructions to execute the operations described herein.

The programmable circuit can be, for example any of a variety of processing units available from a variety of manufacturers, for example, Intel or Advanced Micro Devices. The computing system also typically includes a system memory that couples various system components including the system memory to the processing unit. A display device can be used to display the user interfaces, as processed by the memory and programmable circuit. The display device can be a touch screen or other type of display. Other peripheral devices can be included in the computing system as well.

The computing system can operate based on instructions stored on computer storage media, communication media, or other means of encoding computer instructions. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the computing system.

Communication media typically embodies computer-readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

FIG. 2 shows an exemplary block diagram of a medical device 200. The medical device 200 is any of a number of types of active or passive medical devices for therapy administration or monitoring of a patient. In one possible embodiment, the medical device 200 is a medical infusion pump configured to infuse drugs and other fluidic therapies to a patient. Other types of medical devices are possible as well.

The medical device 200 includes a programmable circuit 202 interfaced to a memory subsystem, including, for example, Random Access Memory (RAM) 204, a flash memory 206, and an electrically erasable, programmable memory (EEPROM) 208. The RAM 204 stores operational parameters of the medical device, as well as any non-critical storage with respect to operational data or instructions. The flash memory 206 stores instruction and/or data memory defining operation of the pump, such as pump programs, pump parameters for use in those pump programs, or other system firmware. The EEPROM 208 stores a set of initial instructions that are used by the medical device 200 and must be preserved in the event of a failure of the device, such as due to a power failure, dead battery, or other unanticipated event. The EEPROM 208 optionally includes firmware or instructions which may be read or copied into the RAM 204 or flash memory 206 for execution, as necessary.

In various embodiments of the medical device 200, the various components of the memory subsystem used are dictated by the needs of the medical device. In certain devices, one or more of the memory system components described herein are not present. In such devices, some or all of the data and instructions stored in that device may be stored in another component of the memory subsystem present in the device. RAM may also temporarily provide storage for critical operational data or instructions. Also, alternate embodiments can be provided whereby the contents of the flash memory and the contents of the EEPROM memory previously described may be interchanged, or whereby the contents may be entirely stored in one type of non-volatile memory and none in the other. Finally, other types of non-volatile memory may be used instead, such as ferro-electric memory or others.

The medical device 200 further includes a battery system 210 configured to provide a direct current source of power to the medical device when the device cannot be plugged in to a wall power outlet or some other AC power source. In one embodiment, the battery system 210 includes a rechargeable lithium-ion smart battery system configured to provide power management and intelligent switching between DC and AC power modes depending on the presence of AC power. In further embodiments, the battery system 210 includes different types of battery systems, such as a rechargeable battery system including a nickel-cadmium battery.

The medical device 200 includes an input device 212 and an output device 214 interfaced to the programmable circuit 202. The input device 212 allows a user at the location of the medical device to adjust the activity of the device. The input device 212 can be, for example, a mouse, keyboard, keypad, trackball, touch screen, control buttons, or other user-controllable devices. The output device 214 can be any type of audio, video, or data interface configured to provide information regarding the medical device to users and devices external to the device. In various embodiments, the output device 214 may be a data interface to a second medical device, or may be a connection to an external monitor for display of information to a user regarding the status of the medical device 200.

The medical device 200 also includes a display device 216 and an alarm 218. The display device 216 is a visual device capable of displaying information to a user of the device. In various embodiments of the medical device 200, the display device 216 can be, for example, a display device, such as an LCD, CRT, or other screen. Additional types of display devices are possible as well. Furthermore, although the medical device is shown as including a display device 216, in alternate embodiments a display device is not required. The alarm 218 can be configured to provide various types of audio indications to the user of various conditions detected in the user or the device. These conditions include a health condition detected, such as an abnormally low or high heart rate or respiration rate, or a warning related to the device, such as indicating that a supply of a drug is running low, or that maintenance may be required for the device. The alarm optionally triggers based on additional alarm conditions beyond those listed here; the alarms selected generally relate to the type of medical device implemented and conditions experienced by that device.

A wired communication interface 220 provides a data communication connection from the medical device 200 that interfaces with a medical device server or other generalized computing system. The wired communication interface 220 interfaces to the programmable circuit 202, and sends and receives data from the medical device 200. In various embodiments, the wired communication interface 220 can be an Ethernet or other data connection capable of communicating and receiving digital data.

A wireless communication interface 222 provides an alternative communication interface to the wired communication interface 220, such that the medical device 200 can maintain data communications with a medical device server or other computing system when a wired communication connection is not available or convenient, based on the location of the medical device. The wireless communication interface 222 interfaces to the programmable circuit 202, and sends and receives data wirelessly from the medical device. Usage of one or both of the wired or wireless communication interfaces is dependent upon the location of the medical device and the need for communication with a medical device server. In one embodiment, the medical device provides a constant data stream to one or both interfaces such that individuals with access to a medical device server can continuously track the status of the medical device. In further embodiments, the medical device activates and/or communicates using one or both interfaces periodically, or intermittently, so as to update the operational data or other information held by either the medical device or the medical device server.

The medical device 200 also includes a patient interface 224. The patient interface 224 controls the mechanical component of the medical device 200 which monitors or delivers a therapy to the user. The patient interface 224 varies among the different types of medical devices based upon the function of the device. In the case where the medical device 200 is a monitor, the patient interface 224 may include a sensor or other physical detection equipment. In the case where the medical device 200 is a medical infusion pump, the patient interface may include a drive mechanism, occlusion sensor, fluid volume sensor, or other drug control or delivery interfaces. Other medical devices, and corresponding patient interfaces, are possible as well. Additional components beyond those shown may also be included in various embodiments of the medical device 200, depending upon the particular application to which the device is directed.

II. Overall Software Environment

FIGS. 3-6 show an overall software environment for the medical device network 100 and its components, according to various embodiments of the present disclosure. The software environment disclosed herein is discussed in two sections: (1) those aspects which relate to communications between medical devices and a medical device server, found in part III, and (2) aspects encompassing user interaction with the medical device network, such as to view data related to medical device activity, or to administer changes or additions to the medical device network, found in part IV. Both aspects relate generally to coordination of medical devices in a medical device network, of which the primary physical features are described above in FIGS. 1-2.

The various software disclosed herein, including the metadata installation software, package deployment software, and server software described in Parts II-IV, below can be packaged in a variety of ways, and organized for a variety of different medical device networks. In a possible embodiment, the various software aspects are included in a software development kit (SDK) including some or all of the various software components described herein. In such an embodiment, the medical devices can include monitors and medical infusion pumps, and the software can include pre-packaged metadata files useable on both the medical devices and medical device server. User-readable documentation regarding the software can be included as well.

Additionally, the various software disclosed herein and claimed below can be embodied on any of a number of types of computing systems operable within the hardware environment of FIGS. 1-2. For example, a computing device typically includes at least some form of computer-readable media. Computer readable media can be any available media that can be accessed by the computing system. By way of example, and not limitation, computer-readable media might comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by a computing system.

Communication media typically embodies computer-readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Figure 3:
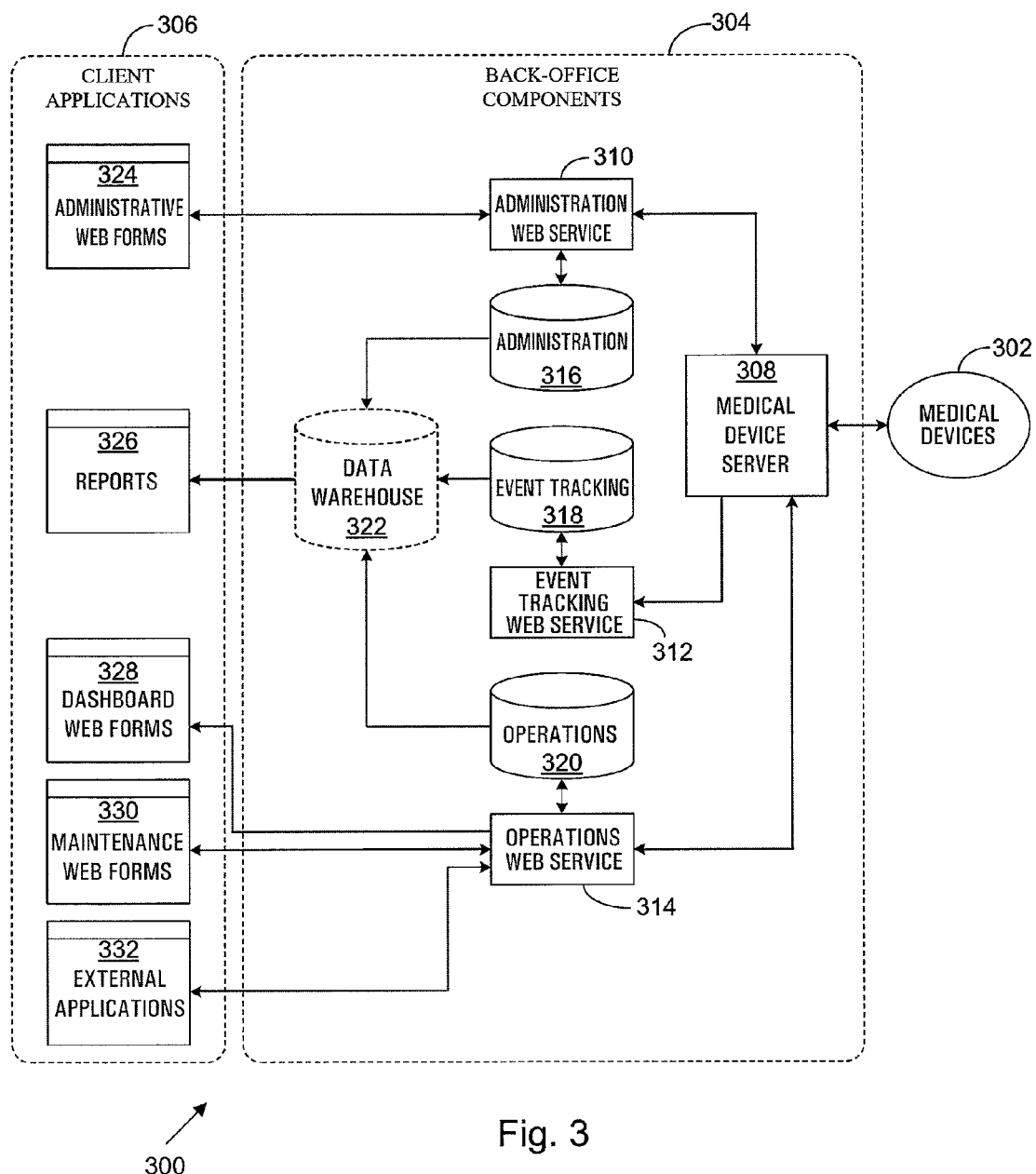
FIG. 3 is a diagram of a software architecture for a medical device network.

FIG. 3 shows a software architecture 300 in which aspects of the present disclosure are implemented. The software architecture 300 provides an operating environment in which medical device data can be stored and managed remotely from the medical devices. The software architecture 300 also provides an extensible architecture in which a variety of types of medical devices can operate. The software architecture 300 operates using one or more computing systems in communicative connection to various medical devices, and is configurable to operate across multiple locations and different business entities. The software architecture 300 operates within a medical device network including one or more medical devices and a medical device server. A possible configuration of the medical device network in which the software architecture operates is described above in FIG. 1.

In one embodiment, aspects of the software architecture 300 are implemented using the relational and business intelligence components of Microsoft SQL Server 2005, distributed by Microsoft Corporation. In such an embodiment, various modules, such as web interfaces, may be provided using a web service, such as Microsoft Internet Information Services (IIS) platform. In further possible embodiments, aspects of the system are implemented using Microsoft SQL Server 2000, Oracle, or other database management and business intelligence products, in conjunction with various web services, such as an Apache-based or other web server.

The software architecture 300 includes one or more medical devices 302, back office components 304, and client applications 306. The medical devices 302 monitor or deliver therapies to patients, as directed by a caregiver. The medical devices 302 can be any of a variety of programmable medical devices such as those discussed in conjunction with FIGS. 1-2, above.

The back office components 304 include one or more medical device servers 308, an administration module 310, an event tracking module 312, and an operations module 314. The medical device server 308 manages communication with the various medical devices 302 associated with the back office components 304, such as by relaying messages between the various modules 310, 312, 314 and the medical devices 302. The medical device server 302 creates messages understandable to the medical devices 302 and the various modules 310, 312, 314 such that a variety of types of medical devices can be managed using the modules. Using the messages sent to the medical devices 302, the medical device server 308 collects historical information from the medical devices, automates various maintenance operations, assists with therapy setup at a user's bedside, and provides medical device monitoring. In a possible embodiment, the medical device server 302 manages a metadata-based messaging system for communicating with a variety of types of medical devices, such as by using XML or some other type of metadata or markup language via SOAP or another messaging protocol.

In one possible embodiment, the medical device server 308 resides on a computing system which also hosts the additional back office components 304. In a further embodiment, the medical device server resides on separate computing hardware from the other back office components. In such systems, the medical device server 308 may be placed at a different location from the other back office components, or may be managed by a different entity from the other back office components, as is described in FIGS. 4-5, below. For simplicity, throughout the description of the software aspects the term medical device server is intended to encompass either the medical device server 308 or the back office components 304 as a whole, depending upon the specific implementation chosen. In certain embodiments, the medical device server 308 can be placed on one or more physical computing platforms, resulting in the presence of multiple medical device servers.

The administration module 310 provides an interface to administration data 316, which the medical device server 308 and client applications 306 can request for various reasons, such as to allow access to event or operational data, described below. The administration data 316 includes user validation information, such as username, password, IP authentication, or other user validation, as well as rights information defining the access rights associated with the user. For example, the administration data 316 may associate a username with a password, and require a user to provide the correct username and password to receive a validation right. The username and password information may in turn be associated with access rights information, which defines the specific categories of data, subsets of medical devices, or types of commands allowed to that user. Additional access rights may be defined in the administration data 316 and managed by the administration module 310 as well.

The administration data 316 also defines the capabilities of the various medical devices 302 managed within the environment 300, by defining operational parameters by which the medical device server 308 interfaces with a medical device 302. For example, a medical device configured to monitor a patient may include a variety of defined parameters relating to monitoring functions, but will not include parameters relating to therapy delivery. In allowing user-definition of a variety of possible medical device capabilities by setting operational parameters within the administration data, the environment 300 provides a user-extensible set of back office components which are configurable with a variety of medical devices having various capabilities, manufactured by different entities, and employed at different locations.

In a particular embodiment, the administration module 310 generates a web interface accessible to various client application interfaces to remotely validate users or caregivers wishing to access data held within one or more of the back office components 304. In a further embodiment, the administration module provides an interface allowing remote applications to access the data managed by the back office components 304.

The event tracking module 312 provides an interface to the medical device server 308, and organizes and manages event data 318. The event data 318 corresponds to the historical data regarding various events occurring in the medical devices 302, which are collected and routed by the medical device server 308. The event data 318 correlates a medical device identifier with an event identifier, and additional descriptive information regarding the event occurring in the medical device. Examples of events tracked using the event tracking module 312 include power events, alarm events, maintenance events, telemetry events, therapy events, or therapy change events in the various medical devices. Examples of various events and schema used for tracking such events are discussed below in conjunction with FIGS. 19-24. In a particular embodiment, the event tracking module 312 generates a web interface accessible by the medical device server 308 to transfer data to a storage location of event data 318.

The operations module 314 manages various operational characteristics of the system, such as system operational information, therapy orders, maintenance jobs, and other information used to affect operation of the various medical devices 302 associated with the environment 300. The operations module 314 also provides a web interface to the medical device server 308 for managing the various types of operations data 320, and to various external computing systems to allow those systems to view the operations data 320 and transmit commands within the software architecture 300, such as to the various medical devices 302.

An optional data warehouse 322 aggregates and coordinates the various predefined and collected data, including the administration data, the event data, and the operations data, for use by various client applications. In the embodiment shown, a reporting application receives data from the data warehouse 322, which aggregates various data from the administration data 316, the event data 318, and the operations data 320. The data warehouse 322 provides a convenient static repository useable to generate reports based on one or more of these types of data. Example reports are described in conjunction with the user to server communication systems described in Part IV, below. The data warehouse 322 can be formed using any of a number of relational or On-Line Analytical Processing products, such as SQL Server Analysis Services, Hyperion Essbase, Oracle OLAP, or other data store configured to allow querying or access to various combinations of data. For those embodiments without the optional data warehouse 322, its functionality as described herein can be provided by the Administration, Event Tracking, Operations databases and their corresponding modules, as described herein.

The client applications 306 generally access one or more of the data sources 316, 318, 320, 322 to generate user output forms indicating to caregivers or other users current or historical information about the medical devices to which that caregiver or user has access. The client applications 306 accessing the back end components 304 include administration applications 324, reporting applications 326, dashboards 328, maintenance forms 330, and various additional external applications 332.

The administration applications 324 provide user access to the administration data 316 include a variety of administration web forms, to define usage rights for other users attempting to access the back office components 304, as well as to define the operational parameters of the medical devices 302. Additional administration web forms may be included as well.

The reporting applications 326 provide a number of standardized reports based on the administration data 316, the event data 318, and the operation data 320. In an embodiment in which the back office components 304 include a data warehouse 322, the reports may be based on the information in the data warehouse. Examples of reports built using the various types of data tracked in the back office components 304 include security reports, user histories, software deployment reports, medical device programming reports, maintenance reports, device history reports, therapy reports, and other reports. Additional examples of the reports are described in Part IV, below.

The dashboards 328 allow a caregiver or user to view the status of a medical device 302. The dashboards 328 are based on operation data, and interface to the operations module 310. The dashboards 328 available within the environment 300 correspond to the various medical devices 302 capable of frequently transmitting data to the back office components 304. The dashboards 328 receive operational data regarding the medical devices, such as the most recent therapy delivered by the devices. This information is reflected on the dashboard user interface, presented on a display device of a computing system accessible to a caregiver or user. In one possible embodiment, the dashboards 328 replicate the visual interface of the corresponding medical device, but in a web-portal format.

The maintenance forms 330 display maintenance information to a caregiver or other user of the medical devices 302. The maintenance forms 330 display tracked maintenance information included in the operations data 320, such as performed maintenance, scheduled maintenance, suggested maintenance, and maintenance trends. The maintenance forms 330 also allow the user to deploy various updates to the medical devices 302, such as firmware updates and other software deployments. In a possible embodiment, the operations data 320 includes maintenance schedule information accessible by users via the maintenance forms. In such an embodiment, the maintenance forms 330 display a maintenance schedule to a user, including future maintenance required for various medical devices 302 as well as historical maintenance events tracked in the operations data 320.

Various external applications 332 extend the functionality of the software environment 300 by communicating with the operations module 314. The external applications 332 include any applications useable to extend the functionality of the software environment 300.

Figure 4:
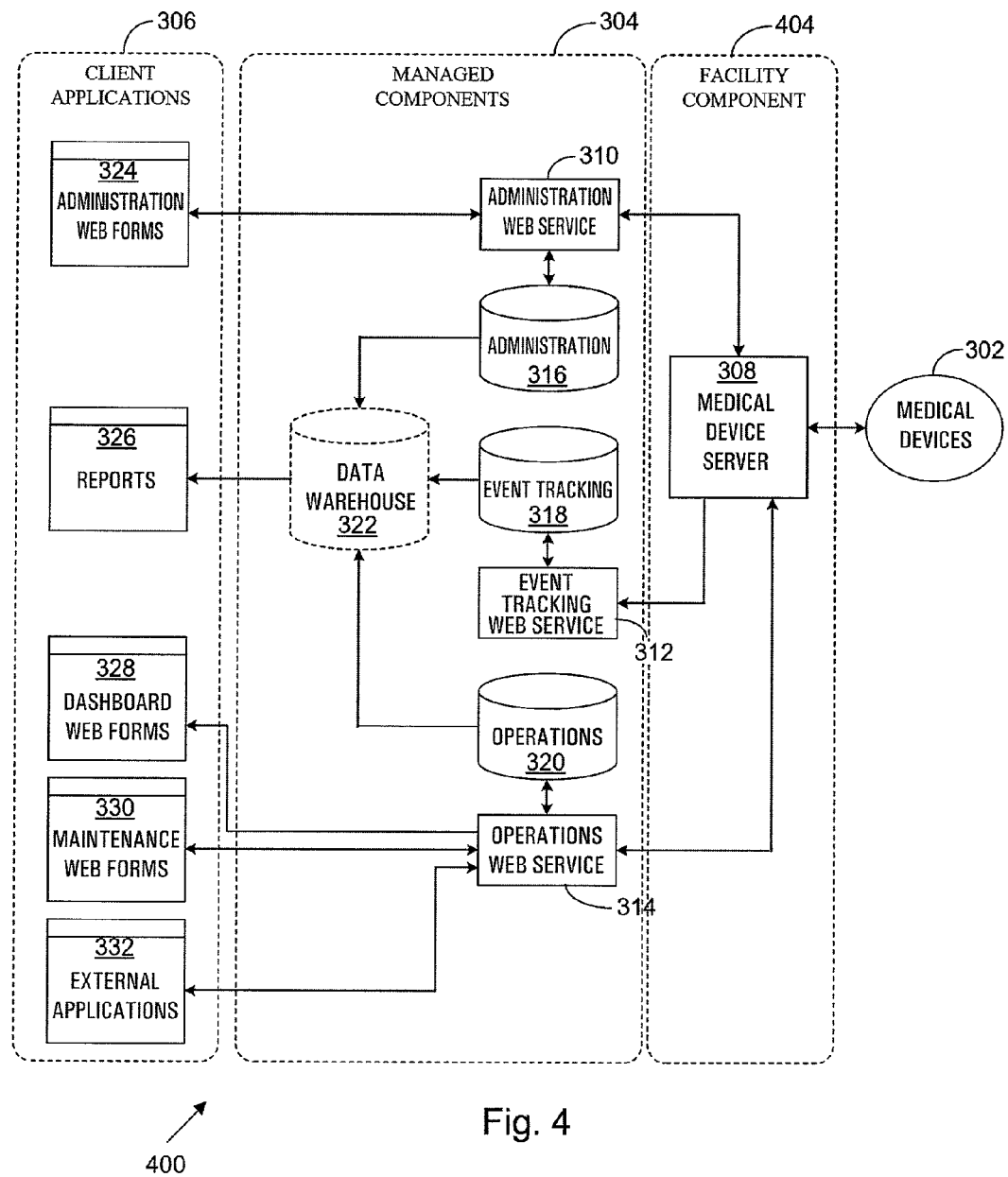
FIG. 4 is a diagram of a second software architecture for a medical device network.

FIG. 4 displays an alternative software infrastructure 400 to the one shown in FIG. 3, and may be used in the instance in which the storage of data from the medical devices is managed by an entity other than the facility at which the medical devices operate. For example, the medical devices 302 and medical device server(s) 308 may reside at one or more hospitals or health care facilities 404, managed by one or more healthcare entities, such as counties or private entities. However, the storage of data from those devices may be managed by a health management organization or other organization 405 contracting to manage the data of the various facilities at an off-site location. That entity can collect information from the medical device server 308 also residing at the facility, which in turn communicates data appropriately to one of the web-based modules 310, 312, 314 described above. Such an arrangement allows the hospital to aggregate data from its medical devices at a medical device server, but allows a third party to manage the computing infrastructure and perform the maintenance tasks related to long term storage, administration, access and/or reporting of the data.

Figure 5:
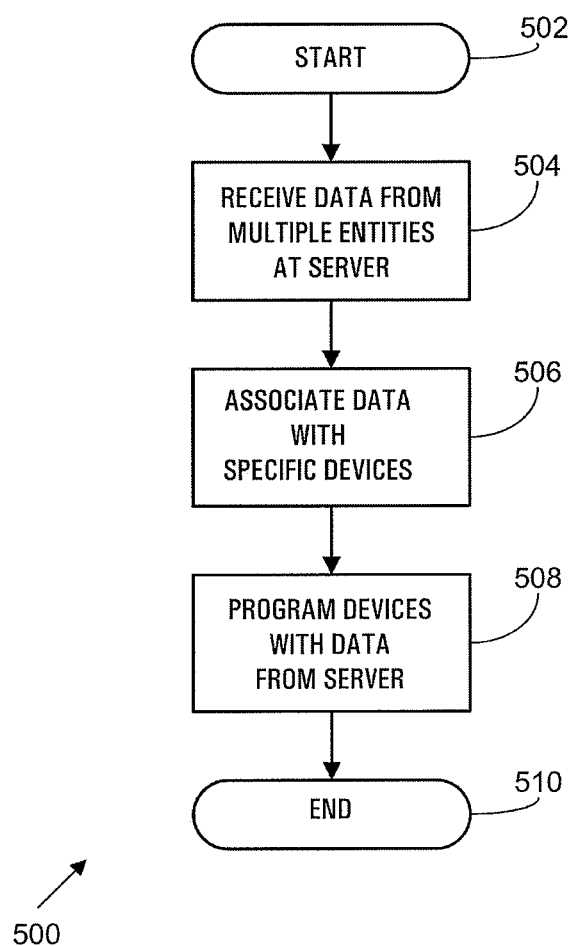
FIG. 5 is a flowchart of methods and systems for remote management of medical devices controlled by multiple entities.

FIG. 5 shows systems and methods for management of a software infrastructure such as the one shown in FIG. 4, in which a third party handles the data management tasks related to the data collected from medical devices located within and controlled by various healthcare organizations at various locations, or customer sites. Operational flow within the system 500 of FIG. 5 commences at a start operation 500, which corresponds to initialization of the system 500, such as by operation of various medical devices connected to a medical device server.

A data receipt module 504 receives data generated by the medical devices managed by one or more entities, such as hospitals, clinics, or other health management organizations. In one embodiment, the data receipt module 504 corresponds to receipt of various administrative data, event data, or operations data from a medical device server or client applications, as shown in the back office components 304 of FIG. 4.

An association module 506 associates the data received in the data receipt module 504 with the medical devices from which the data is received. In one possible embodiment, the association module 506 associates the data with the various locations at which the medical devices reside, or with the various entities controlling the devices, as defined in the administration data 316. The data association can be a logical or physical relationship between the data, such as can be found in a file, table, or database.

The association module 506 prepares the data such that when a user from a particular hospital or location seeks information about medical devices, the back office components can provide to that user only information about the medical devices at that same location or within the same entity as the user, depending upon the particular implementation of the association module 506. For example, a single hospital or ward of a hospital may have a variety of medical devices whose data is collected and managed by a third party. A doctor, nurse, or other caregiver working in that hospital or ward may access information related to the specific medical devices in that ward from a remote server, not controlled by that ward or hospital.

An optional program module 508 distributes data or instructions from the back office components to a medical device, based on the specific instructions related to that entity or location. For example, a hospital or ward can request a software upgrade to their medical devices, and the back office components will direct the specific software upgrade requested by the hospital to only that entity's devices or devices only of a specific type, excluding other devices associated with or monitored by the back office components.

In a further example, a workstation at a hospital or other healthcare location can view status information about the medical devices at that location, such as by execution of the data receipt module 504 and the association module 506, above. In this example, the user of the workstation may optionally choose to reprogram the medical devices, and can do so by issuing a global command to all of the medical devices of a specific type at the location associated with the user. The back office components can transmit to the appropriate medical device server the specific instructions necessary to distribute to the medical devices at that location, without transmitting those instructions to the same medical devices at other locations managed by the back office components.

Operational flow terminates at an end operation 510, which corresponds to completion of a communication session with one or more medical devices.

Figure 6:
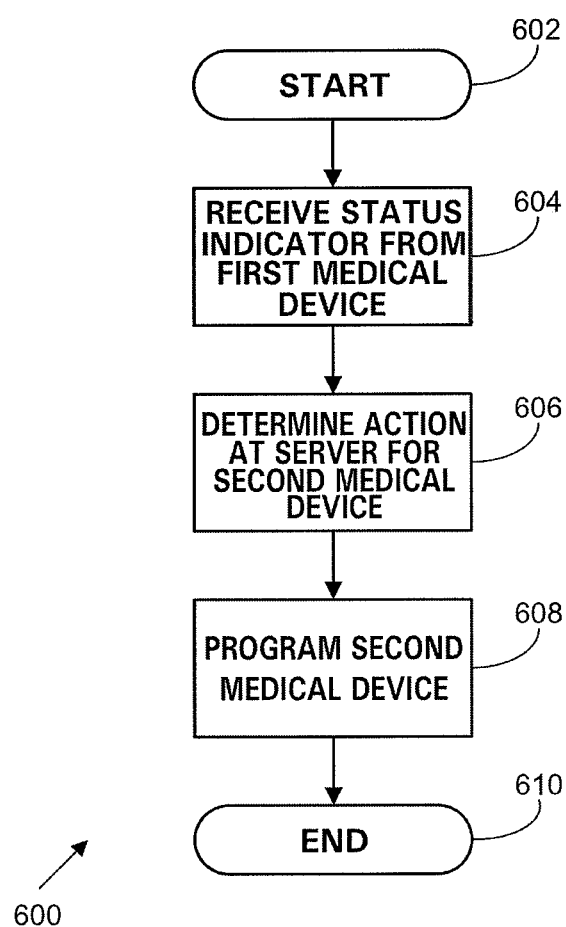
FIG. 6 is a flowchart of methods and systems for server based control of medical devices.

FIG. 6 shows systems and method executable within the medical device network of FIG. 1, in which medical device actions are interconnected. The system 600 specifically relates to interconnection of different types of medical devices at a specific location, such as a group of medical devices all associated with a single patient. The system 600 includes a number of rules which execute on the medical device server or other back office components so as to determine any additional advisable therapy or monitoring activity using a second medical device based on observed activity of a patient with a first medical device, as received by the medical device server or back office components.

Operational flow within the system 600 commences at a start operation 602, which corresponds to initial monitoring of a patient using a plurality of medical devices connected to a medical device network. The start operation 602 also optionally corresponds to receipt of at least one event at the medical device server, as logged by a first medical device which is associated with a patient.

A status receipt module 604 receives a status of a patient from a first medical device used to monitor or administer a therapy to the patient. In one example, the status receipt module 604 can receive a status of a patient from a medical device associated with that patient. The status of the patient may include the heart or breath rate or regularity, an indication by the patient that he is experiencing pain, the blood glucose level of the patient, or the progress of one or more therapies administered to the patient. The status of the patient optionally also includes alarms generated by medical devices monitoring or delivering therapies to the patient.

A determination module 606 executes one or more rules based on the status of the patient received from the first medical device. The one or more rules define whether any additional action is needed with respect to that patient, such as additional or changed therapies or monitoring of the patient. The determination module 606 associates various rules with specific medical devices capable of executing the changed therapy. Only those rules are executed which correspond to active medical devices currently monitoring or delivering therapies to the patient. In one example of execution of the determination module 606, there may exist an instance in which a monitor senses or is told that the patient is experiencing pain. In such an instance, one or more rules execute to determine whether a pain management therapy is available to that patient, and, if such a therapy is available, to determine an appropriate therapy to be administered to that patient. For example, if a medical infusion pump is associated with that patient, the determination module 606 concludes that the pump is capable of delivering a pain management therapy and calculates appropriate pump parameters for delivery of the appropriate therapy to the patient.

A program module 608 generates programming for a target medical device capable of providing the changed or additional therapy or monitoring determined in the determination module 606. The program module 608 communicates the changes or additions to the therapy to either a workstation accessible to a caregiver of the patient, or to a medical device capable of administering the therapy. In one embodiment, the program module 608 requests that a caregiver approves the suggested therapy determined in the determination module 606. In a further embodiment, the program module 608 directly programs the medical device capable of delivering the therapy, such that the therapy may be delivered without any additional caregiver approval or intervention.

Operational flow terminates at an end operation 610. The end operation 610 corresponds to the medical device server completing communication of the determined therapy to a workstation or medical device.

III. Medical Device to Server Communication

FIGS. 7-35 describe generally various systems and methods for communication between the medical devices and the medical device server or other back office components, as shown in FIGS. 1-2. The systems and method described in this section relate to coordination of medical devices in a medical device network, which may span across one or more facilities, organizations, time zones, or other logical entities. These systems can be used during user interaction with the medical device network, described in Part IV, below, in that involvement with the user relates to coordination of medical devices as well as collection and communication of data from the medical devices in the medical device network.

Figure 7:
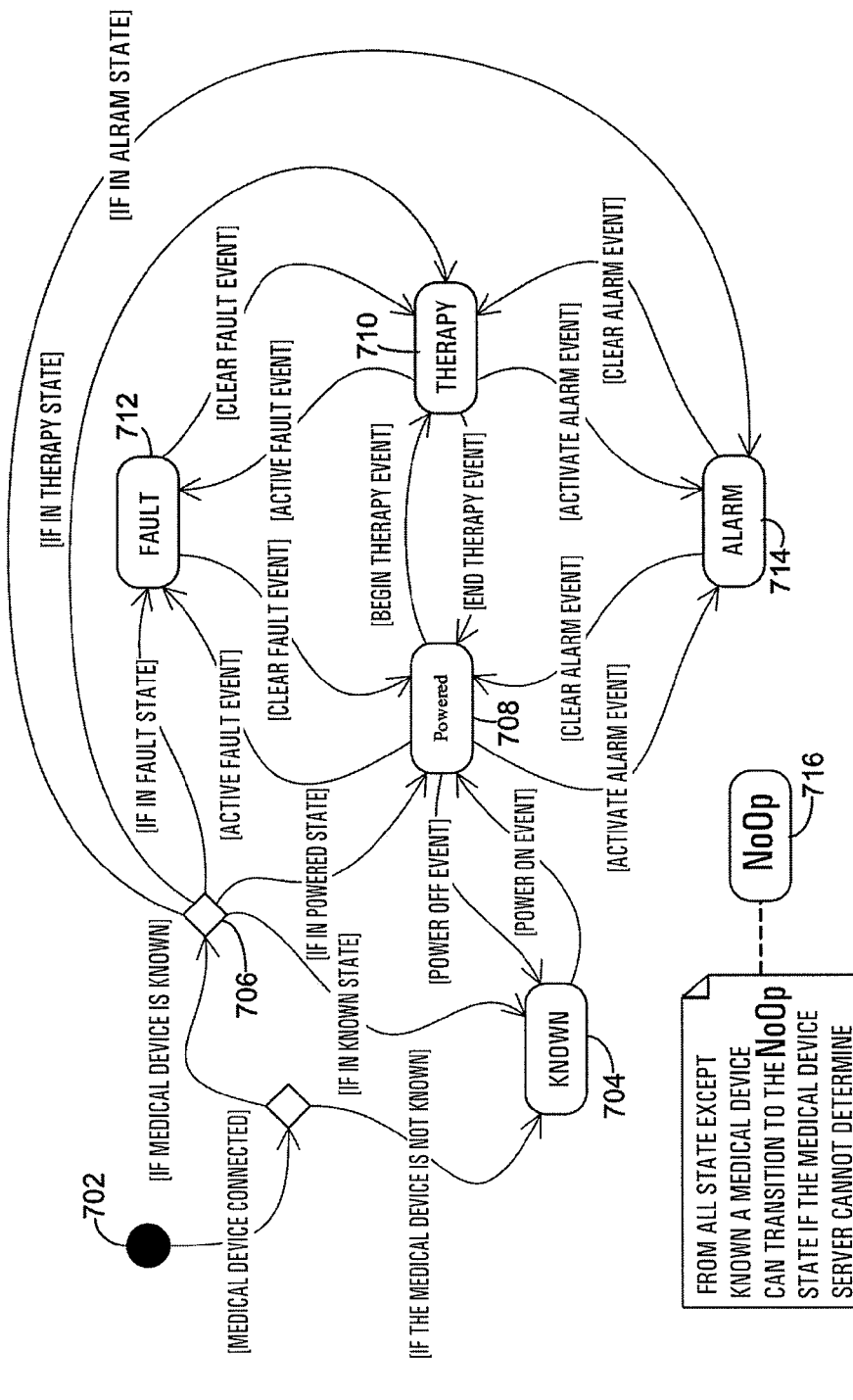
FIG. 7 is a state diagram of possible state for remote control of a medical device.
Figure 8:
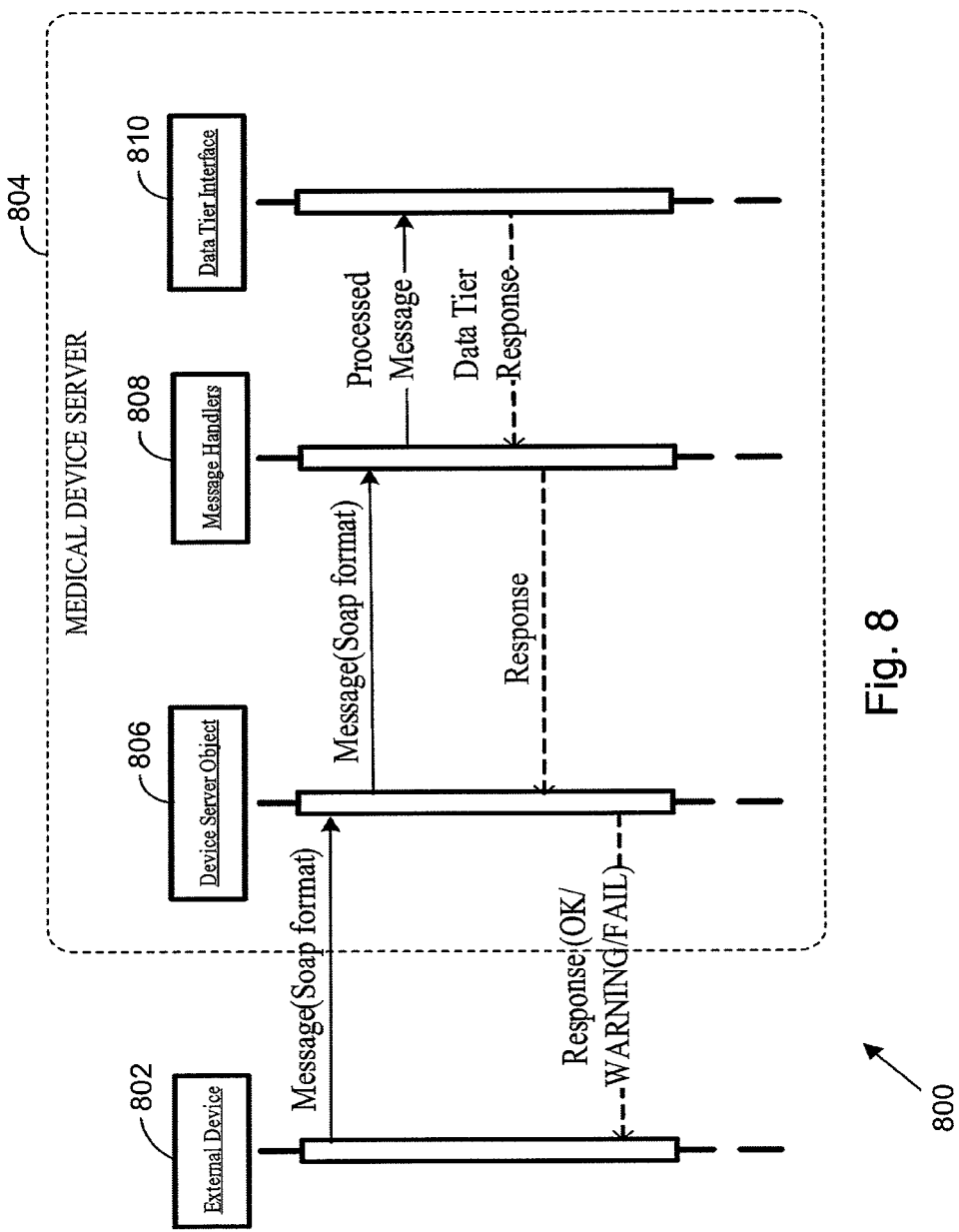
FIG. 8 is a functional diagram of a messaging system for use in a medical device network.

Referring now to FIGS. 7-8, communications between a medical device server and a variety of types of medical devices are described. The communication methods used by the medical device server and the medical devices provides an extensible system allowing the medical device server to communicate with a variety of different types of medical devices made by a variety of different medical device manufacturers, each having different communication protocols, capabilities, and other characteristics.

FIG. 7 shows an exemplary extensible system 700 in which a medical device server associates with a remotely located medical device. The system 700 tracks the states of medical devices associated with a medical device server, and is used to associate new and existing medical devices with the medical device server to provide an extensible medical device network allowing intercommunication of a variety of types and brands of medical devices placed at a variety of different hospitals or locations within a hospital. In the system 700, every medical device recognized by a medical device server will have an associated state held in a table on the server. Therefore, the system 700 will execute independently on the server for each medical device associated with the server. The system 700 commences at a start node 702 corresponding to connection of the medical device to a medical device network including a medical device server, such as the one shown in FIG. 1.

Upon connection of the medical device, the medical device server must determine whether the medical device is of a known type. If the medical device is of an unknown type, operational flow proceeds to a known state 704, which corresponds to receiving information about the capabilities of the medical device, so that the medical device is able to be added to the medical device network. The known state 704 may result from receiving user input describing the operational capabilities of the medical device, or may include communication or testing between the medical device and medical device server. When the medical device server considers a device to be in a known state corresponding to the known state 704, the medical server treats the medical device as a recognized device, but that is not powered on or otherwise recognized by the system. If the medical device is of a known type, operational flow proceeds to a determination node 706, which corresponds to determining the state of the medical device.

Four operational states define the operation of the medical device from the perspective of the medical device server: a powered state 708, a therapy state 710, a fault state 712, and an alarm state 714. The powered state 708 corresponds to a medical device which is powered on and experiencing normal operation, but is not currently being used to monitor or deliver a therapy to a patient. The powered state 708 is entered from the known state 704 or the determination node 706 when the medical device transmits an indication to the medical device server that it has been turned on. The powered state is entered from the remaining operational states, i.e. the therapy state 710, the fault state 712, and the alarm state 714, when the medical device server receives an indication that the medical device has cleared the condition causing the server to associate the medical device with one of those states.

The therapy state 710 corresponds to a medical device communicating to the medical device server that it is currently in operation, delivering a therapy or monitoring a patient. The specific action taken by the medical device will be dictated by the characteristics of that specific medical device; however, the medical device server need only recognize that the medical device is currently in operation. The system 700 can enter the therapy state from any of the other operational states 708, 712, 714, or from the determination node 706. When the medical device successfully completes the therapy, it communicates that event to the medical device server, which returns the table entry associated with that device to the powered state 708. If the medical device fails to complete the therapy due to a fault or alarm event, it will communicate that event to the medical device server, which changes the table entry associated with the device to the appropriate operational state.

The fault state 712 corresponds to an error occurring in the medical device, such as a malfunction in the operation of the device during monitoring or therapy delivery. The fault state 712 can be entered from either the powered state 708 or the therapy state 710, and can also be entered from the determination node 706. In a possible embodiment, the fault state 712 can trigger notification of a caregiver having control of the medical device that a fault has occurred. In a further embodiment, when the medical device server receives an indication which generates a fault state entry in the table, the server can determine the fault occurring in the medical device and can correct the error. Upon clearance of the fault state, the medical device transmits an indication to the medical device server that it has returned to its previous operational state, or has entered the powered state 708 if returning from the determination node 706. The table held by the medical device server tracking the state of the medical device is updated appropriately to reflect the state of the medical device.

The alarm state 714 corresponds to the medical device server receiving an indication from the medical device of an event occurring in the medical device which requires the attention of a doctor, nurse, or other caregiver. For example, the medical device may be a medical infusion pump which has run out of medicine for delivery. In another example, the medical device is a heart rate monitor, and the event is monitoring and detection of an abnormally low or high heart rate. The alarm state 714 can be entered from either the powered state 708 or the therapy state 710, and can also be entered from the determination node 706. Upon clearance of the alarm event, the medical device transmits an indication to the medical device server that it has returned to its previous operational state, and the table is updated appropriately.

A nonoperative state 716 may be entered from any of the active states, including the powered state 708, the therapy state 710, the fault state 712, or the alarm state 714. The nonoperative state 716 corresponds to the server being unable to determine if the medical device is active, or what state the medical device is in. The nonoperative state 716 indicates to a user of the medical device server that attention to that medical device may be needed so as to properly associate the medical device to the medical device server.

In an example of operation of the system 700, when a medical device is introduced into a medical device network, the medical device server may or may not know how to communicate with it. Assuming it is a known device that is not currently powered, the medical device server will eventually enter the known state 704. When the medical device is turned on, the medical device will transmit a power on message to the server, which will update the table to indicate that the medical device is in the powered state 708. The medical device will send to the server a message when the medical device delivers a therapy, and the medical device server will associate that medical device with the therapy state 710. When the medical device completes delivering that therapy successfully, the medical device will send a message to the server, which will change the table entry of that device from the therapy state 710 to the powered state 708. If the medical device fails for some reason, it will communicate a fault message to the server, which will associate the medical device with the fault state 712.

If the medical device runs out of a drug or detects a dangerous condition of the patient, the device will communicate an alarm message to the server, which will associate the medical device with the alarm state 714. When the device completes delivering the therapy, it sends a message to the server that delivery of the therapy is complete, and the server associates the medical device with the powered state 708. A caregiver may then turn off the medical device, and prior to shutting down the device sends a message to the server, which in turn associates the medical device with the known state 704.

FIG. 8 displays a diagram of an exemplary communications system 800 incorporating a medical device server and a medical device. The communications system 800 is configured for receipt, processing, and storage of input messages from external devices, such as medical devices. In one embodiment the communications system 800 uses a metadata-based communications protocol, such as the SOAP protocol. In such a system, the medical device server uses message schema files to validate messages received from medical devices.

The communications system 800 is configured such that messages sent from a medical device 802 are received by a medical device server 804, which includes a device server object 806, message handlers 808, and a data tier 810. The medical device 802 can be any of a number of medical devices capable of communication with a medical device server. Various embodiments of the medical device are described above in conjunction with FIG. 2.

The medical device server 804 can be any of a number of generalized computing systems configured to collect information from medical devices and assist with medical device setup and monitoring. The medical device server 804 contains a device server object 806, which handles messages sent and received from the medical device server, and parses the messages to determine that they include required information for the medical device server to act on the message. For example, the device server object can parse various metadata tags contained in the message, as well as data associated with that metadata, to verify the message type, source or destination device identification or network identification, and message data. Other components of the message may be determined as well.

Exemplary message contents describe various features of the device server object 806, as well as for the various device handlers incorporated into the system. A sample device server object definition can read as follows:

```
<Feature>
<Id>XXXXXXXX-XXXX-XXXX-XXXX-XXXXXXXXXXXX</Id>
<LicenseId>XXXXXXXX-XXXX-XXXX-XXXX-
XXXXXXXXXXXX</LicenseId>
<Name>Medical Device Secured Server</Name>
<Provider>MedicalDeviceServer.MedicalDeviceSoapTcpServer,
MedicalDeviceServer.MedicalDeviceSoapTcpServer.-
MedicalDeviceSoapSecureTcpServer</Provider>
  <Description>Receives inbound connection over SSL
  secured TCP/IP networks.</Description>
<Type>Server</Type>
</Feature>
```

In this example, the Feature tag defines the object as a feature of the device server object. The Id tag defines the GUID, or statistically unique number used to identify the feature. The LicenseID tag identifies the license containing the features defined. The Name tag provides the name of the feature. The Provider, Description, and Type tags define the various implementation details of the object. Additional implementation details may be included as well.

One or more message handlers 808 receive the message in its original format from the device server object 806, and process the message in a manner to convert the message to a format understandable to and stored by the data tier 810 of the medical device server 804. The various handlers are assigned messages based on the type of message received, with each handler processing a specific type of messages in a given way. In one embodiment, the message handlers include an alarm handler, a fault handler, a maintenance handler, a power handler, a request handler, various telemetry handlers, and various therapy handlers. Additional or fewer handlers are possible, based on the variety of types of messages managed by the medical device server 804.

A second exemplary server object definition describes various features of a message handler 808:

```
< Feature >
<Id>XXXXXXXX-XXXX-XXXX-XXXX-XXXXXXXXXXXX</Id>
<LicenseId>XXXXXXXX-XXXX-XXXX-XXXX-
XXXXXXXXXXXX</LicenseId>
<Name>Medical Device Event Handler</Name>
<Provider>Informatics.BackOffice.MedicalDeviceServer</Provider>
```

-continued

```
<Description>Validates received events and stores them in the
Operations database</Description>
<Type>Handler</Type>
</Feature>
```

The example for the message handler 808 is analogous to that describing the device server object 806, but defined using a Provider tag indicating that the metadata defines a handler configured to define a feature. The message handler 808 can be associated with the device server object 806 using the following code:

```
<Handler>
...
<FeatureId>XXXXXXXXXXXX-XXXX-XXXX-
XXXXXXXXXXXX</FeatureId>
<HandlerId>XXXXXXXX-XXXX-XXXX-XXXX-
XXXXXXXXXXXX</HandlerId>
...
</Handler>
```

By tying a feature 806 to a handler 808, the medical device server 804 can route specific types of data to the appropriate handler.

A data tier 810 receives messages from the message handlers 808 for storage, and also responds to requests for data by providing data to the requesting message handler 808 for formation into a SOAP-based message or transmission to the medical device via the device server object 806.

A. Metadata Programming and Communication

Referring now to FIGS. 9-16, a programming schema is disclosed which lists metadata used to define the operational characteristics of a variety of medical devices. The metadata also allows the medical device server to communicate with a wide variety of medical devices, such as medical infusion pumps or other therapy delivery or monitoring equipment. By defining medical devices in the medical device server in terms of their operational characteristics rather than specific proprietary interfaces, the medical device server need not understand the inner workings of each type of medical device. Rather, the server will understand how to communicate with the medical device based on expected operation of that device. In general, the metadata schema disclosed operates using the XML protocol, and a SOAP based messaging system as described above in FIG. 8. However, other standardized communication methodologies could be used as well.

Figure 9:
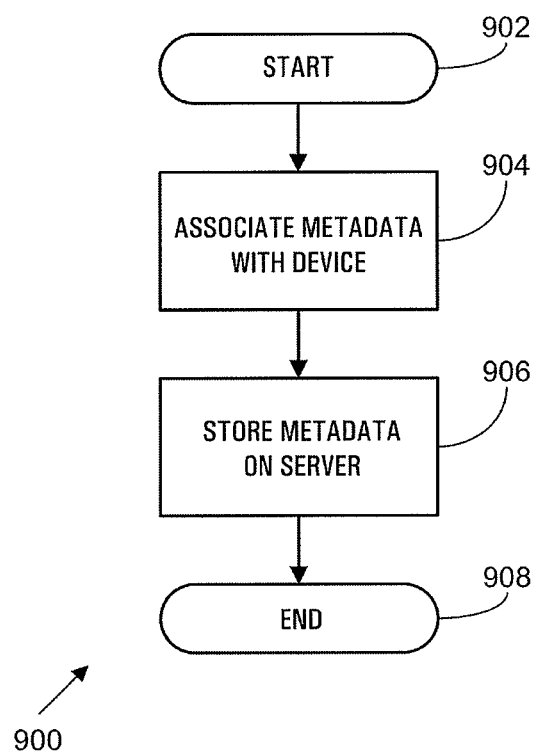
FIG. 9 is a flowchart of methods and systems for communication between a medical device and a medical device server.

FIG. 9 shows systems and methods for communication between a medical device and a medical device server. The system 900 shown is configured to provide extensibility to a variety of types and brands of medical devices, as described above in FIG. 2. The medical device server can communicate with the medical device by defining a predetermined set of metadata and associated parameters for each medical device. The system 900 instantiates at a start operation 902, which corresponds to communicatively connecting a medical device to a medical device server. In one embodiment, the communicative connection corresponds to introducing the medical device into a medical device network including a medical device server, such as the network shown in FIG. 1. In a further embodiment, the communicative connection corresponds to installation of a corresponding metadata package onto the medical device, using software for installing a metadata communication layer provided in a software development kit or otherwise provided as consistent with the present disclosure.

An association module 904 associates metadata with various medical devices in a database of a medical device server. The medical devices store corresponding metadata, so that the associated metadata corresponds to the metadata set on the device. The metadata corresponds to at least one attribute or operational characteristic common to the medical devices, and can be used to distinguish among, identify, and communicate with the various medical devices in the medical device network. In various possible embodiments, operational characteristics defined by the metadata include patient information, user or caregiver information, control information, drug information, or location information. Additional operational characteristics can be included as well, such as those described in one or more of the schema of FIGS. 11-16. The metadata also corresponds to various events occurring in the medical device, such as power events, alarm events, maintenance events, telemetry events, therapy events, therapy change events, or other events. Additional events are described below in FIGS. 17-33.

A storage module 906 stores the metadata on a medical device server or back office components. The medical device server is configured to communicate with each of the medical devices by using the metadata and the metadata-based messaging systems described above in conjunction with FIG. 8. Operational flow proceeds to an end operation 908, which corresponds to completion of establishing the communication schema between the medical device and medical device server.

Figure 10:
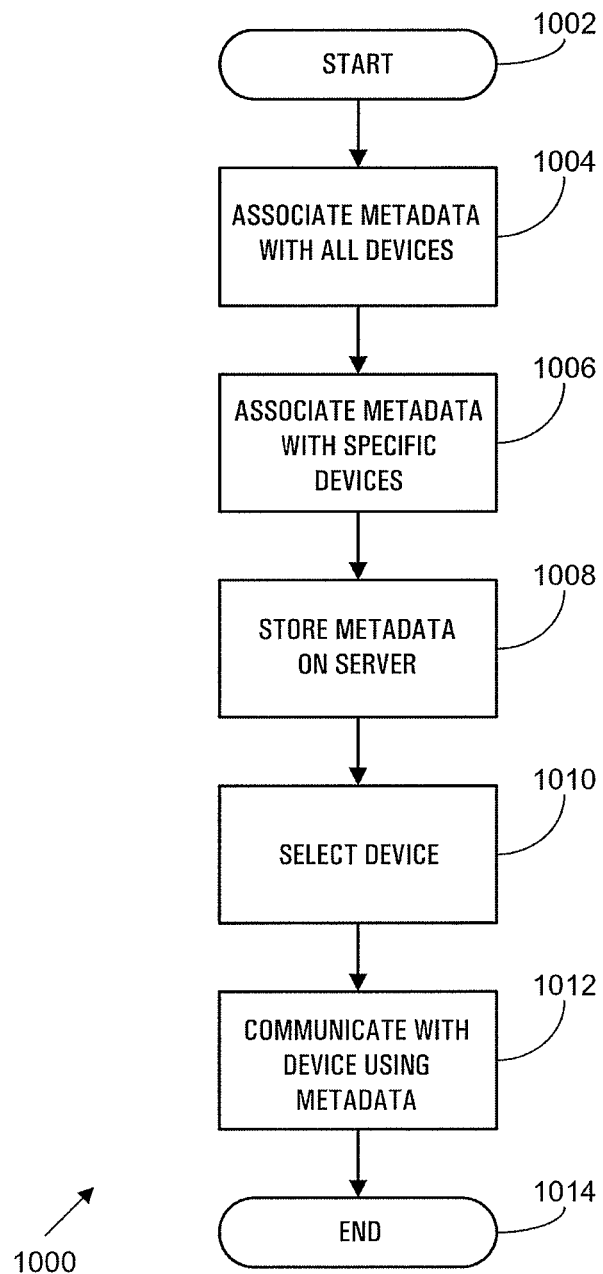
FIG. 10 is a flowchart of further methods and systems for communication between a medical device and a medical device server.

FIG. 10 shows further systems and methods for communication between a medical device and a medical device server. The system 1000 of FIG. 10 stores metadata common to all medical devices in the medical device networks, and also stores information specific to a subset of the medical devices as well, allowing for customized communications between those medical devices and the medical device server. Operational flow of the system 1000 commences at a start operation 1002, which again corresponds to communicatively connecting a medical device to a medical device server in a medical device network.

Following the start operation 1002, operational flow proceeds to a general association module 1004. The general association module corresponds to the association module 904 of FIG. 9, in that it associates metadata defining the characteristics of each medical device in the medical device network by defining a predetermined set of metadata and associated parameters for each medical device. A custom metadata module 1006 associates metadata with one or more medical devices, the metadata being specific to that device. Examples of custom metadata include specific power events occurring in a particular type of medical device, specialized communication types supported by those devices, or other operational parameters which are defined for less than all of the devices included in a medical device network. A storage module 1008 generally corresponds to the storage module 906 of FIG. 9, and stores the general metadata and the custom metadata on the server.

A device selection module 1010 selects one or more of the medical devices in the medical device network to communicate with, based on the metadata defining that device stored in the medical device server. In one embodiment, the device selection module executes upon receiving a message from the medical device(s). In a further embodiment, the medical device server selects and communicates with one or more medical devices without receiving a previous signaling communication from one of the medical devices.

A communication module 1012 transmits a message to the selected medical device determined in the device selection module 1010. The communication module forms a SOAP-based message for transmission to the medical device, including destination information identifying the medical device as well as the data to be transmitted to the medical device. The message includes various information identified by the metadata tags defined in the schema understood by the system 1000, such as those described in FIGS. 11-16 and 19-24, below. Operational flow terminates at an end operation 1014, which corresponds to completion of transmission of the message to the medical device.

FIGS. 11-16 show various schema including metadata useable to facilitate extensible communication systems for medical devices and medical device servers. The schema are used in the medical device network of FIG. 1 to identify a variety of medical devices to a medical device server, and to allow the medical device server to communicate with the devices. The schema include metadata related to various operational parameters, or attributes, common to all of the medical devices in the network or specialized to one or more of the medical devices. By using the various schema disclosed, a medical device server can identify a medical device, identify the characteristics of the device, and know how to interoperate with the device by (1) knowing the device's capabilities and limits and (2) sharing an extensible communications protocol with other medical devices.

Figure 11:
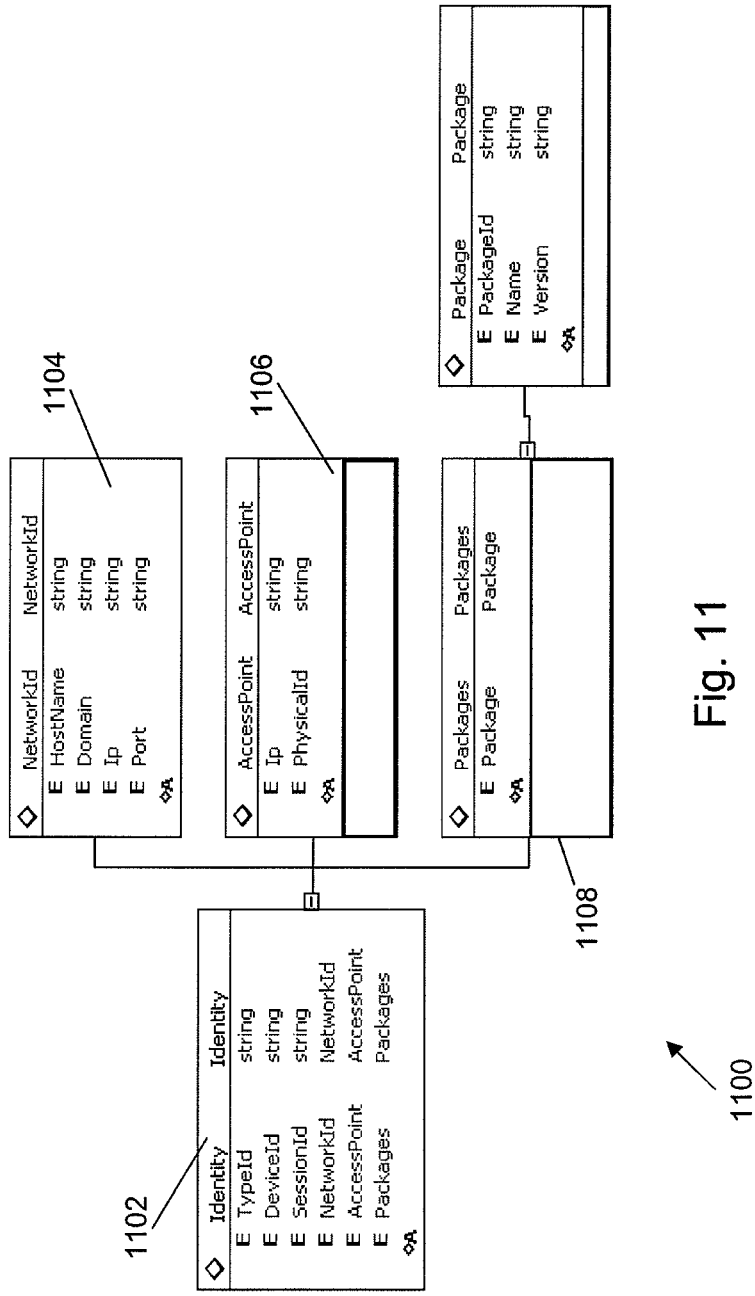

FIG. 11 shows an identity schema 1100 used to identify various operational characteristics of each of the medical devices communicatively associated with a medical device server. The identity schema 1100 includes a main table 1102 including a variety of global parameters, as well as a network table 1104, an access table 1106, and one or more package tables 1108. The main table 1102 includes metadata associated with a variety of generalized device identification characteristics, including device type, device identifier, session identifier, network identifier, access identifier, and package acceptance. The device type relates to identification of the type of the medical device such as the manufacturer and model of the device, while the device identifier is unique to each device. The session, network, and access identifiers define the connection string to allow the message to be routed correctly to the medical device. The package identifier indicates whether the medical device is configured to receive packages from the medical device server, and can link to tables indicating the current packages enabled on each device.

The remaining tables, including the network table 1104, access table 1106, and package tables 1108 provide additional information related to connection and capabilities of the medical device, and are linked to the main table by the network identifier, access identifier, and package identifier in the main table 1102. The network table 1104 includes the host, domain, IP address, and port information necessary to define a connection to the medical device over an Internet connection. The access table 1106 includes an IP address and Physical Id corresponding to the specific networking connection corresponding to the physical device to the IP address. The package tables 1108 describe additional details of the software or firmware package in use by the medical device, such as the name and version of the software package. Additional details regarding package deployment to medical devices are described below in conjunction with FIGS. 25-33.

FIG. 12 shows a control table 1200 which includes elements describing the logistics of sending messages and tracking those elements between the medical device and medical device server. The control table 1200 shown includes message identifier, timestamp, and response metadata. The message identifier provides an identification string used to track the message, and corresponds to the identity of the medical device. The timestamp indicates a time at which the message is sent from the medical device server or medical device. The response provides a Boolean indication of whether the message is originating from a medical device or is a response from the server. Additional metadata related to message tracking can be included in the control table as well.

FIG. 13 shows a patient table 1300 used to track patient information for association with the medical device. The patient table 1300 includes an identifier and a name element. The name element holds metadata related to the patient's name, and the identifier associates to a statistically unique identifier for association with that patient. Other patient-related metadata can be included as well.

FIG. 14 shows a location table 1400 used to indicate the location of a patient. The location table 1400 includes metadata defining an alias element and a description element. The description element refers to a linguistic description of the location of a patient, such as "Hospital X, Neonatology, Room 1" or some similar entry. The alias element provides a shorthand code used to associate the location with the medical device. Additional metadata describing the location of a patient or medical device can be included in the location table 1400 as well.

FIG. 15 shows a drug table 1500 used to indicate the drug, if any, associated with the medical device. The drug table 1500 may or may not be populated for each medical device, due to the fact that only some medical devices are capable of delivering drug-based therapies to a patient. The drug table includes metadata related to a drug identifier, a drug name, and a drug concentration. Additional metadata entries can be used to further identify or describe the drug in use by the medical device.

FIG. 16 shows a user table 1600 corresponding to a doctor, nurse, or other caregiver currently controlling the medical device. The user table 1600 includes metadata related to a user identifier and user name, as well as any additional identifying characteristics of the user necessary for operation of the system.

B. Event Logging and Maintenance

Now referring to FIGS. 17-24, systems, methods, and schema are disclosed which are used in the medical device network of FIG. 1 to track event and maintenance information for the various medical devices associated with the medical device server. These event-based schema can be used to track current and historical performance of the medical devices in the medical device network, as well as to maintain the medical devices. The schema described below define both a messaging system and an ordering of event or operational data stored by a medical device server or other back office components of a medical device network. The event logging and maintenance tracking schema define specific events or tasks occurring in the medical device network, as compared to the schema described in part II.A, above, which relate to relatively constant operational characteristics of the medical devices or server.

Figure 17:
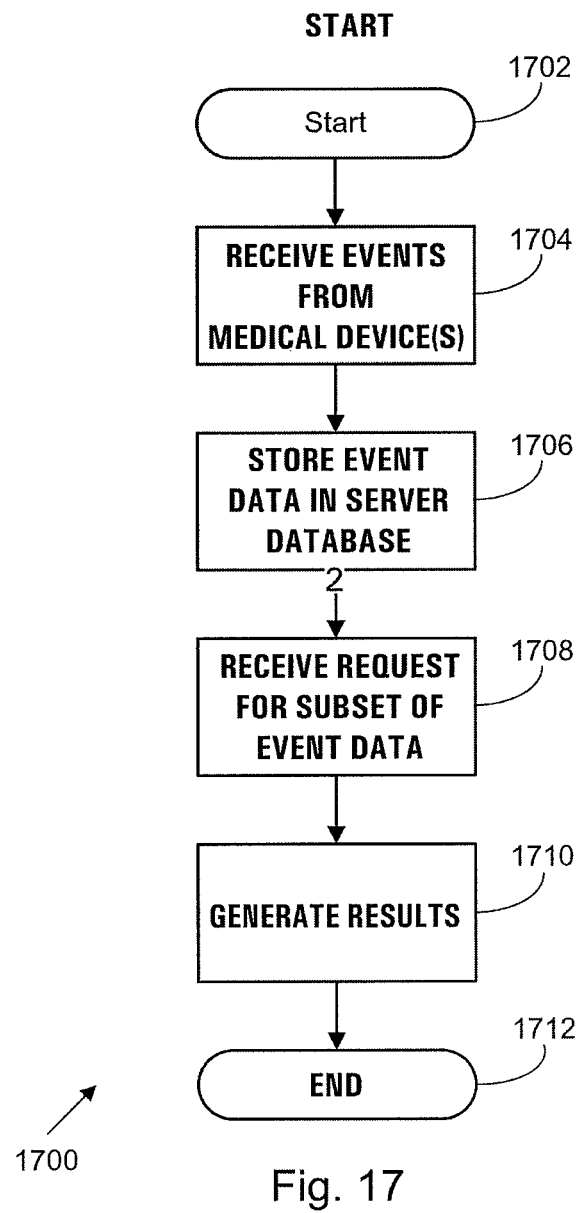
FIG. 17 is a flowchart of methods and systems for filtering medical device events.

FIG. 17 shows methods and systems for receiving event log results from the medical device server or back office components using the various event-based message schema disclosed in FIGS. 19-24. The system 1700 generally executes on a medical device server or other back office components of a medical device network, and provides event log data stored in one or more databases managed by those components to a caregiver or other user.

Operational flow in the system 1700 commences at a start operation 1702, which corresponds to initial operation of the medical device network. Operational flow proceeds to an event receipt module 1704, which receives event log data from the various medical devices associated with the medical device server. The event log data represents events occurring in the medical devices, and can be any of a number of types of events, such as power events, telemetry events, alarm events, therapy events, maintenance events, or other events such as those defined in the schema of FIGS. 19-24.

A sample message body illustrates communication of an event from a medical device to the medical device server, such as is received by the event receipt module 1704. In the example, the medical device is a medical infusion pump that is sending a power event to the medical device server, indicating that the pump has been turned on:

```
<env:Body><mds:PowerEvent xmlns:mds='mds:xml-schema:soap11'>
<Trigger>on</Trigger>
<Message>Normal Power Up Complete</Message>
<Timestamp>1900-01-01T00:00:08</Timestamp>
<Medfusion4000_Power>
<Source>AC</Source>
<Capacity>90.0%</Capacity>
</Medfusion4000_Power>
</mds:PowerEvent></env:Body>
```

This message portion identifies that this is the body of the message, and that it uses the SOAP 1.1 messaging protocol. The message transmitted from the pump indicates that power up process has been completed, and includes a timestamp assigned by the pump. The various power parameters correspond to those parameters included in the power event table of FIG. 19, below, and are associated with specific values by the medical infusion pump. The message is received from the medical infusion pump by the medical device server, and the values are stored in appropriate database tables corresponding to the power event schema.

Analogous messages are sent from the medical device to the medical device server, and responses are sent from the server back to the medical device, as related to the other types of events tracked in the medical device network, as described herein.

A storage module 1706 stores the event log data in a database associated with the correct metadata as defined in the message from the medical device to the server. In one embodiment, the storage module 1706 stores event log data in the event data 318 of FIGS. 3-4.

A request receipt module 1708 receives a request for a subset of the event log data stored in the medical device server or other back office components. The request received may come from a workstation, portable computing device, or other type of computing system. The request includes one or more narrowing parameters such as a date range, a caregiver name or identifier, a patient name or identifier, a drug name or identifier, a specific device, or other types of information associated with the event log data. In one example, the request receipt module 1708 receives a request for event log data related to delivery of a specific drug by a medical infusion pump.

A result generation module 1710 generates results based on the specific request received by the request receipt module 1708, such as by filtering event log data held by the medical device server or back office components based on the narrowing parameters of the request. The result generation module 1710 optionally also transmits the results to the requesting computing system. Using the example described in the request receipt module 1708, the medical device server generates a query configured to return event log data related to delivery of the identified drug by the identified pump. This query can be formed in SQL or some other database querying language, such that the database management system associated with the medical device server returns the query results.

Operational flow terminates at an end operation 1712, corresponding to completion of generation and transmission of results to the requesting computing system.

Figure 18:
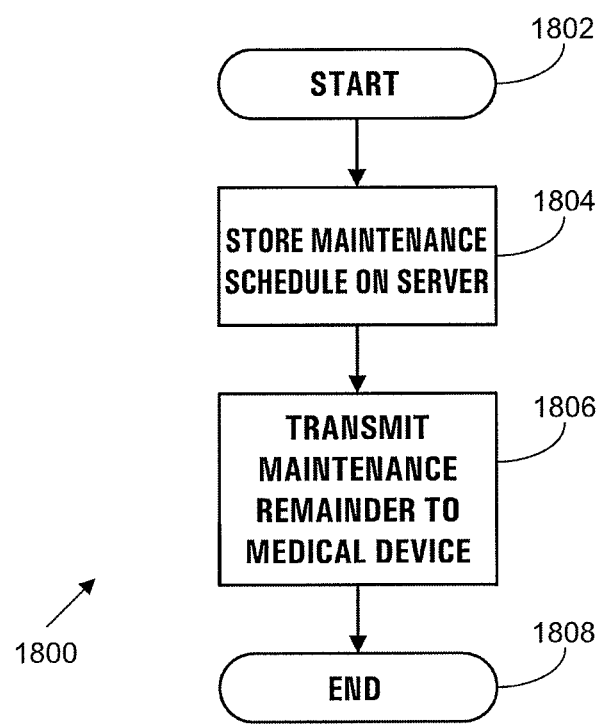
FIG. 18 is a flowchart of methods and systems for managing maintenance of medical devices.

FIG. 18 shows systems and methods for communicating preventative maintenance data to a medical device. The system 1800 uses the metadata of FIGS. 11-16, as well as the additional event metadata of FIG. 19-24, to track and communicate maintenance tasks to be performed on one or more of the medical devices in a medical device network. The various message transmission principles described in conjunction with FIG. 17 allow the communication to occur.

The system 1800 commences at a start operation 1802, which corresponds to initial operation of the medical device network. Operational flow proceeds to a storage module 1804, which stores a maintenance schedule on the medical device server associated with one or more medical devices. The maintenance schedule is stored in a database of the medical device server or back office components, and includes both a time value for the maintenance reminder events included in the schedule and for the medical device. The maintenance schedule also optionally references maintenance data, such as required operational software updates or various other configuration parameters.

In one example, the storage module 1804 stores a maintenance schedule that includes indications for suggested recalibration of a series of medical infusion pumps periodically, or for a specific medical infusion pump. In such an example, the storage module 1804 can store a maintenance schedule provided by the user or manufacturer of the medical infusion pump to provide reminders to the user of the pump when the indicated maintenance is scheduled.

A transmission module 1806 transmits a reminder to the one or more medical devices associated with the maintenance schedule when a maintenance event occurs. The reminder may be a user-readable message displayed on a display associated with the medical infusion pumps, indicating to the caregiver that recalibration is suggested. Or, the reminder may be a trigger of a user-readable message stored on the medical device.

The transmission module 1806 also optionally transmits maintenance data associated with the maintenance reminder. In one embodiment of the system 1800, the reminder sent by the transmission module 1806 disables the medical device. In a further embodiment, the reminder allows the medical device to continue operation. In yet another embodiment, the reminder is transmitted a predetermined time prior to performance of the required maintenance of the medical device.

Continuing the example of the medical infusion pump from the storage module 1804, above, a maintenance event is transmitted to the medical infusion pumps. The maintenance event indicates to a medical device that maintenance of that device is needed, and includes a reminder message displayed on a display device of the medical infusion pump, such as "Maintenance Required—Please Contact Manufacturer", or some other indication of required maintenance. In certain configurations, the maintenance event allows the medical device to continue operation until a caregiver contacts the manufacturer, who may have specific instructions regarding maintenance and care of the medical device.

Operational flow terminates at an end operation 1808, which corresponds to completion of the transmission of a maintenance reminder and any corresponding maintenance data to the medical device.

FIGS. 19-24 show event-based schema for communications and responses between medical devices and a medical device server. The schema disclosed are useable in the medical device network of FIG. 1 to allow the medical device server and back office components to gather and store event log data, as well as to transmit messages to the medical devices. The medical devices and medical device server of the network transmit messages and event data using the metadata described below to identify the contents of the messages. The medical device server or back office components store the event data in correspondence with the metadata.

Figure 19:
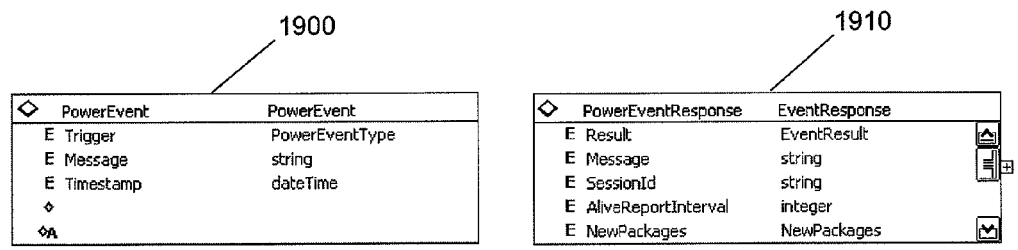
FIGS. 19-24 are data models including event metadata useable to track events occurring in medical devices.

FIG. 19 shows a power event table 1900 and a power event response table 1910. The tables 1900, 1910 define metadata used to track various power events in a medical device, such as turning the device on, turning the device off, battery warnings, and other power-related events. The power event table 1900 includes metadata related to a trigger, a message, and a timestamp. The trigger corresponds to a changed event in the medical device, such as turning the device on, off, or updating the powered status of the device. The message describes the specific event that occurred in the medical device, such as a low battery warning, an occurrence of power on event, an occurrence of a power off event, or some other power-related event. The timestamp indicates the time at which the medical device experienced the power event.

The power event response table 1910 includes metadata defining various possible responses to the power events received by the medical device server. For example, when the medical device server receives a power on event, the server may respond that specific maintenance tasks are required, or that software or firmware is available to be downloaded. The power event response table includes result, message, session, interval, and package metadata. The result metadata relates to the result of the power event, such as a changed state of the medical device, or various other server-recognized results of the received event. The message metadata includes a message to be transmitted to the medical device, such as to describe the contents of the response message, for display on a display device associated with the medical device. The session metadata includes information related to the communication session between the device and server. The interval metadata includes information related to the expected interval between communications from the medical device to the server, which is related to server detection of the on-line status of the medical device, described in Part IV, below. The package metadata provides an indication to the device as to whether new package information is available for that device, and which may be delivered via the package deployment methods and systems of FIGS. 25-33. Additional metadata may be included in the response table 1910 and the corresponding response message.

Figure 20:
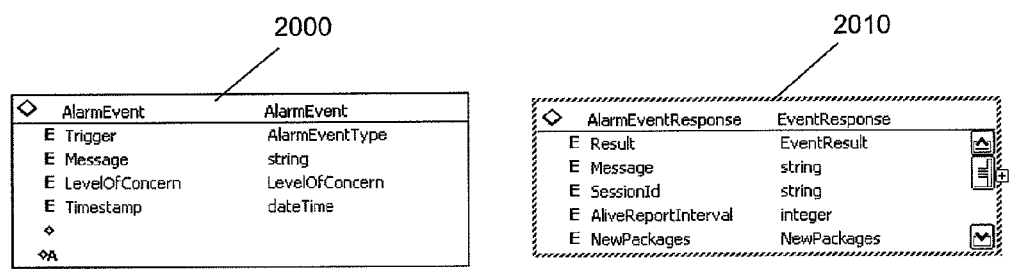

FIG. 20 shows an alarm event table 2000 and an alarm event response table 2010. Alarm events relate to activation or clearing of an alarm triggered in a medical device, and the corresponding messages generated by the device and communicated to the medical device server. Activation or clearing of an alarm in the medical device may relate to detection of a patient condition detected by the medical device, or may relate to the The alarm event table 2000 corresponds to the power event table 1900 in that it also includes trigger, message, and timestamp metadata. In the case of the alarm event table 2000, the trigger metadata relates to an activate, clear, or update alarm message. The message and timestamp metadata are used analogously to the corresponding fields of the power event table 1900.

The alarm event response table 2010 corresponds to the power event response table 1910. Messages generated using the alarm event response table metadata are communicated to the medical device in response to receipt of an alarm event message. The alarm event response table 2010 therefore generally includes a different response than the power event response table 1910, and communicates messages, packages or other instructions related to the alarm event.

Figure 21:
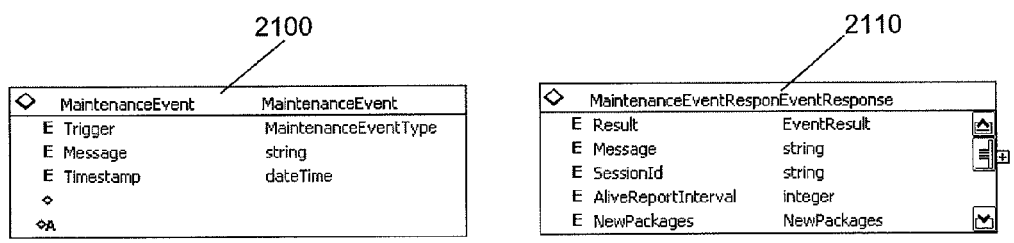

FIG. 21 shows a maintenance event table 2100 and a maintenance event response table 2110. Maintenance events correspond to specific reactions of the medical device to an indication that maintenance is required, such as requesting updated operational software, calibration software, or notification messages indicating the maintenance that is required. The maintenance event table 2100 corresponds to data received in a message from a medical device ready to perform maintenance in conjunction with the medical device server, for situations in which maintenance requires a software upgrade or some other remotely-controllable maintenance event. The maintenance event table 2100 corresponds to the power event table 1900 in that it also includes trigger, message, and timestamp metadata. In the case of the maintenance event table 2100, the trigger metadata relates to an update or a package applied. The message and timestamp metadata are used analogously to the corresponding fields of the power event table 1900.

The maintenance event response table 2110 also corresponds to the power event response table 1910, and is generated by the medical device server or other back office components. Messages generated using the maintenance event response table metadata are communicated to the medical device in response to receipt of a maintenance event message, and relate to messages, packages or other instructions that occur response to the maintenance event, such as additional details regarding the maintenance required, maintenance schedule information, information to be displayed by the medical device about the maintenance required.

Figure 22:
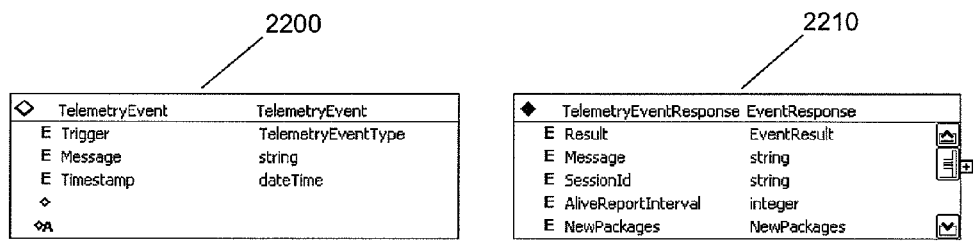

FIG. 22 shows a telemetry event table 2200 and a telemetry event response table 2210. Telemetry refers to near-continuous streaming of event data from a medical device to the medical device server such that users with access to the medical device server can monitor operation of the medical device remotely in a near real-time fashion. The telemetry event table 2200 corresponds to the power event table 1900 in that it also includes trigger, message, and timestamp metadata. In the case of the telemetry event table 2200, the trigger metadata relates to an update event regarding telemetry received from the medical device. The message and timestamp metadata are used analogously to the corresponding fields of the power event table 1900.

The telemetry event response table 2210 also corresponds to the power event response table 1910, but is generated by the server. Messages generated using the telemetry event response table metadata are communicated to the medical device in response to receipt of a telemetry event message, and communicate messages, packages or other instructions in response to the telemetry event.

Figure 23:
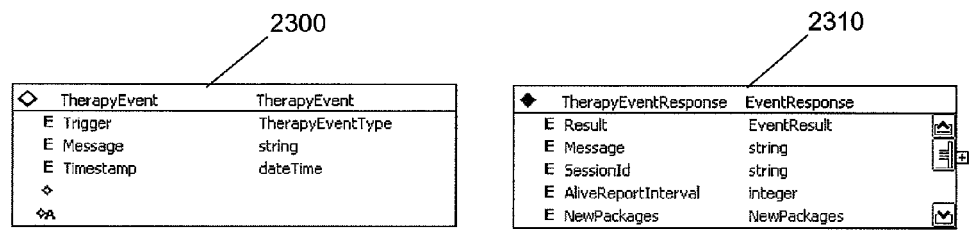

FIG. 23 shows a therapy event table 2300 and a therapy event response table 2310. Therapy events relate generally to the start and stop of therapies or monitoring processes in a medical device. The specific therapy started or stopped depends upon the type of medical device used, and can include monitoring, drug delivery, or other therapies. The therapy event table 2300 corresponds to the power event table 1900 in that it also includes trigger, message, and timestamp metadata. In the case of the therapy event table 2300, the trigger metadata relates to a setup, begin, end or update therapy event as related to initialization or ending of a therapy by a medical device. The message and timestamp metadata are used analogously to the corresponding fields of the power event table 1900.

The therapy event response table 2310 also corresponds to the power event response table 1910, but is generated by the server. Messages generated using the therapy event response table metadata are communicated to the medical device in response to receipt of a therapy event message, and communicate messages, packages or other instructions in response to the therapy event.

Figure 24:
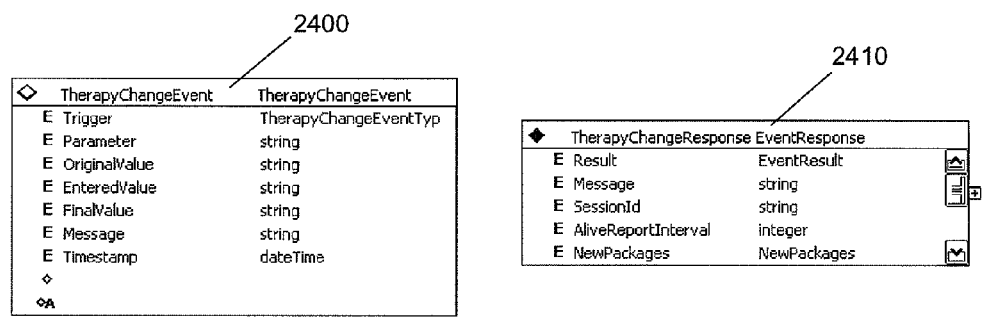

FIG. 24 shows a therapy change event table 2400 and a therapy change event response table 2410. Therapy change events relate generally to changes in therapies operating on a medical device, and are related to therapy events, discussed above. Therapy change events include, for example, changed parameters related to monitoring or delivering of therapies, such as changed drug delivery rates. The therapy change event table 2400 corresponds to the power event table 1900 in that it also includes trigger, message, and timestamp metadata. In the therapy change event table 2400, the trigger metadata relates to an override, warning, abandon, or update event as related to a therapy change. The message and timestamp metadata are used analogously to the corresponding fields of the power event table 1900.

The therapy change event response table 2410 also corresponds to the power event response table 1910, but is generated by the server. Messages generated using the therapy change event response table metadata are communicated to the medical device in response to receipt of a therapy event message, and communicate messages, packages or other instructions in response to the therapy change event.

C. Package Deployment

Referring back to FIG. 11, various systems and methods exist for deploying packages to medical devices from a medical device server. The packages deployed may include firmware upgrades, maintenance information, new or changed parameters for therapies, or other software upgrades or changes to the medical devices in a medical device network. In a possible embodiment, a package can be used to reprogram the medical device to which it is sent with any of the possible types of package data. Medical devices capable of receiving package data indicate this capability in the main table 1102 and package tables 1108. The main table 1102 indicates the capability of the device to receive a package, and the package tables 1108 include information related to the current package information stored at the medical device for use in operation of the medical device. Package delivery, as discussed in greater detail below, occurs in response to a message, and is initiated using the package data identifier in the event response tables 1910-2410 to indicate to the medical device that a package is available for delivery.

Figure 25:
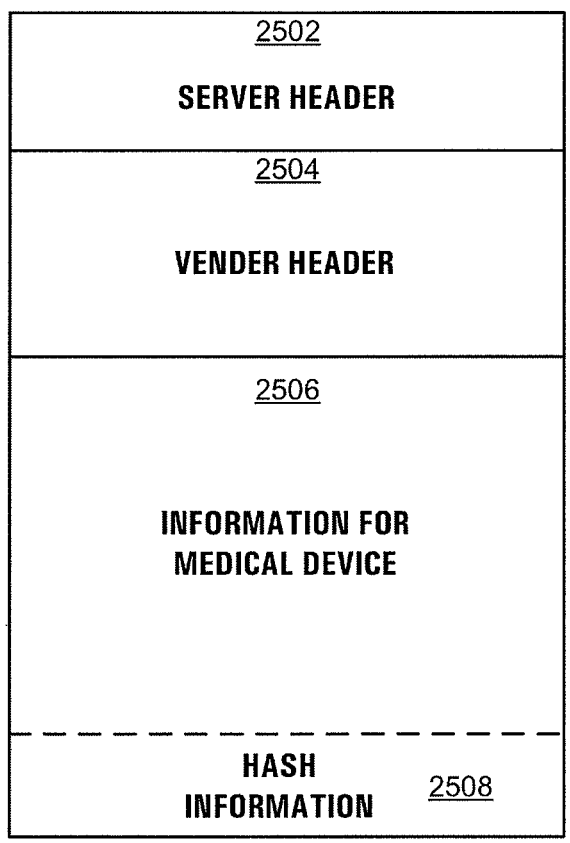
FIG. 25 is a diagram of a data packet formatted for transmission from a medical device server to one or more medical devices.

Referring now to FIG. 25, an example structure of a package 2500 used in deployment of information to a medical device is shown. The package 2500 includes a server header 2502, a vendor header 2504, and information 2506 to be delivered to the medical device. The server header 2502 is the portion of the package understood by the medical device server. The server header 2502 is in a common format to all packages, and contains identification information related to the type of device configured to receive the package, as well as the source of the package. Additional information, such as package size, encryption format, or encryption key location information may be included in the server header 2502 as well. In one embodiment, the server header 2502 is a 256 byte block incorporated into the package.

The vendor header 2504 contains vendor specific information related to use of the package within the medical device receiving the package. The vendor providing the package to the medical device server is generally the manufacturer or maintenance company associated with the medical device intended to receive the package, so the vendor will format the vendor header 2504 in a manner understandable to the medical devices it manufactures. The vendor header generally includes information related to the size of the information 2506, as well as the location of encryption information 2508 within the information. The encryption information 2508 can be used by the medical device to decrypt the information, which is generally stored in the medical device server in an encrypted form.

The information 2506 generally includes any software to be transferred from the medical device server to a medical device, such as a firmware upgrade, a file including therapy parameters, or other binary data. The package delivery system 2500 is not dependent upon the specific format of the vendor header 2504 or the information 2506. The information 2506 is generally stored in an encrypted form on the medical device server. When transferred to a medical device, the information 2506 is decrypted by the medical device by locating the encryption information 2508 based on information in the vendor header 2504.

Figure 26:
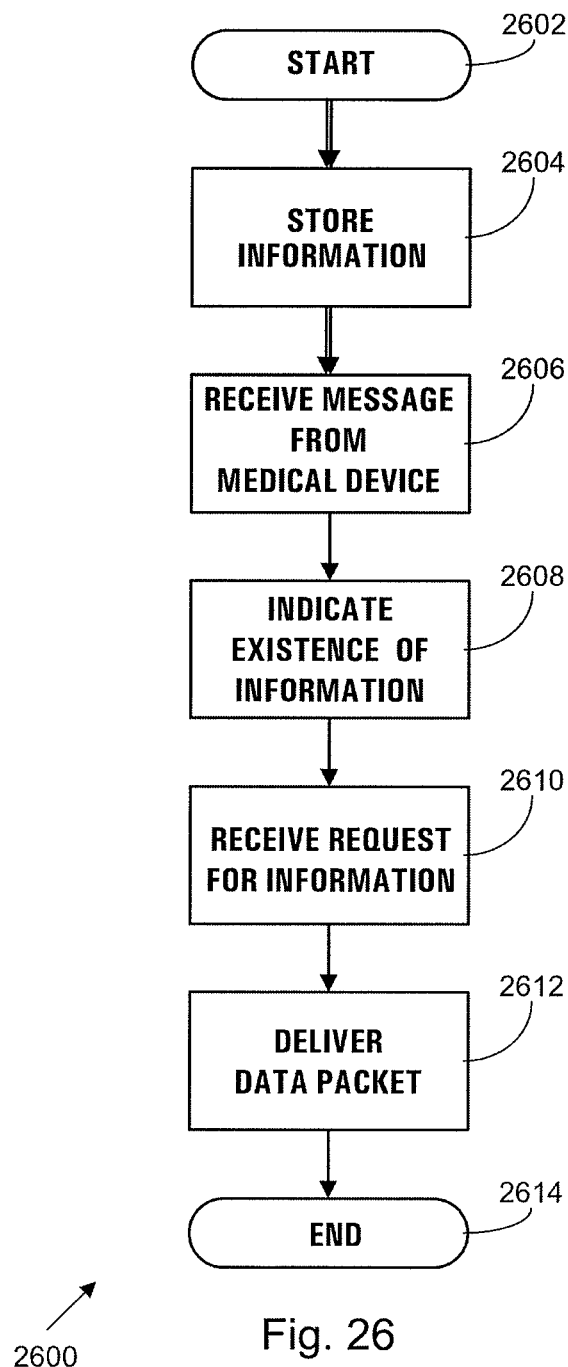
FIG. 26 is a flowchart of methods and systems for delivery of the data packet of FIG. 25.

FIG. 26 shows systems and methods for deploying package data from a medical device server to medical devices. The system 2600 is configured to distribute a package, such as the package 2500 of FIG. 5, to a medical device in response to a message received from the medical device.

Operational flow within the system 2600 commences at a start module 2600, which corresponds to receipt of package information from a vendor of a medical device, an administrator of the medical device, or another entity having familiarity with the operation of the medical device. A storage module 2604 stores the received package in the medical device server. The storage module 2604 can also set an alert or other variable for a medical device such that the next time the medical device communicates with the server, an indication of the existence of the package is included in the response to the medical device. In one embodiment, the storage module 2604 encrypts the package while stored on the medical device server or back office components, and either the medical device server or the medical device itself decrypts the message when the package is to be used or transmitted. In a further embodiment, the storage module 2604 leaves the package unencrypted when it is stored on the medical device server or back office components.

A message receipt module 2606 receives at the medical device server a message from a medical device. The message may be any of a number of types of messages, such as the power, maintenance, alarm, telemetry, therapy, or therapy change event messages described above in FIGS. 19-24. Additional message types are possible as well.

An indication module 2608 indicates to the medical device that a package is intended for delivery to that device. In one embodiment, the indication module 2608 sets a parameter in a message response indicating the existence of a package. For example, the indication module 2608 can set a parameter in the package metadata included in the event response messages 1910-2410 of FIGS. 19-24. Additional methods of indicating the existence of a package are possible as well, such as transmission of a specific message related to package deployment, a package request by the medical device, or other methods.

Figure 27:
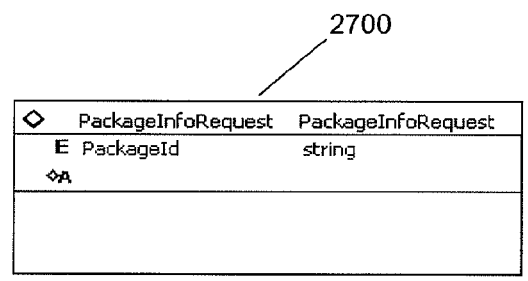
FIGS. 27-32 are data models including metadata useable to facilitate delivery of data packets to medical devices from a medical device server.
Figure 29:
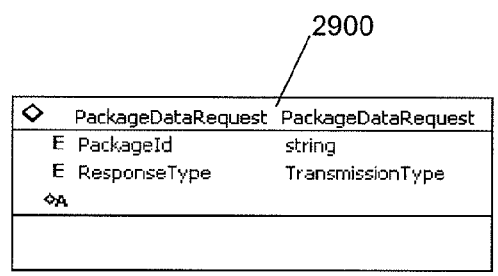
Figure 31:
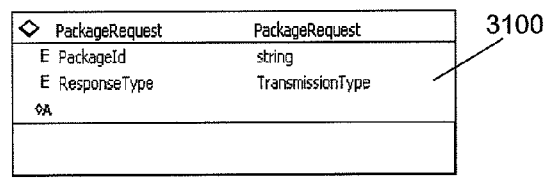

A request module 2610 receives a request from the medical device to receive the package. The request module 2610 may include one or more steps of requesting information about the package to verify at the medical device that the package should be accepted. In a possible embodiment, the request module 2610 transmits a package information request message, using metadata as shown in FIG. 27. In such an embodiment, the request module 2610 optionally also transmits a package data request message separate from the package information request message, the package data request message transmitted following receipt of package information describing the package contents from the medical device server. In further embodiments, the request module 2610 receives a request as shown in FIG. 29 or 31.

Figure 30:
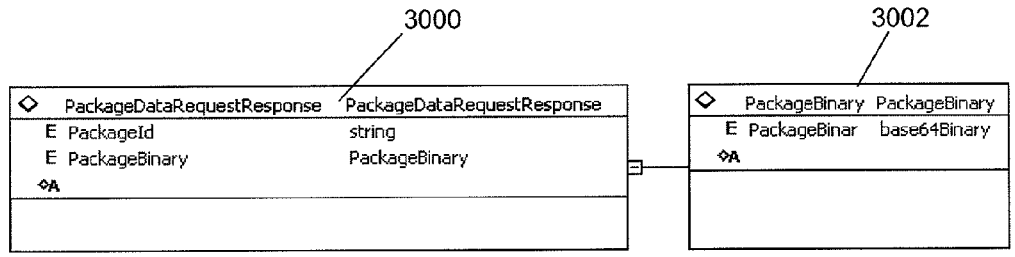
Figure 32:
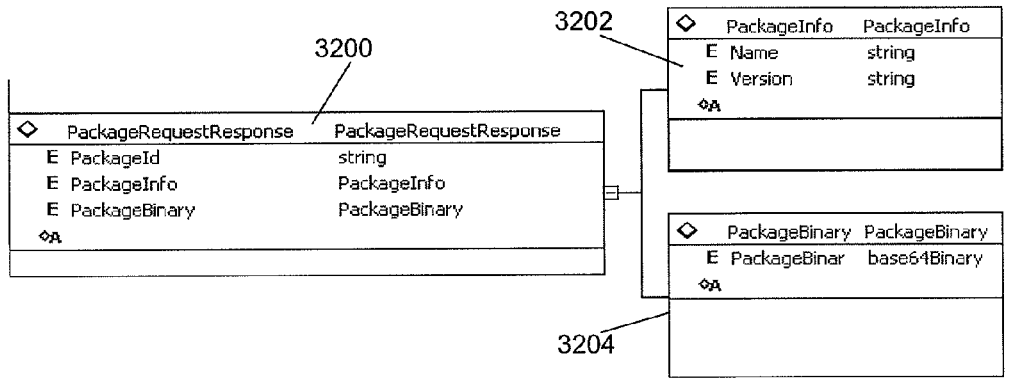

A delivery module 2612 delivers the requested package to the medical device. The format of the package delivery message can be as shown in FIG. 30 or 32. Operational flow terminates at an end operation 2614, which corresponds to completion of the package transmission to the medical device.

FIGS. 27-32 show schema including metadata used in messages and tables in a medical device network, such as the one shown in FIG. 1, to deploy packages from a medical device server to a medical device. The schema display various request and response scenarios in which a medical device requests delivery of package information and receives the requested information in response. One or more messages may be sent between the medical device and the medical device server prior to delivery of the package and its enclosed data.

FIG. 27 shows a package information request table 2700 including metadata used to request information about a package that is available to be deployed to a medical device. The medical device is notified of an available package based on a previous response from the medical device server, as reflecting information in the main table 1102 or package tables 1108 related to that device in the medical device server. The metadata in the table 2700 includes a package identifier, which is used by a medical device to identify the package and request information about its contents. Additional metadata related to the package may be included in the table 2700 and message from the medical device as well.

Figure 28:
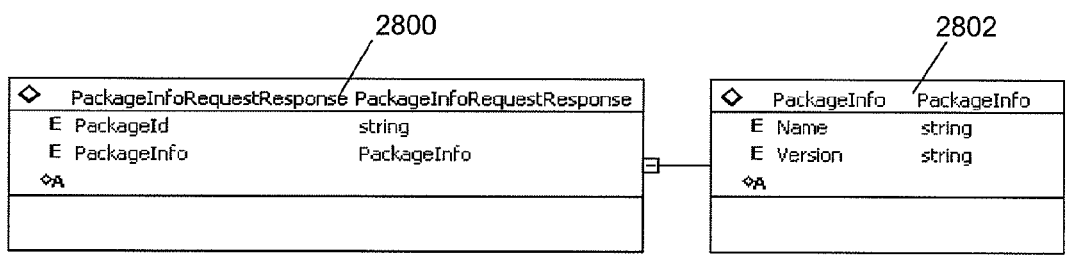

FIG. 28 shows a package information request response table 2800 including metadata used in describing a package available to be deployed to a medical device. The metadata in the table 2800 includes the package identifier, corresponding to the package identifier in the package information request table 2700, and also includes package information metadata. The package information metadata links to a package information table 2802, which contains name and version metadata. Values associated with the name and version metadata describe the package, such that the medical device can determine whether to request deployment of the package.

FIG. 29 shows a package data request table 2900 including metadata used in requesting package data from a medical device server. The package data request table 2900 includes package identifier and response type metadata. The package identifier represents a unique identifier for the package available for deployment to the medical device. The response type represents an identifier indicating the desired delivery format of the package data. In one embodiment, the package data can be delivered to the medical device in either a plain text format or using an xop format.

FIG. 30 shows a package data request response table 3000 including metadata used in deploying a package to a medical device. The metadata included in the package data request response table 3000 includes a package identifier and a package binary data field. The package identifier identifies the package referred to in FIG. 29, and the package binary data field denotes the binary data representing the package being delivered to the medical device. The package binary data field can optionally link to a separate package binary data table 3002 containing the package binary data for delivery to a medical device. In one embodiment, the package delivered to the medical device is the package 2500 of FIG. 25.

FIG. 31 shows a package request table 3100. The package request table 3100 corresponds to the package data request table 2900 of FIG. 29 combined with the package information request table 2700 of FIG. 27. The package request table 3100 can be used by the medical device in an instance in which the medical device does not need to validate the package information prior to downloading the package. The package request table 3100 includes a package identifier and a response type, similar to the package data request table 2900, but indicates by requesting the entire package that package information and package data messages need not be separated.

FIG. 32 shows a package request response table 3200, representing the schema of a message from the medical device server sent in response to a message of the form reflected by the package request table 3100 of FIG. 31. The package request response table includes package identifier, package information, and package binary metadata. The package information metadata links to a package information table 3202 containing name and version metadata associated to the package data. The package binary metadata links to a package binary table 3204, which includes metadata corresponding to the package to be deployed to the medical device.

D. Time Management

Figure 33:
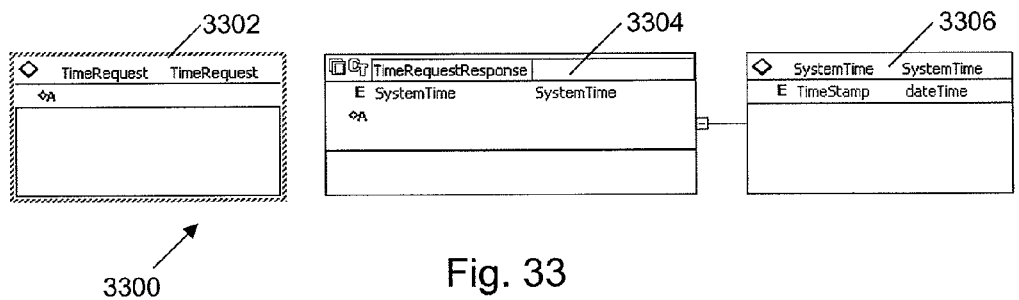
FIG. 33 is a schematic diagram including metadata useable to synchronize time within a medical device network.
Figure 34:
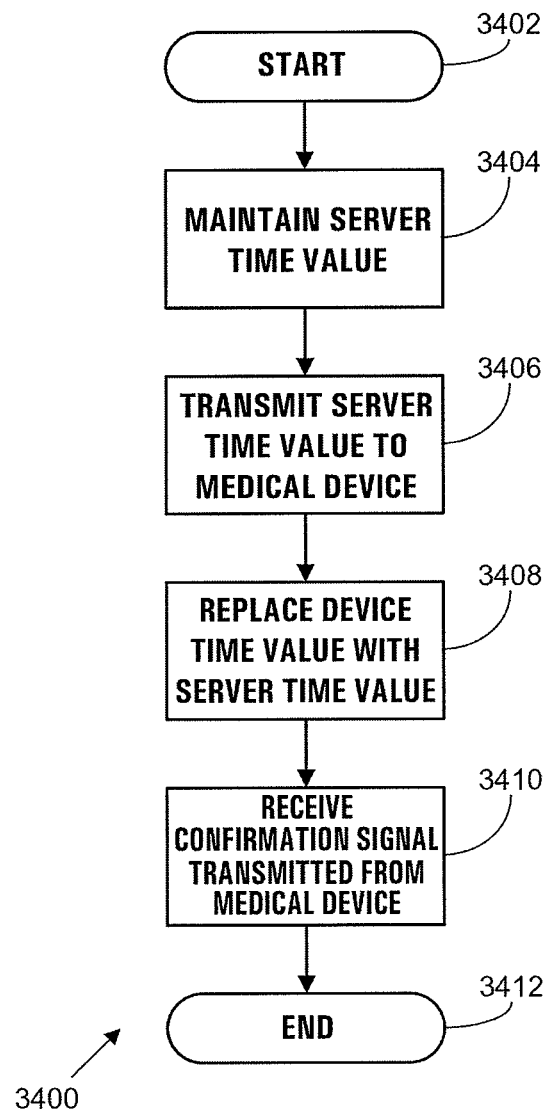
FIG. 34 is a flowchart of methods and systems for synchronization of medical devices in a medical device network.
Figure 35:
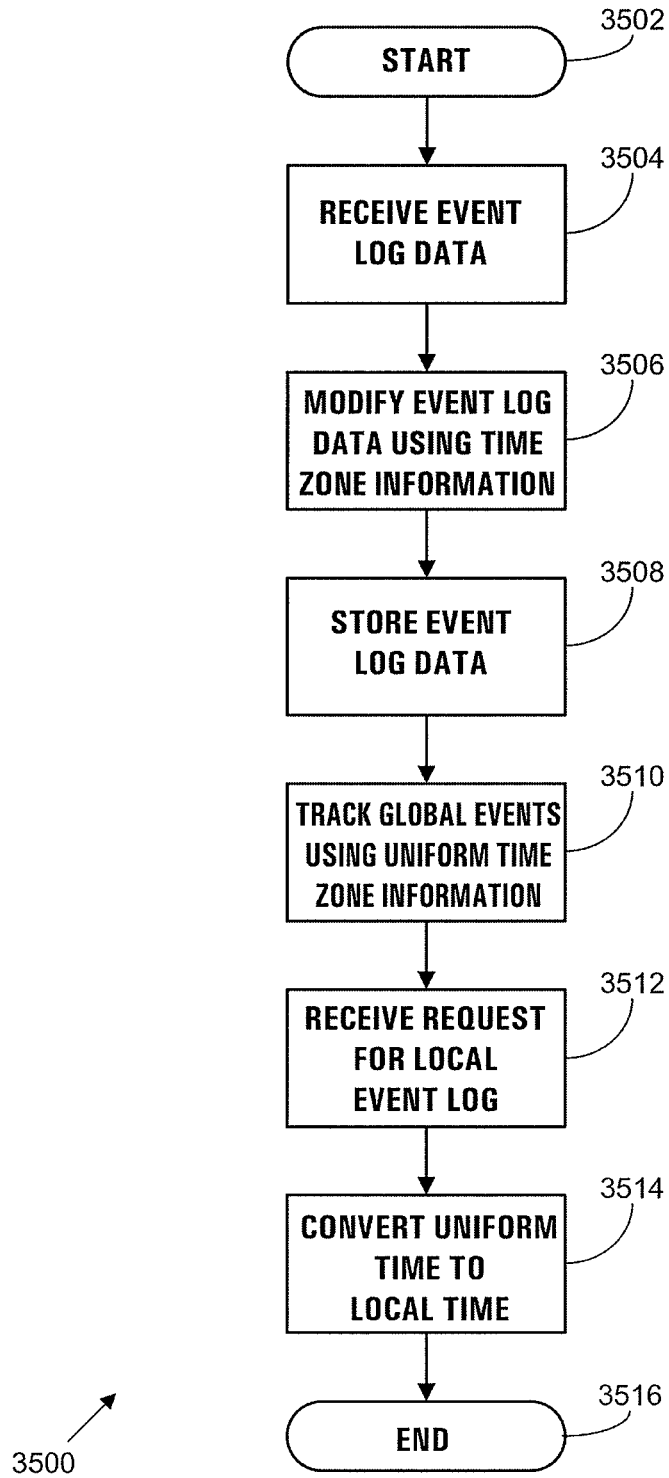
FIG. 35 is a flowchart of methods and systems for time adjustment of event log data.

Referring now to FIGS. 33-35, systems and methods for time management in a medical device network are shown. Because the medical device network can vary in size or configuration, the time management systems described are configured to extend across various business entities, various locations, and various time zones. The systems and methods described provide a uniform way to synchronize time tracking in medical devices and a medical device server located in one or more locations or time zones.

FIG. 33 shows a time messaging schema 3300 useable to track medical device time at the medical device server, and also transmit time synchronization messages between a medical device and a medical device server. The time schema 3300 includes a time request table 3302, a time request response table 3304, and a system time table 3306. The time request table 3302 optionally includes no metadata, but represents a time request response sent from a medical device to the medical device server for synchronization of the medical device time with the time stored in the server or back office components. The time request response table 3304 includes system time metadata, associated with the system time value stored on the medical device server. The system time metadata optionally links to a system time table 3306, which contains a time value useable to synchronize the time of the medical device with the time received from the medical device server. Additional metadata or other information useable to assist in time synchronization can be used as well.

FIG. 34 shows methods and systems for time synchronization of medical devices and a medical device server within a medical device network. Operational flow in the system 3400 commences at a start operation 3402, corresponding to initial operation of the medical device network. A server time maintenance module 3404 maintains a global time value in the server that is to be used to synchronize the time values of the medical devices communicatively connected thereto.

A server time transmission module 3406 transmits the server time to one or more medical devices in the medical device network. In one embodiment, the server time transmission module 3406 transmits the server time value to a medical device in response to a request message from that medical device. In such an embodiment, the request message may be of a form shown in the time request table 3302 of FIG. 33, above.

In a further embodiment, the transmission module 3406 converts the server time value to a localized server time value based on the time zone of the location of the medical device. This conversion may take place if the server resides in a different time zone from the medical device. The server and medical device thereby have a synchronized time value that is converted to the appropriate time zone. One possible implementation of this embodiment converts all times to the Universal Time Protocol upon transmission from the server, and the destination medical device reconverts the time value to the local time of that destination device's location. Other time zone conversions, such as from the local time of the medical device server to the local time of the medical device, are possible as well.

A replacement module 3408 replaces the device time in the medical device with the server time value received from the medical device server. The replacement module 3408 uses the time-adjusted server time value, configured to be used at the location of the medical device. An optional confirmation module 3410 sends a confirmation message to the medical device server indicating that the medical device is successfully synchronized to the server, allowing the server to track which medical devices have been successfully synchronized with the server. Operational flow terminates at an end operation 3412, corresponding to completion of the time synchronization process.

Referring now to FIG. 35, methods and systems for synchronizing event log data are disclosed. The system 3500 accommodates event log data received from medical devices located in different locations in a plurality of time zones. The event log data is configured such that the local time stamp of the event log data represents the time zone in which that device resides, so event logs from different time zones having the same time stamp in actuality occurred at different times. The system 3500 compensates for this discrepancy when storing event log data, and also when providing it to users for review. Operational flow within the system 3500 commences at a start operation 3502, corresponding to initial communication of event data from medical devices to the medical device server.

A receipt module 3504 corresponds to the medical device server receiving event log data from one or more of the medical devices. As described above, the event log data includes various details regarding various types of events, such as therapy events, alarm events, maintenance events, telemetry events, or other types of events, each of which are associated with a time stamp reflecting the current time value of the medical device, reflecting the local time zone of that device. A time zone modification module 3506 converts the time stamp information from the local time zone of the medical device to a constant time zone. In one embodiment, the time zone modification module 3506 converts the time stamp to the Universal Time Protocol (UTP). A storage module 3508 stores the converted time stamp and associated event log data in the medical device server or back office components.

An optional global tracking module 3510 tracks global events using the uniform time zone information. For example, a user desiring to track events that occur at single instantaneous moment across all time zones can track global events using the Universal Time Protocol to maintain a standard time across all time zones. The user sends a request for event log data related to the global events stored on the server, and receives event log information with a time stamp having constant time zone information.

A request local event module 3512 receives a request for local event data, including types of event data associated with the time zone in which the event occurs. Examples of time zone specific events can include events timed to occur at the beginning or end of a shift at a hospital, or other local events. The request local event module 3512 generates a query for the event data requested, and returns results including event log data. A conversion module 3514 converts the uniform time zone information to local time zone information based on the location of the medical device from which the event log data was recorded. The conversion module 3514 optionally generates a report from the event log data for distributing to a requesting user, including the compensated local time event log. Operational flow within the system 3500 is terminated at an end operation 3516, which corresponds to completion of the conversion module 3514.

IV. Remote User to Server Communication

Referring now to FIGS. 36-66, a generalized web service architecture is disclosed which manages user access to a medical device server in a medical device network, such as the one shown in FIG. 1. The web service architecture allows remote user to server communication, to provide data access and programming capabilities related to medical devices in the medical device network of FIG. 1. For example, users can perform administrative tasks, administer software updates to medical devices, access event and operational records, perform maintenance, change therapies, and view near real-time operation of the medical devices while remotely located from the devices. These functions, and others, are described below.

Figure 36:
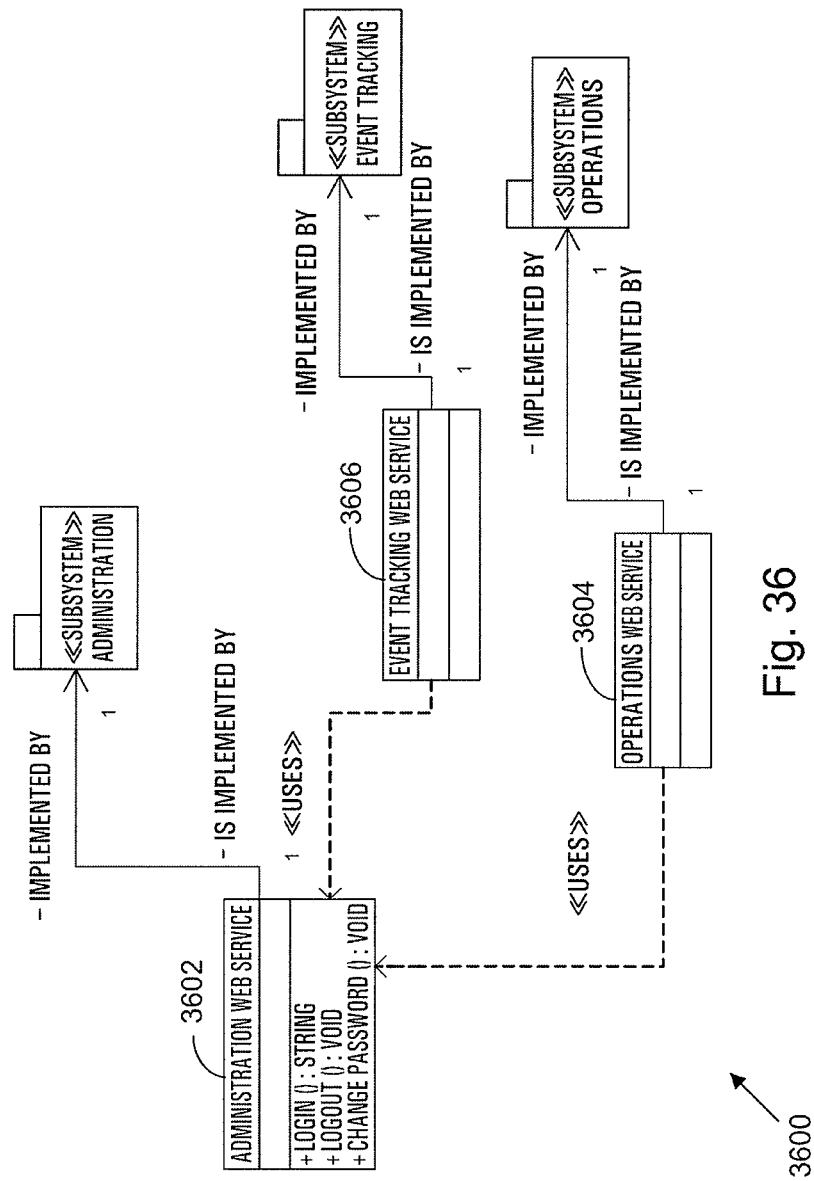
FIG. 36 is a block diagram of functional units of a medical device server, according to a possible embodiment of the present disclosure.

FIG. 36 shows an overall web service architecture 3600, shown as a subsystem of the possible software architectures of the medical device network in FIGS. 3-4. The web service architecture includes various web modules or services configured to validate users and provide access to data stored on the medical device server. In a possible embodiment, the web service architecture is implemented in a .NET architecture using Internet Information Server, by Microsoft Corporation.

The web service architecture 3600 includes an administrative web service 3602, an operations web service 3604, and an event tracking web service 3606. The administrative web service 3602 validates users of the medical device server, and includes functional interfaces for logging in, logging out, and changing a user password. The administrative web service 3602 tracks information related to products, customers, contact information, medical devices associated with the customers, user accounts associated with a customer, and other variables. The administrative web service 3602 uses this tracked information to validate specific users, each of whom is associated with a specific health care facility, referred to in the administrative web service as a customer. A specific implementation class of the administrative web service 3602 is described in Part IV.A, below.

The operations web service 3604 provides access to operational data of the medical devices, such as operational data regarding therapy delivery or monitoring data. The operations web service 3604 tracks the various therapy states occurring in a medical device, and enables a messaging sequence that can occur to trigger or track a therapy event in a medical device. A specific implementation of the operations web service 3604 is described in Part IV.B, below.

The event tracking web service 3606 tracks various event data occurring in a medical device, such as telemetry data received by a medical device server. The event tracking web service 3606 enables users to view near-real time activity of a medical device while located remote from the medical device, and allows the user to determine the on-line status of the medical device. A specific implementation of the event tracking web service 3606 is described in Part IV.C, below.

A. Administration

Figure 37:
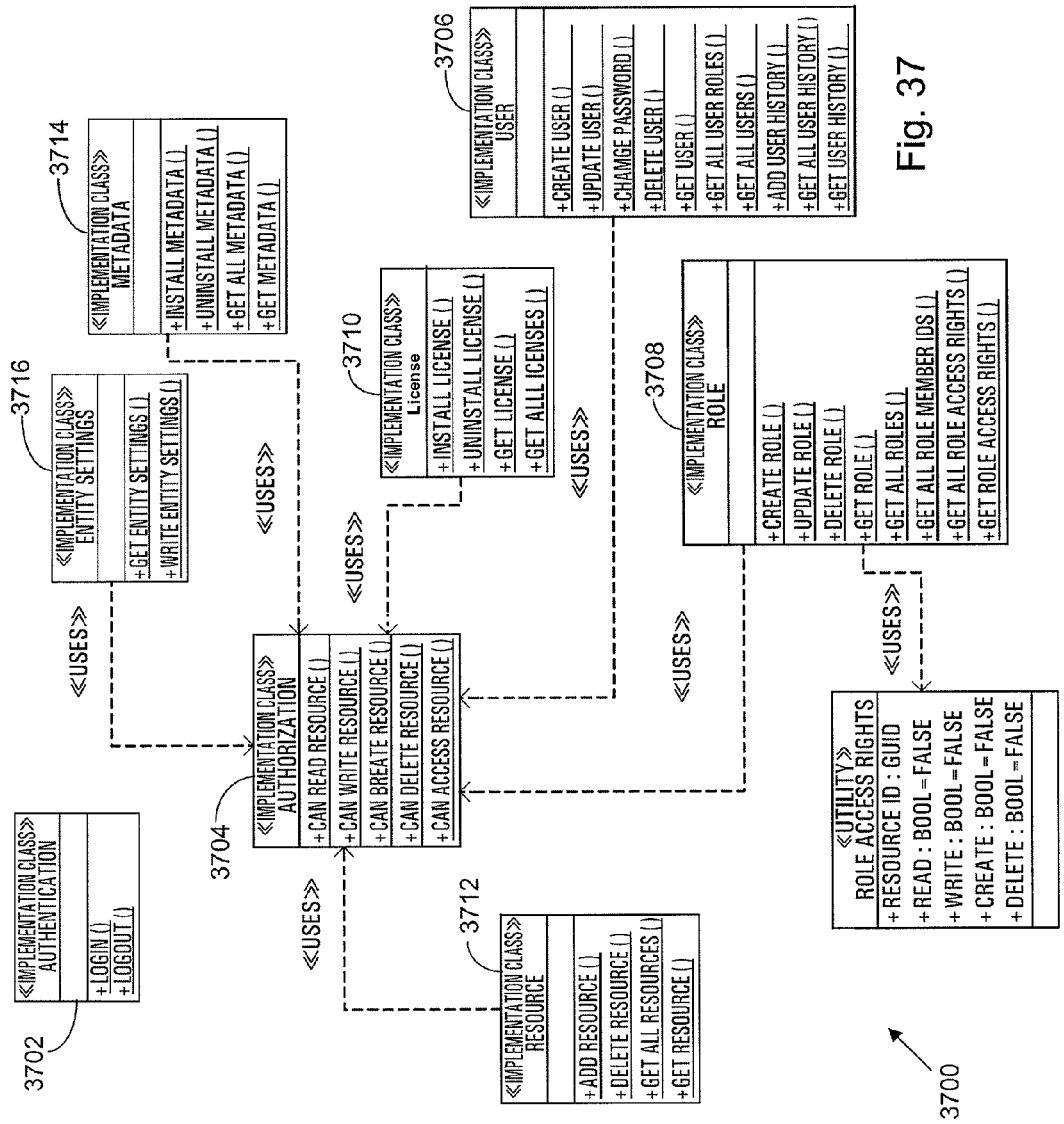
FIG. 37 is a block diagram of medical device server administration systems.

Referring now to FIGS. 37-41, systems and reports for definition and use of an administrative web service are shown. FIG. 37 shows an exemplary class structure defining an administrative web service 3700. The administrative web service 3700 provides a possible embodiment of the administrative web service 3602 of FIG. 36, and is accessible via any of a number of user interfaces, such as the administration web forms 324 of FIG. 3. The administrative web service 3700 includes an authentication class 3702, an authorization class 3704, a user class 3706, a role class 3708, a license class 3710, a resource class 3712, a metadata class 3714, and an entity settings class 3716. Each of the classes includes a number of functions remotely accessible via the internet and web-based user interfaces to perform administrative tasks. Functionality of the various classes is described below.

The authentication class 3702 provides the initial access to the administrative web service 3700, and includes login and logout functionality. The authorization class 3704 includes a variety of resource control functions to ensure that two users are not reading from and writing to the same data concurrently, or otherwise causing data conflicts. The resource control functions incorporated into the authorization class 3704 include read, write, create, delete, and access permission functions. Other functions may be incorporated into the authorization class 3704 as well.

Each of the other classes link to the authorization class 3704, and each requests read or write access to the data protected by the authorization class 3704. The user class 3706 allows the system to perform various user administration tasks, such as creating new users, editing user information, changing passwords, deleting users, defining user roles, and retrieving user histories. Other functions are possible as well. The role class 3708 defines roles assignable to users, and includes the ability to create, update, delete or retrieve various roles defined in the administration data. Roles may correspond to various classes of individuals who can access data managed by the medical device server and back office components, such as doctors, nurses, or healthcare administrators. Roles may also correspond to the various entities with which the individuals are associated.

The license class 3710 defines licenses installed into the system to control the number of users able to log in at once, as well as to define usage models for various accounts. For example, a particular account may allow only a limited number of individuals to view telemetry data or to access therapy records at once, or may define a way of charging a customer for tracked usage of the medical device server or other back office components.

The resource class 3712 allows an administrator to add and delete resources, which correspond to the specific functional areas of the medical device server. The metadata class 3714 provides the underlying functionality for installing metadata into either the administration system, such as custom metadata corresponding to a newly introduced medical device, or into a newly introduced medical device itself. Exemplary interfaces for installation of metadata are shown below in FIGS. 42-43. The entity settings class 3716 allows writing and retrieval of entity settings. Additional administrative functionality, including additional classes, may be incorporated into the administrative web service 3700 as well.

FIGS. 38-41 display sample administrative reports accessible to a user. The administrative reports of FIGS. 38-41 correspond to the reports 326 shown in FIGS. 3-4, and are derived from information stored in the data warehouse 322 related to administrative events logged by the medical device server. In a possible embodiment of the present disclosure, the various reports are generated using SQL Server Reporting Services, by Microsoft Corporation. Other reporting and business intelligence software may be used as well.

FIG. 38 displays an administration tracking event report 3800. The administration tracking event report displays detailed information regarding administration events, such as user access and connection to the medical device server. The number and contents of entries in the report correspond to data from the administration data 316 of FIG. 3 that match the query presented to the administrative web service. The administration tracking event report includes time and date information 3802, application information 3804, and message information 3806. Additional information, such as the code information, time zone indicator, and other information can be optionally included in the report 3800.

The time and date information 3802 display the time stamp information related to the event tracked by the administrative module. The time and date information 3802 display on the report in varying formats, depending upon whether a user chooses a local time zone option or a GMT normalized time option. In the report 3800 shown, the local time zone option is selected.

The application information 3804 indicates the service or handler accessed, and the message 3806 indicates the action taken with respect to that service or handler. In the example shown, exemplary connection events are shown for two medical device servers, labeled "MDS:Mds01" and "MDS:Mds02".

FIG. 39 displays a security event report 3900. The security event report 3900 corresponds generally to the administration tracking event report 3800, but includes events related to security of the medical device server rather than access to it. The security event report 3900 includes time and date information 3902, application information 3904, and message information 3906, each of which have the same functionality as in the administration tracking event report 3800.

Figure 40:
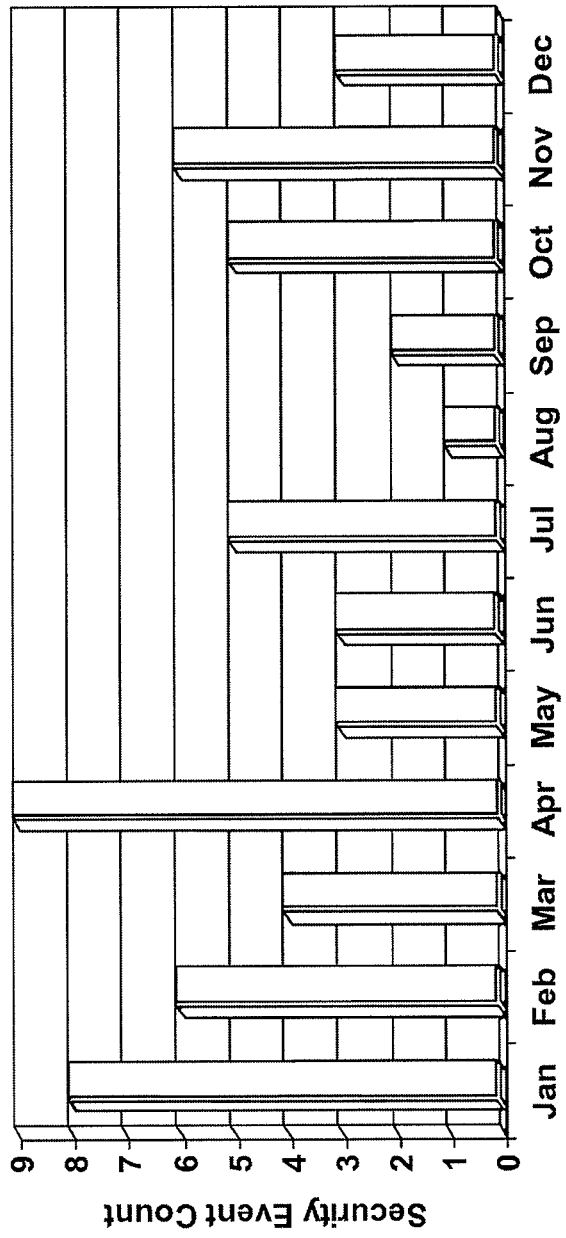
FIG. 40 is a sample security event trending report accessible from a medical device server.

FIG. 40 displays a security event trending report 4000. The security event trending report 4000 displays a chart of security related events over time. In the embodiment shown, the security event trending report 4000 displays a bar chart showing the frequency of security events by month. Other configurations displaying trends in security events are possible as well.

FIG. 41 displays a user history report 4100. The user history report displays a chronologically ordered list of events logged regarding one or more users. Each entry in the list includes time and date information 4102, a sorting code 4104, a username 4106 corresponding to the active user, and a message 4108 related to the action taken by that user. An optional details entry 4110 displays additional information associated with the history information, in raw form, such as the session key, location, name, location, or other activities occurring in the user history.

1. Metadata and Package Deployment Interfaces

Referring now to FIGS. 42-50, various methods of programming the medical device server and medical device with metadata, firmware, or other binary data are shown. FIGS. 42-46 display administrative forms useable to perform various administrative tasks in the medical device server, such as providing or removing metadata or packages, intended for configuration of the medical device server or medical devices, respectively. The administrative forms can correspond to forms generated by the administrative applications 324 of FIGS. 3-4. FIGS. 47-50 display reports displaying the results of installation of the metadata and packages, and are a subset of the reports 326 available from the data warehouse 322 in FIGS. 3-4.

Figure 42:
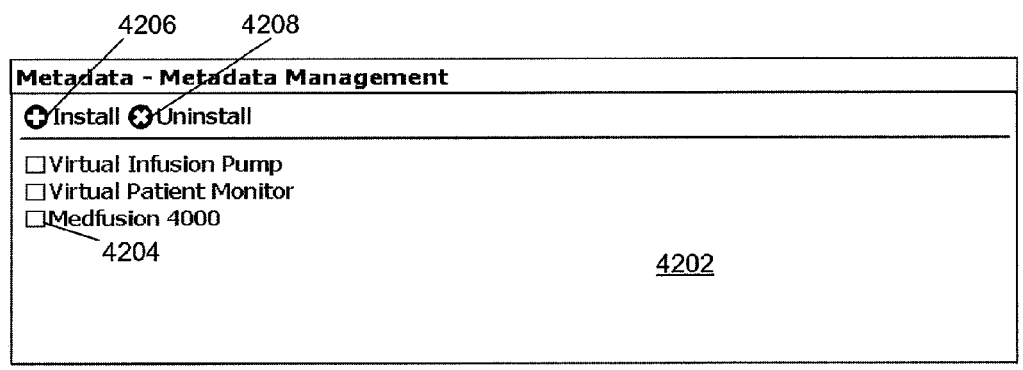
FIG. 42 is a user interface for management of medical device metadata.
Figure 43:
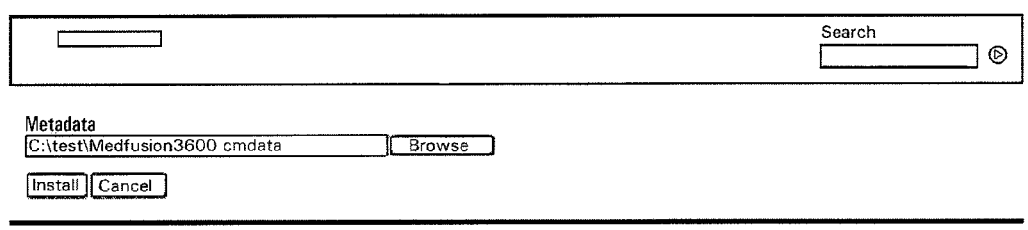
FIG. 43 is a further user interface for installation of medical device metadata.

FIGS. 42-43 display user interfaces configured to allow an administrative user to manage metadata installed into the medical device server, as described above in Parts III.A and III.B. FIG. 42 shows an initial user interface 4200 showing the metadata packages either currently installed into the medical device server or available to be installed. A listing area 4202 lists the packages, in this case displayed as "Virtual Infusion Pump", "Virtual Patient Monitor", and "Medfusion 4000". Check boxes 4204 in the listing area allow user selection of one or more of the installed packages, an install button 4206 installs the packages into the medical device server, and an uninstall button 4208 removes metadata packages from the medical device server.

FIG. 43 displays a metadata installation interface 4300 configured to allow a user to browse for a metadata file and install that file onto the medical device server. The metadata installation interface 4300 appears following selection of one of the types of medical devices present in the system in the user interface 4200, and allows the user to select and install a metadata file associated with the previous selection of metadata using the initial user interface 4200.

Figure 44:
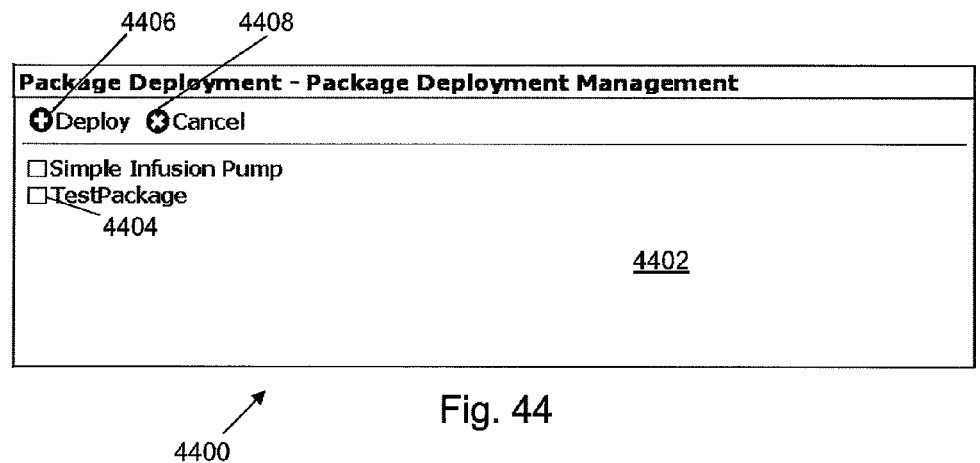
FIG. 44 is a user interface for management of data packet distribution in a medical device network.

FIG. 44 displays a package deployment interface 4400 providing deployment of packages for distribution to one or more medical devices, as described above in Part III.C. The package deployment interface 4400 generally corresponds to the metadata installation interface 4200 of FIG. 42, but relates to software to be installed onto a medical device, rather than into the medical device server. A listing area 4402 lists the packages, in this case displayed as "Simple Infusion Pump" or "TestPackage". Check boxes 4404 in the listing area allow user selection of one or more of the installed packages, a deploy button 4406 deploys the packages into the medical device server, and an uninstall button 4408 removes the packages from the medical device server.

Figure 45:
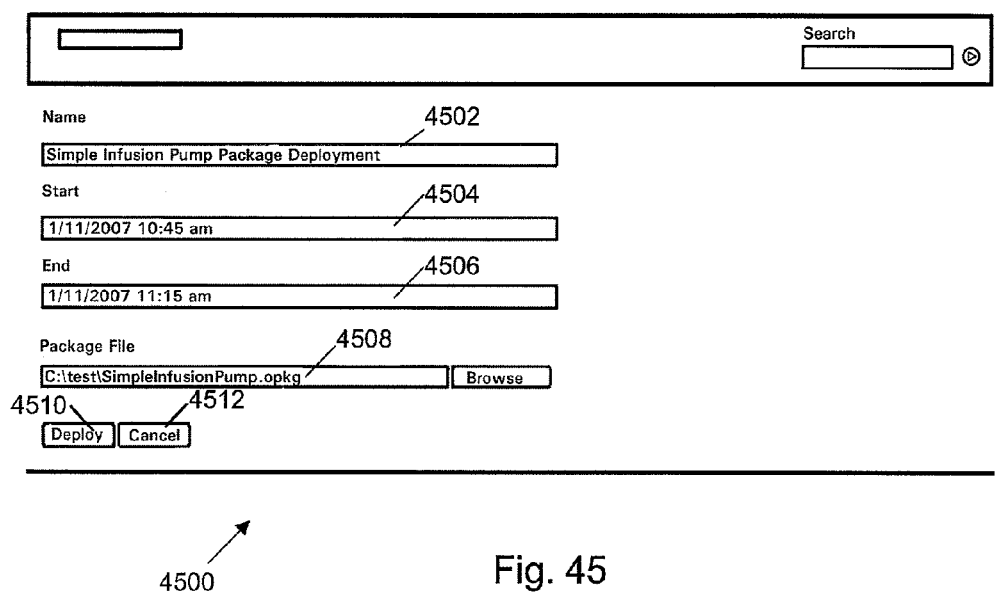
FIG. 45 is a further user interface for deployment of data packets to medical devices in a medical device network.

Upon selection of the deploy button 4406, a user interface 4500 shown in FIG. 45 is displayed. The user interface 4500 allows system administrators to enter a package deployment name into a name field 4502, and also allows the administrator to enter a start time and end time, into start and end fields 4504, 4506, respectively. The user interface further allows the system administrator to select a package deployment file to use in a package deployment file selection field 4508. The system administration presses a deploy button 4510 to deploy the package, or a cancel button 4512 to cancel deployment.

Upon selection of the deploy button 4510, a further user interface 4600 shown in FIG. 46 is displayed to allow user verification that the correct package has been selected for download to medical devices. The user interface 4600 displays package deployment details in a package information field 4502, including the selected start time, end time, and target type as entered in the previous user interfaces 4400, 4500. The user interface 4600 further displays vendor properties in a vendor field 4504, such as the vendor identifier, name, and version of the vendor package.

FIGS. 47-50 display various reports generated from the data warehouse 322 of FIGS. 3-4, as related to metadata-defined event messages or package deployment. FIG. 47-48 relate to message handling and debugging of faulty messages received from a medical device. FIGS. 49-50 display package deployment reports, incorporating records of successful and unsuccessful deployment of software or other binary data to medical devices.

FIG. 47 displays a quarantine report 4700, which displays a chronological list of the quarantined messages received by the medical device server. The quarantine report 4700 includes time and date information 4702, state information 4704, and message information 4706. The time and date information 4702 display the time stamp information related to the quarantine event tracked by the medical device server. The time and date information 4702 display on the report in varying formats, depending upon whether a user chooses a local time zone option or a GMT normalized time option. In the report 4700 shown, the local time zone option is selected.

The state information 4704 relates to the state of the quarantined message, such as whether it is a new message, a released message, or a reinserted message. New messages refer to newly located problematic messages, while released messages correspond to messages which cannot be resolved and must be dropped. Reinserted messages refer to those messages which are reintroduced to the message server in case the medical device is awaiting a response from the server.

The message information 4706 describes the error occurring in the message transfer. Various error messages are possible, generally relating to the ability of the medical device server to understand the message received from a medical device.

FIG. 48 displays a quarantine detail report 4800, which is configured to display the details of a specific quarantined message received by the medical device server. The quarantine detail report includes an error field 4802 including the error information displayed on the quarantine report 4700, and a source field 4804 which displays the metadata and values included in the message, for user debugging or correction of message activity in the medical device server. Additional information can be displayed regarding the quarantined message as well.

FIG. 49 displays a package deployment report 4900 showing package deployments known to the medical device server, with an associated list of medical devices of various types and the status of the package deployment to each of the medical devices. The package deployment report includes one or more package deployment entries 4902, each including name and version information related to the specific package being deployed to that type of device. Each of the package entries includes device sub-entries 4904, each of which relates to a specific device qualifying for the generalized package deployment. The sub-entries each include host name information 4906, physical identification information 4908, notification information 4910, transfer information 4912, and completion information 4914. The host name information 4906 corresponds to the medical device server providing the package to the device. The physical identification information 4908 displays the unique identifier associated with the medical device. The notification information 4910 displays the date and time at which the medical device was notified that the package was available. The transfer information 4912 displays the date and time at which the package was successfully transferred to the medical device. The completion information 4914 displays the full date and time at which the package was successfully applied to the medical device.

Additional information can be tracked for each package deployment. For example, in an instance in which a package fails to deploy, an error indication 4916 displays an indication of an error, and a result of the error.

FIG. 50 displays a package deployment error report 5000. The package deployment error report 5000 provides a detailed event history for the specific packages and corresponding devices for which a package deployment fails. The package deployment error report 5000 displays a title 5002 including the target medical device type and package identifier. The title also optionally displays a name associated with the package deployment.

The package deployment error report 5000 displays time and date information 5004, optional host information 5006, physical identifier information 5008, and message information 5010. The time and date information 5004 indicate when the error in the package deployment occurred. The optional host name information 5006 displays the network name in which the medical device is located. The physical identifier information 5008 includes the identifier associated with the medical device. The message information 5010 displays the message associated with the package deployment error. Additional information regarding the deployment error may be included in the report 5000 as well.

2. Maintenance/Faults

Figure 53:
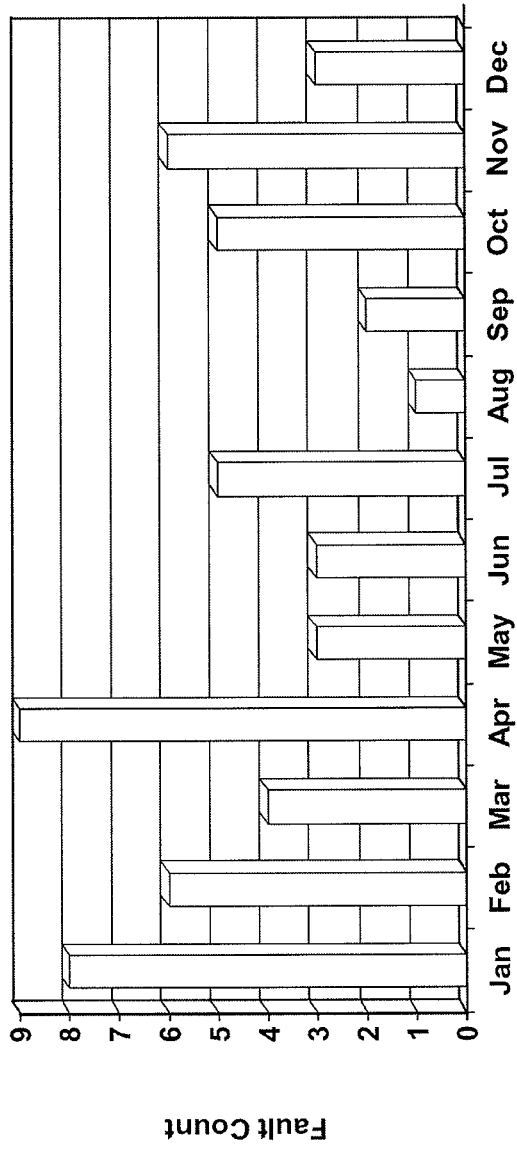
FIG. 53 is a sample medical device fault trending report displaying trends in medical device faults communicated to a medical device server.

Referring now to FIGS. 51-53, reports related to maintenance and faults of medical devices are shown. The reports provide user access to records of maintenance performed on the medical devices as well as information related to medical device failures and trends in those failures. Additional reports related to maintenance or faults may be incorporated as well, and correspond to the maintenance event data collected by the medical device server, as described above in Part III.B. In a possible embodiment, one or more of the reports of FIGS. 51-53 correspond to the maintenance forms 330 of FIGS. 3-4.

FIG. 51 shows a medical device maintenance report 5100 listing maintenance records for various medical devices. The medical device maintenance report 5100 includes type entries 5102 corresponding to various types of medical devices, and device sub-entries 5104 corresponding to specific medical devices. In the embodiment shown, the type entries 5102 are the "MedFusion 4000" and "Titan" entries, while the device sub-entries 5104 are the individual rows within each type.

Within each sub-entry 5104, there exists host name information 5106, physical identifier information 5108, version information 5110, package information 5112, and preventative maintenance date information 5114. The host information 5106 displays the network associated with the medical device. The physical identifier 5108 displays the unique identifier associated with the medical device. The version information 5110 displays one or more version numbers associated with the medical device. The package information 5112 displays packages being used by the medical device. The preventative maintenance information 5114 displays a date at which the medical device is due for preventative maintenance. Additional information can be displayed within each sub-entry 5104 as well.

FIG. 52 shows a medical device fault report 5200. The medical device fault report 5200 displays events related to medical device faults communicated to a medical device server, such as due to a faulty battery, motor, or other mechanical component. The medical device fault report 5200 includes time and date information 5202, host information 5204, physical identifier information 5206, and message information 5208. Use of the information 5202-5208 is analogous to the corresponding elements in the package deployment error report 5000 of FIG. 50, but related to medical device fault events. For example, in the medical device fault report 5200, the message information includes device fault event information, such as motor, battery, or other mechanical faults of a medical device.

FIG. 53 shows a medical device fault trending report 5300. The medical device fault trending report 5300 displays a chart of medical device fault related events over time. The medical device fault trending report 5300 provides users with an indication of repeated errors in a medical device, or other detectable trends in medical device faults. In the embodiment shown, the medical device fault trending report 5300 displays a bar chart showing the frequency of device fault events by month. Other configurations displaying trends in device fault events are possible as well.

B. Operations Web Service: Operation and Control of Therapy States

FIGS. 54-62 disclose various aspects of the operations web service 3604 of FIG. 36. Specifically, the figures show systems, methods, and reports for remote operation of the medical devices in a medical device network. In one possible embodiment, the systems and methods describe tracking of changed therapy parameters in a medical device by tracking original, updated, and final parameters of the medical device.

Figure 54:
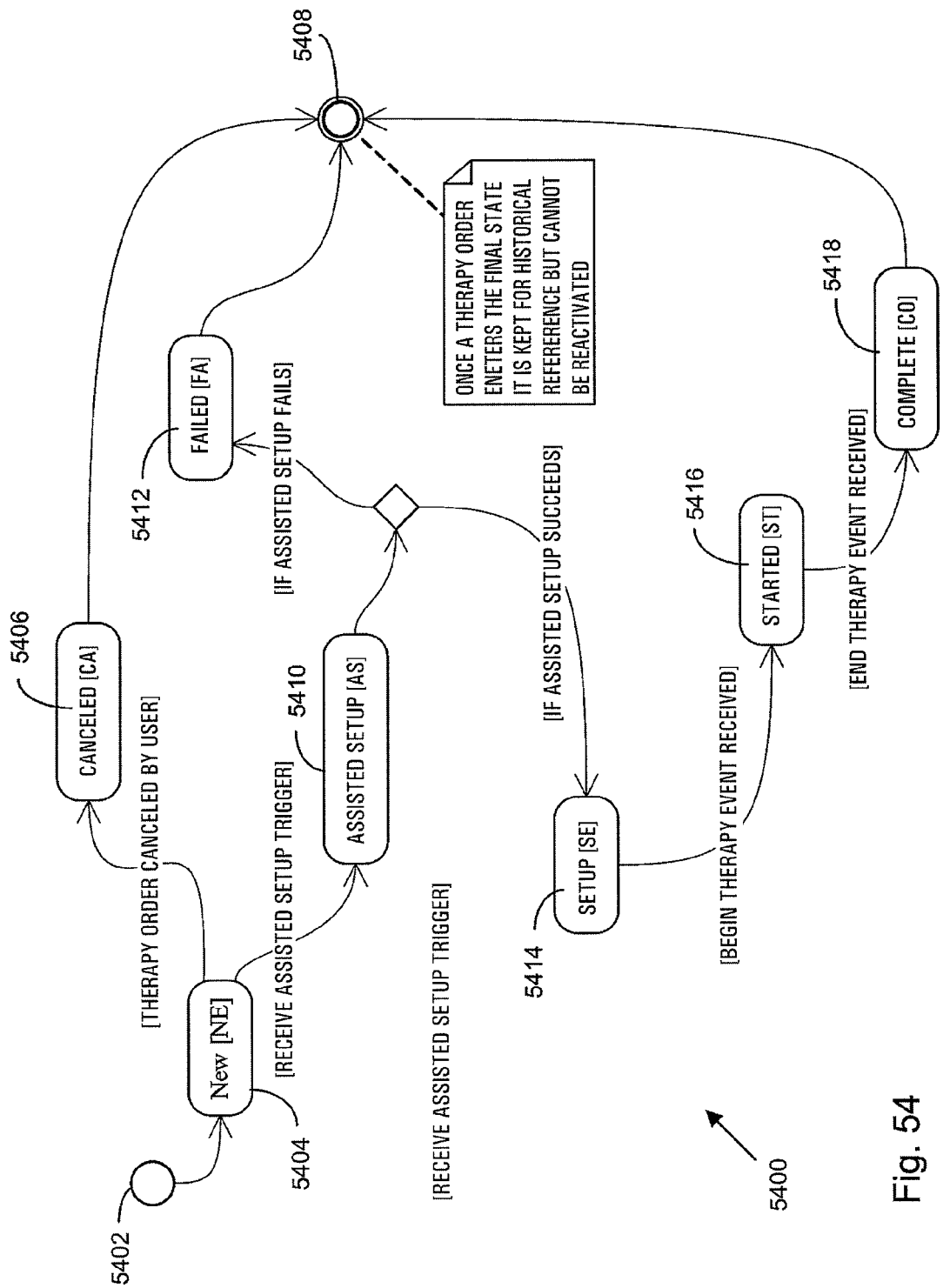
FIG. 54 is a flowchart of methods and systems for communicating parameter changes from a medical device server to a medical device.

FIG. 54 shows a flowchart of methods and systems for tracking therapy order states in a medical device server. Therapy orders refer to commands to a medical device to provide a therapy to a patient. The system 5400 includes states corresponding to the various possible states experienced in the medical device during execution of the therapy order.

Operational flow within the system 5400 commences at a start node 5402, which corresponds to introduction of a new therapy order into the medical device or medical device server. Once the therapy order is introduced, the system 5400 enters a new state 5404, indicating that the therapy order is newly introduced and has not yet been executed by the medical device. When the system 5400 is in the new state 5404, a user has the option to cancel the therapy order. If the user chooses to cancel the therapy order, operational flow in the system 5400 proceeds to a canceled state. 5406. From the canceled state, operational flow proceeds to an end node 5408 corresponding to completion of the therapy module. At the end node 5408, operational flow terminates and therapy delivery events tracked using the medical device server continue to be stored for review by a user.

If the user chooses not to cancel the therapy order while the system 5400 is in the new state, operational flow proceeds to an assisted setup state 5410. The assisted setup state 5410 attempts to assist in setting up the therapy parameters. If the assisted setup is unsuccessful operational flow branches to a failed state 5412. The failed state 5412 stores an error message indicating that the assisted setup process failed. Operational flow proceeds from the failed state 5412 to the end node 5408.

If the assisted setup state 5410 is successful in setting up therapy parameters, operational flow branches to a setup state 5414. The setup state 5414 indicates that the therapy is successfully set up in the medical device, and is ready for delivery to a patient.

A begin therapy event, optionally sent from the medical device server or generated at the medical device, triggers the system 5400 to proceed to a started state 5416, which corresponds to starting the therapy delivery in the medical device. An end therapy event received from the medical device or medical device server causes operational flow in the system 5400 to proceed to a complete state 5418, indicating that delivery of the therapy is complete. Operational flow next proceeds to the end node 5408.

Figure 55:
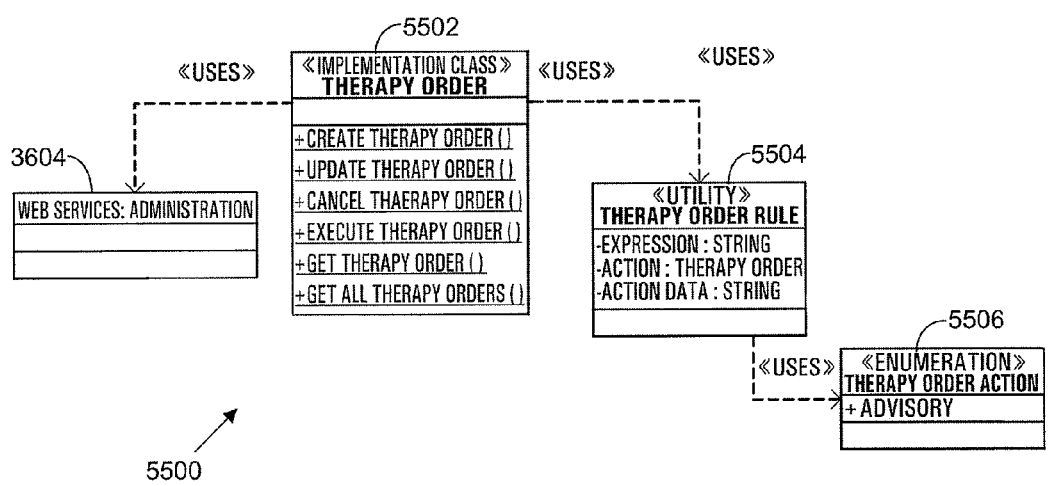
FIG. 55 is a schematic diagram including metadata useable to facilitate therapy-based programming of medical devices from a medical device server.

FIG. 55 shows an exemplary class structure defining a therapy service 5500. The therapy service 5500 illustrates a portion of the functionality of the operations web service module 3604. The therapy service 5500 links to and uses a variety of functions from the administrative web service 3700 of FIG. 37.

The therapy service 5500 includes a therapy order class 5502, a therapy order rule utility 5504, and a therapy order action enumeration 5506. The therapy order class 5502 includes a variety of therapy order operations for starting, stopping, and defining various therapies to be delivered by medical devices in the medical device network in which the therapy service 5500 operates. The therapy order operations include therapy creation, therapy update, therapy cancel, therapy execute, and therapy retrieval operations. Additional therapy order operations can be included in the therapy order class 5502 as well.

The therapy order rule utility 5504 provides expressions and actions related to execution of the therapy order, including various parameters and commands required for execution of the therapy. The therapy order action enumeration 5506 provides advisory messages used during selection and/or execution of a therapy order.

Figure 56:
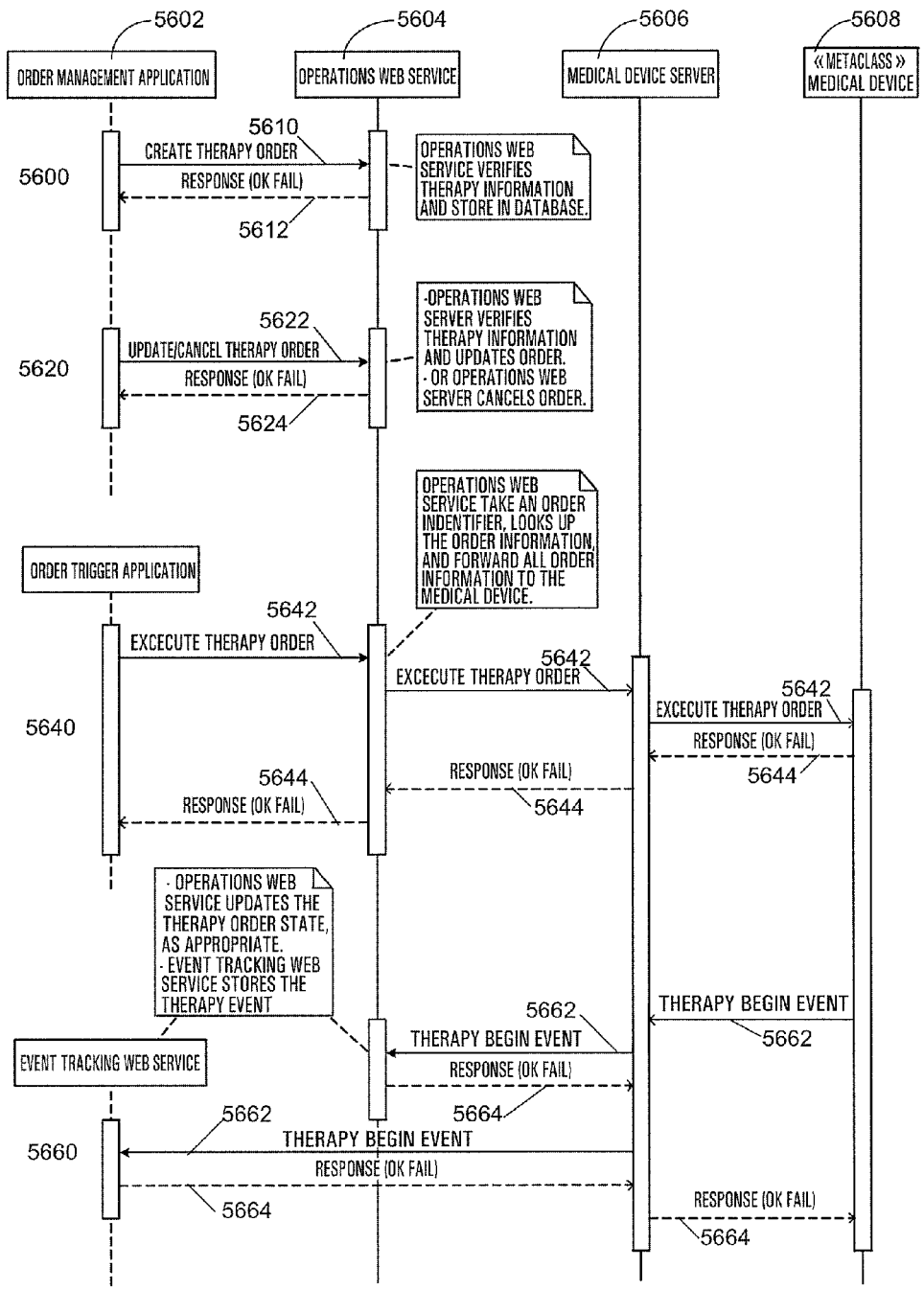
FIG. 56 is an exemplary messaging sequence for therapy-based programming of a medical device.

FIG. 56 displays exemplary message exchange processes 5600, 5620, 5640, and 5660 performed between a therapy order management application 5602, an operations web service 5604 such as the one shown in FIG. 36, a medical device server 5606 as disclosed above in FIGS. 3-4, and a medical device 5608, such as shown in FIG. 2. The therapy order management application 5602 can be any application configured to interface with the operations web service to communicate therapy orders and other messages to the operations service 5604 and medical device server 5608.

A first message exchange process 5600 illustrates the therapy order management application 5602 transmitting a create therapy order message 5610 to the operations web service 5604. The operations web service 5604 verifies the therapy information and stores the therapy order in operations data. The operations web service 5604 also responds 5612 by indicating success or failure of the message.

A second message exchange process 5620 illustrates the therapy order management application 5602 later in time transmitting a therapy order update message or a therapy order cancellation message 5622. The operations web service 5604 verifies the therapy information, and updates or cancels the therapy order according to the message. The operations web service 5604 also responds 5624 by indicating success or failure of the message.

A third message exchange process 5640 occurring after the first message exchange process 5600 illustrates the therapy order management application 5602 transmitting a message 5642 indicating that the therapy order should be executed. The therapy order management application 5602 transmits an execute therapy order message 5642 to the operations web service 5604, which verifies the therapy order and in turn forwards the therapy order message 5642 to the medical device server 5606. The medical device server 5606 relays the therapy order message 5642 to a medical device 5608.

The medical device 5608 transmits a message 5644 indicating the success or failure of receipt of the therapy order message 5642. The medical device server 5606 and operations web service 5604 relay the message 5644 back to the order trigger application 5602.

At a time after the medical device transmits the message 5644, the medical device 5608 initiates a fourth messaging process 5660 in which the medical device transmits a therapy begin message 5662 to the medical device server 5608, indicating that the medical device has begun delivering the therapy to a patient. The medical device server 5608 transmits the message 5662 to the operations web service 5604, which updates the therapy order state. The medical device server also relays the message 5662 to an event tracking web service 5605, such as the one in FIG. 36, to store a therapy delivery event in an event history log. Both the event tracking web service 5605 and the operations web service 5604 transmit response messages 5664 indicating the success or failure of receipt of the therapy begin message 5662.

Additional events triggered by the medical device, such as a therapy completion event or alarm, transmit among the components 5602-5608 analogously to the messaging process 5660. Further, additional messaging schema can be included as well.

Figure 57:
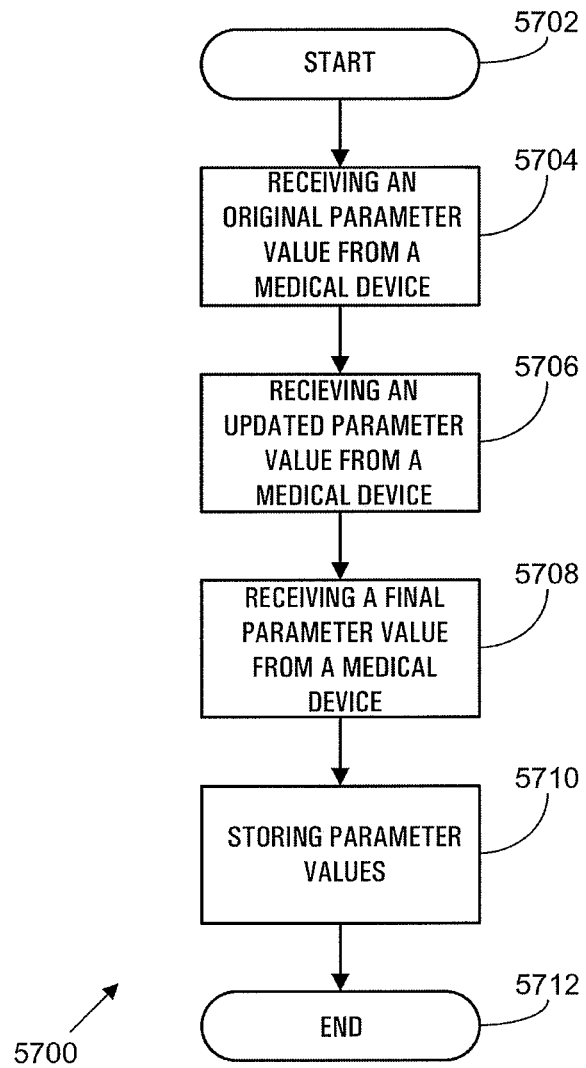
FIG. 57 is a flowchart of methods and systems for tracking changed medical device parameters communicated to a medical device server.

FIG. 57 shows methods and systems for tracking changed parameters in a medical device, such as a medical infusion pump. The system 5700 communicates original, updated, and final parameter values used for operation of the medical device, using metadata as described herein to identify the various changes in parameters. The system 5700 commences at a start operation 5702, which corresponds to initiation of a therapy in a medical device. The therapy initiated in the medical device includes parameters needing parameter values to define various aspects of the therapy. For example, in a therapy delivered by a medical infusion pump, various parameters include basal rates, bolus rates, thresholds, and various other parameters.

An original parameter receipt module 5704 receives an original parameter value from a medical device. The original parameter is a parameter set in a medical device prior to receipt of a different parameter by that device, and can be any type of operational parameter related to delivery of a therapy or monitoring provided by the medical device. An updated parameter receipt module 5706 receives an updated parameter value from the medical device corresponding to a change from the original parameter. The updated parameter value is a new parameter value changing the operation of the medical device. The updated parameter value relates to the same parameter as the original parameter. A final parameter receipt module 5708 receives a final parameter value from the medical device. The final parameter value is the parameter value the medical device will use for therapy and monitoring after the device is reprogrammed with the updated parameter value. The final parameter value may be the same as the updated parameter value, or may be different based on, for example, various hard and soft limits set for parameters within the medical device. In various embodiments, the receipt modules 5704-5708 may occur concurrently or sequentially, and may be included in one or more messages from the medical device to the medical device server.

A parameter storage module 5710 stores the original, updated, and final parameter values in memory of the medical device server or other back office components. Optional additional steps involved in the system 5700 can include comparing the final parameter value received in the final parameter receipt module 5708 with a hard limit or soft limit stored in the medical device server. If the final parameter value exceeds the limit, the system 5700 may trigger an alarm in the medical device server, and optionally communicate that alarm back to the medical infusion pump via a package deployment or other message. In a further embodiment, the alarm is communicated to a medical caregiver associated with the medical device.

Operational flow terminates at an end operation 5712, which corresponds to completion of the change in pump parameter values and storage of the updated pump parameter values in the medical device server or other back office component.

FIG. 58 shows a medical device history report 5800 listing original, updated, and final operational parameter values for a medical device according to the methods and systems of FIG. 57. The medical device history report 5800 includes a medical device label 5802, date and time information 5804, class information 5806, trigger information 5808, message information 5810, location information 5812, and drug information 5814. The medical device label 5802 corresponds to the medical device name for the device whose history is displayed in the report 5800. The date and time information 5804 correspond to the time the various events occurred that are included in the medical device history report. The class information 5806 describes the type and severity of the event. In the case of a therapy change event, the class information 5806 also includes an original value of the changed parameter, the changed value of that parameter, representing the value entered by a user, and a final value of the parameter, indicating the final set value used by the medical device.

The trigger information 5808 displays the trigger associated with the medical device event. In the example shown, an event in an alarm classification has a high level of concern, and includes a warning in the trigger information 5808. However, an event describing a therapy change will not activate the trigger information 5808.

The message information 5810 includes information about the status of the medical device, such as battery life, therapy delivery progress, therapy parameter limits, or physical characteristics of the device. The location information 5812 includes information related to the location of the medical device, such as the department, the facility, and the entity controlling the medical device. The drugs information 5814 includes information about the drug or therapy being delivered by the medical device, and optionally is only included in the information for a therapy change. Additional information about the medical device can be displayed in the medical device history report 5800, based on the information tracked by the medical device server and operations web service.

Figure 59:
FIG. 59 is a sample therapy history report displaying therapy event log data communicated from a medical device to a medical device server.

FIG. 59 shows a therapy history report 5900. The therapy history report 5900 displays the same information as is displayed in the medical device event history report 5800 of FIG. 58, but will only display therapy event information. The therapy history report 5900 includes a medical device label 5902, date and time information 5904, class information 5906, trigger information 5908, message information 5910, location information 5912, and drug information 5914, each of which operate analogously to the corresponding entries in the medical device event history report 5800.

Figure 60:
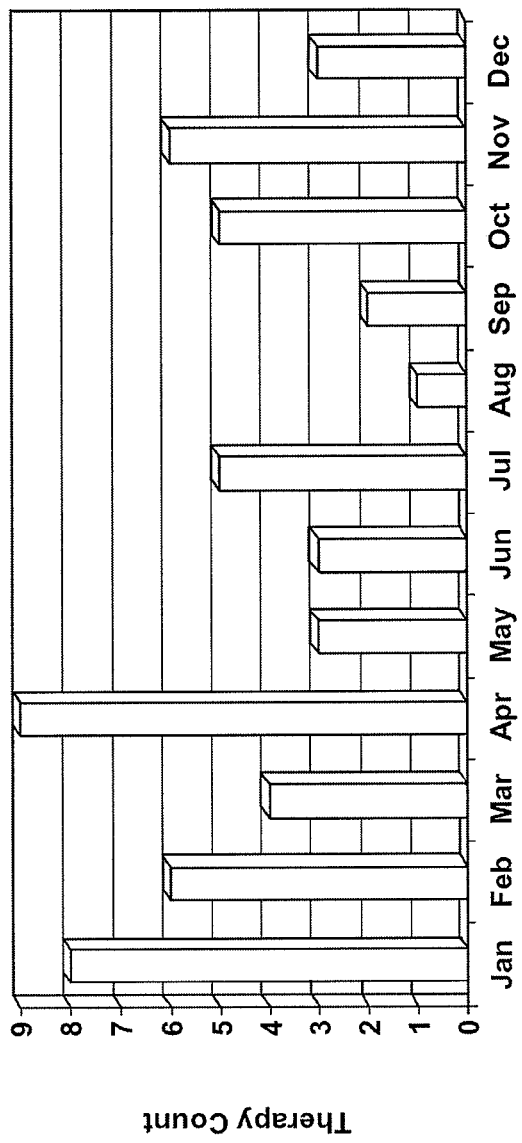
FIG. 60 is a sample therapy trending report displaying therapy trends derived from therapy event log data communicated from a medical device to a medical device server.

FIG. 60 shows a therapy trending report 6000. The therapy trending report 6000 displays a chart of therapy related events over time. In the embodiment shown, the therapy trending report 6000 displays a bar chart showing the frequency of therapy events by month. Other configurations displaying trends in therapy events are possible as well.

FIG. 61 shows a therapy change history report 6100. The therapy change history report 6100 also displays the same information as is displayed in the medical device event history report 5800 of FIG. 58, but only displays therapy change event information. Therapy change events correspond to changed parameters in delivering a therapy using a medical device. The therapy change history report 6100 includes a medical device label 6102, date and time information 6104, class information 6106, trigger information 6108, message information 6110, location information 6112, and drug information 6114, each of which operate analogously to the corresponding entries in the medical device event history report 5800 and the therapy history report 5900.

Figure 62:
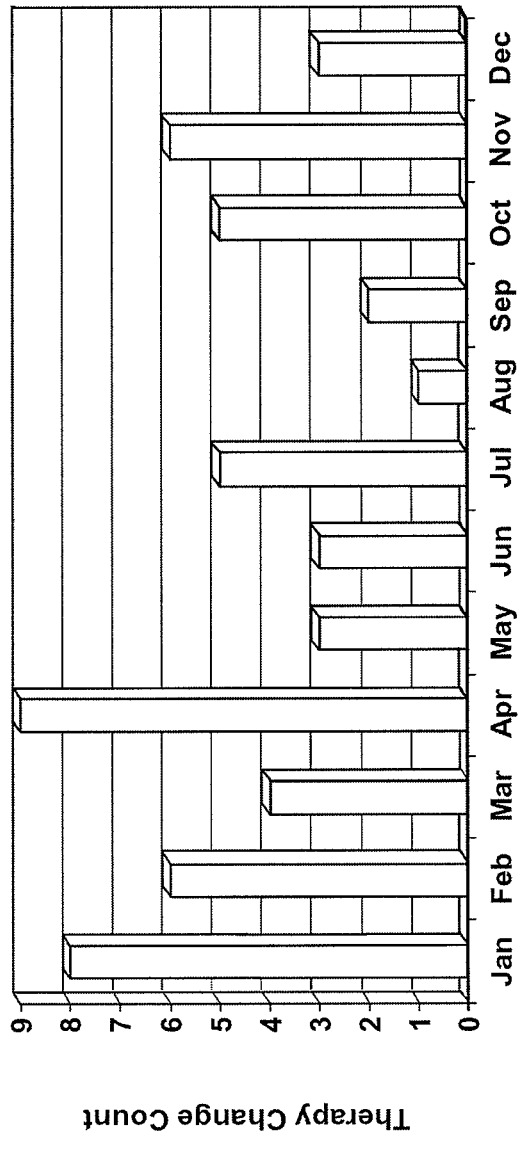
FIG. 62 is a sample therapy change trending report displaying therapy change trends derived from therapy event log data communicated from a medical device to a medical device server.

FIG. 62 shows a therapy change trending report 6200. The therapy change trending report 6200 displays a chart of therapy change events over time. In the embodiment shown, the therapy change trending report 6200 displays a bar chart showing the frequency of therapy change events by month. Other configurations displaying trends in therapy change events are possible as well.

C. Event Web Service: On-Line Status and Viewing of Device Activity

Referring now to FIGS. 63-66, various features of the event web service of FIG. 36 are described. The event web service provides a method by which external applications collect event data from the medical device server and back office components. In particular, the event web service provides an indication of the on-line status of the medical device, and also provides user access to telemetry streams allowing near-real-time telemetry information regarding operation of a medical device in the context of a medical device network as described in FIGS. 1 and 3-4.

Figure 63:
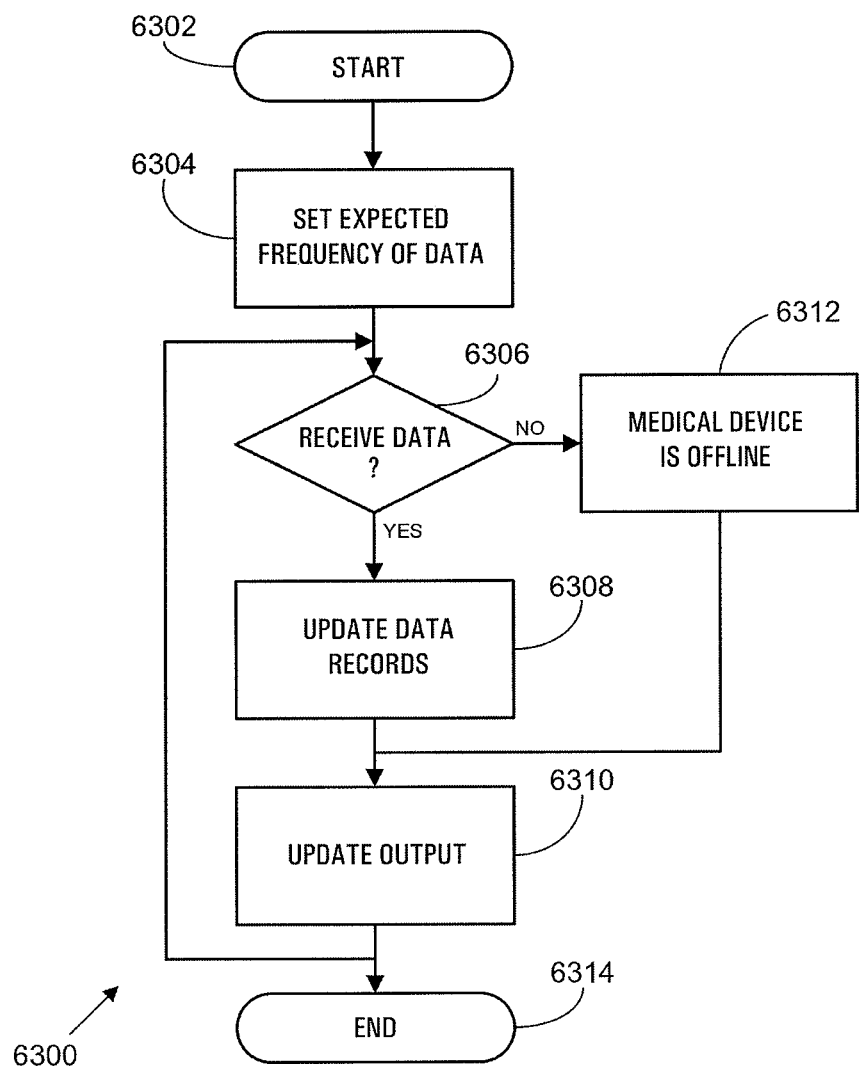
FIG. 63 is a flowchart of systems and methods for determining an on-line status of a medical device.

FIG. 63 is a flowchart of methods and systems for determining the on-line status of a medical device. The system 6300 executes on a medical device server or other back office components, and expects communication from a medical device within a predetermined period in order to ensure accurate communication between the device and server.

Operational flow within the system 6300 commences at a start operation 6302, which corresponds to initial communication between a medical device and a medical device server. Operational flow proceeds from the start operation 6302 to an expectation module 6304. The expectation module 6304 sets in the medical device server and/or back office components an expected, predetermined period within which the medical device server will expect communication.

A receive data operation 6306 determines whether a message has been received by the medical device server. If data has been received by the medical device server, operational flow branches "yes" to an update module 6308, which updates the status of the medical device to indicate that the device is on-line.

An optional output update module 6310 updates data output from the medical device server based on information received in the message. The information received in the message can include medical device status information, event log data, telemetry data, or various other types of data. In one embodiment, the message indicates the beginning of a telemetry stream, and, in response to the message from the medical device, the medical device server and back office components update the appearance of a dashboard screen to reflect the received telemetry data. In a further embodiment, the output update module updates medical device status information in one or more of the back office components.

Operational flow proceeds through the receive data operation 6306, the update module 6308, and the output update module 6310 so long as the medical device continues in operation and the receive data operation 6306 determines that the medical device server continues to send messages to the medical device within the predetermined period.

If the receive data operation 6306 fails to receive data within the predetermined period, the operational flow branches "no" to an offline module 6312, which changes the state of the medical device to offline in the medical device server and/or back office components. Operational flow proceeds to the optional output update module 6310, which updates the output to indicate that the currently displayed data is no longer considered current by the medical device server until additional messages have been received. Operational flow terminates at an end module 6314, corresponding to suspension of operation of the medical device network.

Figure 64:
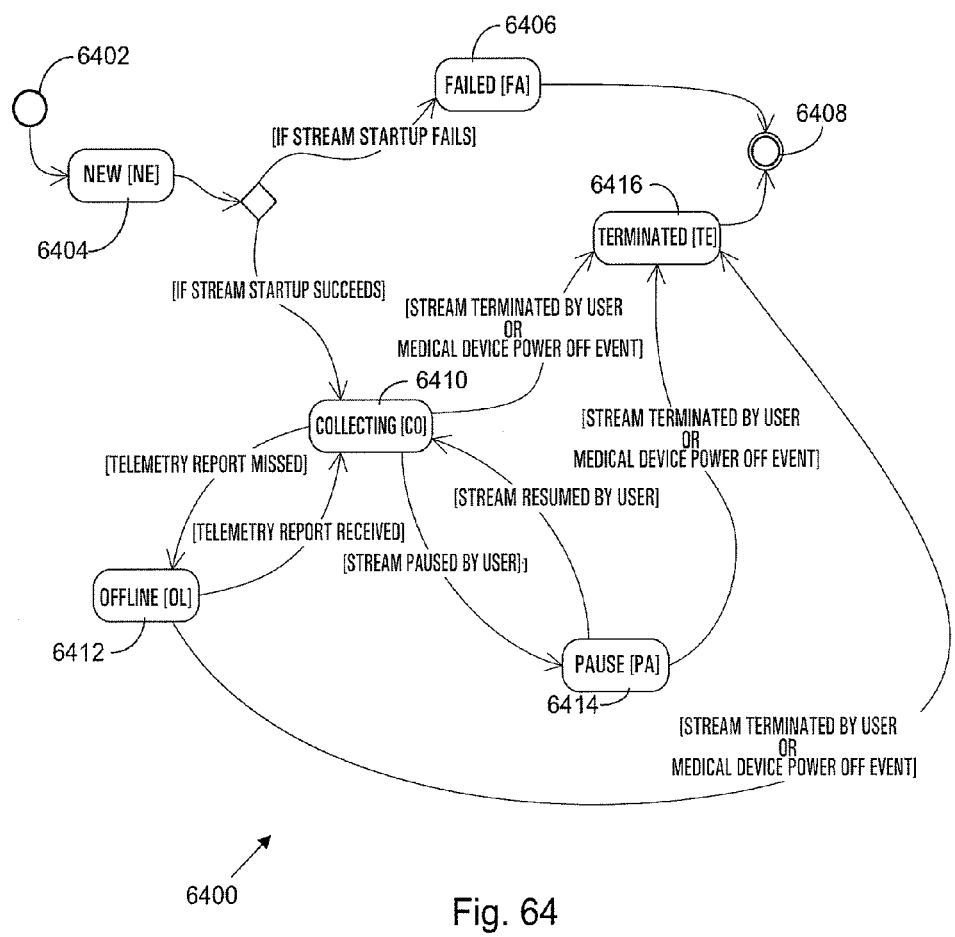
FIG. 64 is a flowchart of systems and methods for collecting telemetry data from a medical device.
Figure 65:
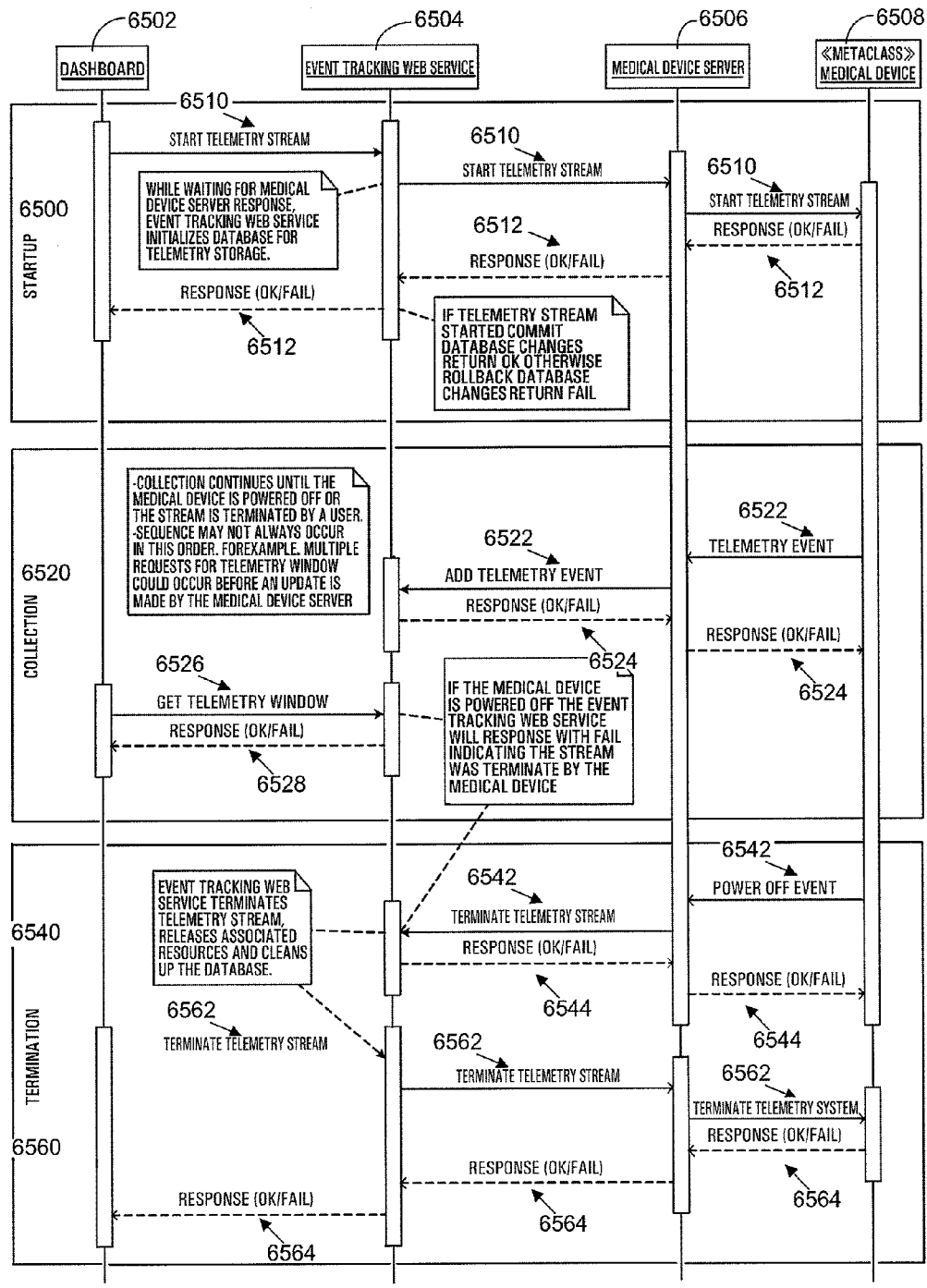
FIG. 65 is an exemplary messaging sequence for receiving telemetry data from a medical device.
Figure 66:
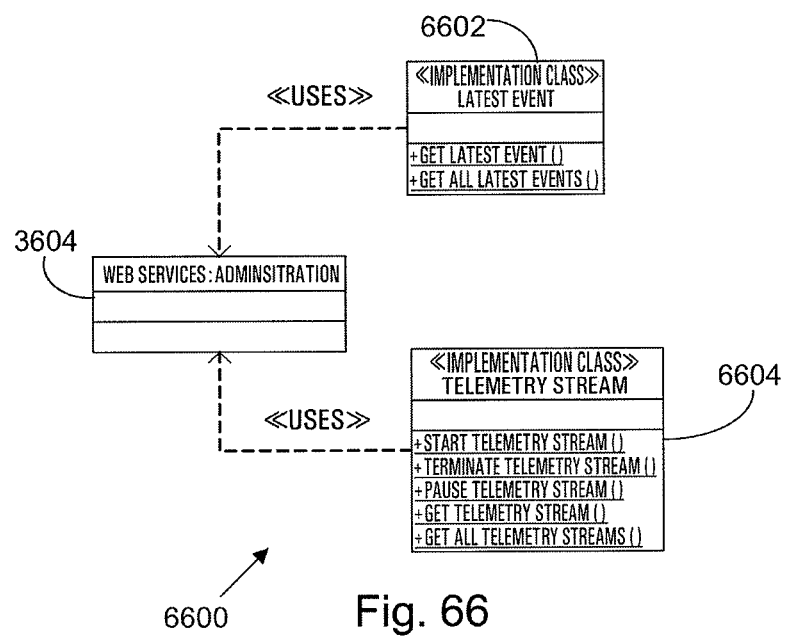
FIG. 66 is schematic diagram including metadata useable to facilitate communication of telemetry data from medical devices to a medical device server.

FIGS. 64-66 provide methods and systems for operation of telemetry streams received from a medical device. The telemetry streams described herein provide nearly-continuous communication from the medical devices to the medical device server, and are viewable on a dashboard or other web portal.

FIG. 64 shows a flowchart of systems and methods for near-real-time display of telemetry information from a medical device. Operational flow in the system 6400 commences at a start node 6402, which corresponds to initial operation of a medical device capable of transmitting a telemetry stream in a medical device network. A new state 6404 indicates that the telemetry stream has not previously been running. After the new state, a stream startup process attempts to start the telemetry stream, as shown in FIG. 65, below. If the stream startup process fails, operational flow proceeds to a failed state 6406, corresponding to failure to start the telemetry stream. Operational flow then proceeds to an end node 6408.

If the stream startup process successfully starts, operational flow proceeds to a collecting state 6410, which corresponds to the medical device server collecting telemetry data from the medical device. In the collecting state, the telemetry data can be stored in the medical device server or other back office components, and also can be output to a dashboard or other monitoring user interface.

From the collecting state 6410, a number of possible options affect operational flow of the system 6400. If a message, including a telemetry stream message, is not sent from the medical device to the medical device server within an expected, predetermined time set in the medical device server or back office components, operational flow proceeds to an offline state 6412. The offline state 6412 corresponds to the system no longer regularly receiving telemetry data.

If a telemetry report is later received, the system 6400 returns to the collecting state 6410.

If the telemetry stream is paused by a user, operational flow proceeds to a paused state 6414, corresponding to a system which only temporarily is not receiving telemetry data. The user can resume the telemetry stream to return the system 6400 to the collecting state.

A terminated state 6416 can be reached from the collecting state 6410, the offline state 6412, or the paused state 6414 by the user terminating the stream or the system otherwise receiving a medical device power off event. The terminated state 6414 corresponds to ending the telemetry stream. In the terminated state, the system no longer receives information from the medical device, and the dashboard is not updated. In a possible embodiment, when the system 6400 is in the terminated state, a dashboard or other monitoring interface indicates to a user that data is not currently being collected. From the terminated state, operational flow proceeds to the end node 6408.

FIG. 65 displays exemplary telemetry stream message sequences 6500, 6520, 6540, and 6560 performed among: a dashboard 6502, such as the one shown in FIG. 67; an event tracking web service 6504, such as the one shown in FIG. 36; a medical device server 6506, as disclosed above in FIGS. 3-4; and a medical device 6508, such as shown in FIG. 2. A first telemetry stream message sequence 6500 illustrates a request to initiate a telemetry stream from a medical device to a dashboard. The message sequence 6500 starts by the dashboard 6502 sending a start telemetry stream message 6510 to the event tracking web service 6504. The event tracking web service communicates the message 6510 to the medical device server 6506, which in turn communicates the message 6510 to the medical device 6508. The medical device generates a response message 6512 indicating success or failure of the message. The response message is related back to the dashboard 6502 by the medical device server 6506 and event tracking web service 6504.

A second telemetry stream message sequence 6520 illustrates initiation of a telemetry stream by a medical device 6508. The medical device 6508 generates a telemetry event 6522, which includes near-continual communication of telemetry data from the medical device 6508 to the medical device server 6506, which relays the telemetry data to the dashboard 6502 via the event tracking web service 6504. The dashboard 6502 displays the telemetry data to the user in a near-real-time fashion. In one embodiment, the dashboard recreates the appearance of the medical device. The dashboard transmits a response message 6524 to the event tracking web service 6504, indicating successful receipt of the telemetry stream.

The dashboard 6502 generates a get telemetry window message 6526 and transmits the message to the event tracking web service, which responds with a message 6528 indicating success or failure of the command. The telemetry window is started at this point, and the dashboard or web portal will display telemetry data.

At this point, if the medical device is powered off, the event tracking web service 6504 will respond with a fail message and will terminate the telemetry stream.

A third telemetry stream message sequence 6540 illustrates ending a telemetry stream by shutting off the medical device generating the telemetry stream. The medical device 6508 generates a power off event message 6542 and sends the message to the medical device server 6506. The medical device server sends a terminate telemetry stream message to the event tracking web service 6504. The event tracking web service 6504 generates a response message 6544 indicating success or failure of receipt of the message 6542. The medical device server 6506 relays the response message 6544 to the medical device 6508.

A fourth telemetry stream message sequence 6560 relates to the sequence 6540 and illustrates ending a telemetry stream by discontinuing the telemetry stream at the dashboard 6502. The dashboard 6502 generates a terminate telemetry stream message 6562, which is communicated from the dashboard to the event tracking web service 6504, and in turn through the medical device server 6506 to the medical device 6508. The medical device 6508 terminates its telemetry stream and generates a response message 6564 indicating success or failure of receipt of the message 6562. The medical device server relays the message 6564 through the event tracking web service 6504 to the dashboard 6502. Additional messaging processes are possible in order to start and terminate telemetry streams using medical devices and dashboards according to the present disclosure.

FIG. 66 shows an exemplary class structure defining a telemetry stream class 6600. The telemetry stream structure 6600 illustrates a portion of the functionality of the event web service module 3606. The telemetry stream relates back to and uses a variety of functions from the administrative web service 3700 of FIG. 37.

The telemetry stream structure 6600 includes a telemetry stream class 6602 and a latest event class 6604. The telemetry stream class 6602 includes a variety of telemetry-related operations, including starting, terminating, pausing, and retrieving available telemetry streams. Additional telemetry stream operations can be included in the telemetry stream class 6602 as well. The latest event class 6604 includes functions for retrieving the latest events, so as to determine when the most recent event was received from the medical device and thereby determine the on-line status of the medical device, so as to determine the availability of telemetry stream data. Additional functions can be included in the latest event class 6604, and additional classes can be added to the telemetry stream structure 6600.

Various exemplary dashboards may be used to view telemetry data at a workstation of other computing device. One example dashboard is shown in FIG. 67. The dashboard 6700 displays telemetry data (e.g. current or near-current operational status) relating to the pumps with which it is associated. The dashboard 6700 can be any of a number of dashboard applications configured to receive and display telemetry data to a user in a near-real-time manner, and can correspond, for example, to the dashboards logically illustrated as dashboard 328 of FIGS. 3-4. The dashboard 6700 can be updated by a telemetry stream, such as described above in FIGS. 64-66.

In the embodiment shown, the dashboard 6700 tracks a name 6702, identifier 6704, domain 6706, address 6708, port 6710, and activity history 6712, with respect to each medical device associated with the dashboard. The name 6702 corresponds to a name of a device recognizable to a user, assigned by either the device itself or the server. The identifier 6704 provides a unique identification useable by the server to verify the identity of the medical device. In various embodiments, the identifier can correspond to a globally-unique identifier (GUID), hardware address, or other identification of the medical device. The domain 6706 indicates the name of a network in which the medical device resides. The address 6708 provides connection information regarding how to communicate with the medical device from the server. In the embodiment shown, the address 6708 is shown as an IP address of the medical device. The port 6710 lists the inbound communication port for the medical device. The activity history field 6712 lists a date and time of the last event occurring on the medical device and communicated to the server.

The dashboard 6700 graphically illustrates an operational status of the pumps with which it is associated. In the embodiment shown, five medical devices are tracked in the dashboard 6700, named "MD0333", "MD0444", "MD0524", "MD0324", and "MD0988." The first, fourth, and fifth devices (MD0333, MD0324, and MD0988) are illustrated as powered and delivering a therapy to a patient. The second device (MD0444) is shown to be in an alarm state, indicating a possible abnormal operation of the device or emergency condition related to the patient associated with that device. The third device (MD0524) is illustrated to be in a fault state, indicating a malfunction or error occurring in that medical device. Other states illustrating an operational status may be illustrated on the dashboard 6700 as well.

Optionally, additional features can be included in the dashboard 6700 that allow a user to filter or display different types of information. In the embodiment shown, a pause check box 6714 and an offline devices check box 6716 allow a user to selectably modify the dashboard. The pause check box 6714, when selected, causes the dashboard to "freeze" temporarily halting the updating of information in the dashboard to allow a user to view the state of the dashboard at a single time. When the pause check box 6714 is unselected, the status information on the dashboard can continually update as data is received from the associated medical devices. The offline devices check box 6716 enables the dashboard to display information related to devices associated with the dashboard, but which are not online and from which the dashboard has not received recent status information. Other display features and filters can be incorporated into the dashboard as well, allowing a user to select the desired set of devices to monitor and allowing the user to view a specific portion of the telemetry data received from those users.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The invention claimed is:

1. A method of tracking changed parameters in a plurality of medical infusion pumps, each of the medical infusion pumps having first, common metadata associated therewith by which to communicate a defined device identifier for that medical infusion pump and second metadata associated therewith by which to communicate operational data collected by that medical infusion pump, the method comprising:

programming each medical device to have the first common metadata and the respective second metadata;

establishing communication sessions between the medical infusion pumps and a medical device server;

in respect of each of the medical infusion pumps, communicating a packet of information including the first metadata and defined device identifier for that medical infusion pump and the second metadata and an original parameter value of operational data, an updated parameter value of operational data, and a final parameter value of operational data from that medical infusion pump to the medical device server;

at the server, processing each packet of information to determine the defined device identifier communicated with the first metadata; and storing the original parameter value, the updated parameter value, and the final parameter value of the operational data in relation to the second metadata of each respective medical infusion pump on the medical device server for the respective medical infusion pump in relation to the defined device identifier of the first metadata of that medical infusion pump.

2. The method of claim 1, further comprising comparing the final parameter value of the operational data of at least one of the medical infusion pumps to a limit stored on the server.

3. The method of claim 2, further comprising, upon determining that the final parameter value of the operational data is outside the limit, triggering an alarm in the medical device server.

4. The method of claim 2, further comprising, upon determining that the final parameter value of the operational data is outside the limit, communicating the alarm.

5. The method of claim 2, further comprising, upon determining that the final parameter value of the operational data is outside the limit, storing the parameter values in event log data on the medical device server for the medical infusion pump in relation to the defined device identifier of the first metadata of that medical infusion pump.

6. A system for tracking changed parameters in a plurality of medical infusion pumps, the system comprising:

a plurality of medical infusion pumps each having a defined device identifier programmed therewith, each adapted to collect operational data comprised of at least one programmable parameter developed in connection with the use thereof, each having a first common metadata associated therewith by which to communicate the defined device identifier for that medical infusion pump, each having second metadata associated therewith by which to communicate operational data of the respective medical infusion pump;

a medical device server communicatively connected to the medical infusion pumps, the medical device server comprising:

a memory configured to store parameter values;

a programmable circuit operatively connected to the memory, the programmable circuit configured to execute program instructions to:

establish communication sessions between the medical infusion pumps and the medical device server;

receive from each medical infusion pump a packet of information including the first metadata and defined device identifier for that medical infusion pump and the second metadata and an original parameter value of operational data, an updated parameter value of operational data, and a final parameter value of operational data from the medical infusion pump;

process the packet of information to determine the defined device identifier communicated with the first metadata; and store the original parameter value, the updated parameter value, and the final parameter value of operational data in relation to the second metadata of each respective medical infusion pump in the memory for the respective medical infusion pump in relation to the defined device identifier of the first metadata of that medical infusion pump.

7. The system of claim 6, the programmable circuit further configured to execute program instructions to compare the final parameter value of at least one of the medical infusion pumps to a limit stored on the server.

8. The system of claim 7, the programmable circuit further configured to execute program instructions to trigger an alarm in the medical device server upon determining that the final parameter value of the operational data is outside the limit.

9. The system of claim 7, the programmable circuit further configured to execute program instructions to communicate the alarm upon determining that the final parameter value of the operational data is outside the limit.

10. The system of claim 7, the programmable circuit further configured to execute program instructions to store the parameter values in event log data on the medical device server for the medical infusion pump in relation to the defined device identifier of the first metadata of that medical infusion pump upon determining that the final parameter value of the operational data is outside the limit.

11. A method of determining an operational capability of a medical device at a server, the medical device having a defined device identifier and being adapted to collect operational data developed in connection with the use thereof, the method comprising:
programming the medical device to have first metadata with the medical device by which to communicate the defined device identifier;
programming the medical device to have second metadata with the medical device by which to communicate the operational data collected thereby, the second metadata being an item identifying the operational data collected;
receiving at the server a packet of information from the medical device including the first metadata associated therewith communicating the device identifier thereof and the second metadata associated therewith communicating at least a portion of the operational data collected thereby;
at the server, processing the packet of information to determine the defined device identifier, based on the first metadata, and the communicated operational data, based on the second metadata; and
when the device identifier does not match a known medical device, evaluating the operational data to determine at least one operational capability of the medical device.

12. A system comprising a server and a plurality of medical devices, the server being communicatively connected to the medical devices, wherein:
each of the medical devices (a) has a defined device identifier, (b) is adapted to collect operational data developed in connection with the use thereof, (c) is programmed to have first common metadata by which to communicate the defined device identifier for that medical device, and (c) is programmed to have respective second metadata by which to communicate operational data of that medical device; and
the server has memory configured to store operational data and a programmable circuit operatively connected to the memory and configured to execute program instructions to (a) receive from each medical device a packet of information including (i) the first metadata and defined device identifier for that medical device infusion pump and (ii) the second metadata and operational data of that medical device, and (b) process each packet of information to determine the defined device identifier based on the first metadata and, at least where the device identifier matches a known medical device, determine the operational data based on the second metadata.

13. The system of claim 12, the programmable circuit further configured to execute program instructions to store the determined operational data in the memory.

14. The system of claim 12, the programmable circuit further configured to execute program instructions to quarantine a packet of information from a particular medical device when the device identifier does not match a known medical device.

15. The system of claim 12, the programmable circuit further configured to execute program instructions to select a medical device based on the device identifier thereof and cause a packet of information to be sent the selected medical device, the packet of information including the first, common metadata communicating the device identifier.

16. The system of claim 12, wherein a first of the plurality of medical devices is from one medical device manufacturer and a second of the plurality of medical devices is from a another, different medical device manufacturer.

17. The system of claim 12, the programmable circuit further configured to execute program instructions to compare the operational data from at least one of the medical devices to a predefined limit and trigger an alarm at the server when the operational data from the medical device is outside the predefined limit.

18. The system of claim 17, the programmable circuit further configured to execute program instructions to cause, when the operational data from the medical device is outside the predefined limit, a packet of information to be sent to the medical device including the first, common metadata communicating the device identifier and third metadata by which to communicate alarm data indicating that the operational data of the medical device is outside the predefined limit.

19. The system of claim 17, the programmable circuit further configured to execute program instructions to cause, when the operational data from the medical device is outside the predefined limit, a packet of information to be sent to a networked computing system including the first, common metadata communicating the device identifier and third metadata by which to communicate alarm data indicating that the operational data of the medical device is outside the predefined limit.

20. The system of claim 12, the programmable circuit further configured to execute program instructions to cause, when the operational data from the medical device is outside the predefined limit, a packet of information to be sent to the medical device including the first, common metadata communicating the device identifier and third metadata by which to communicate alarm data indicating that the operational data of the medical device is outside the predefined limit.

21. The system of claim 12, the programmable circuit further configured to execute program instructions to cause, when the operational data from the medical device is outside the predefined limit, a packet of information to be sent to a networked computing system including the first, common metadata communicating the device identifier and third metadata by which to communicate alarm data indicating that the operational data of the medical device is outside the predefined limit.

22. The system of claim 12 wherein the operational data is selected from the group consisting of basal rate, bolus rate, program volume delivered, total volume delivered, plunger position, plunger force, therapy threshold, respiration rate, heart rate, blood oxygen level, blood glucose level, patient pain level, power event, alarm event, fault event, maintenance event, telemetry event, therapy event, therapy change event, and custom event, patient data, user data, control data, drug data, and location data.

23. The system of claim 12, the respective second metadata associated with each respective medical device includes different second metadata associated with at least some of the respective medical devices whereby the second metadata thereof is not common thereamong.

24. A system for determining an operational capability of a medical device at a server comprising:

a medical device (a) having a defined device identifier, (b) adapted to collect operational data developed in connection with the use thereof, (c) having a first metadata programmed therewith by which to communicate the defined device identifier for that medical device, and (c) having second metadata programmed therewith by which to communicate operational data of that medical device; and a server being communicatively connected to the medical device, the server having a memory configured to store operational data and a programmable circuit operatively connected to the memory and configured to execute program instructions to (a) receive from the medical device a packet of information including (i) the first metadata and defined device identifier for that medical device infusion pump and (ii) the second metadata and at least a portion of operational data of that medical device, and (b) process the packet of information to determine the defined device identifier based on the first metadata and, at least where the device identifier does not match a known medical device, determine the operational data based on the second metadata and evaluate the operational data to determine at least one operational capability of the medical device.

* * * * *